(12) United States Patent
Nolan et al.

(10) Patent No.: US 11,255,840 B2
(45) Date of Patent: Feb. 22, 2022

(54) METHODS OF AND SYSTEMS FOR MEASURING ANALYTES USING BATCH CALIBRATABLE TEST STRIPS

(71) Applicant: Biometry Inc., Boston, MA (US)

(72) Inventors: Bryan Nolan, Brookline, MA (US); Thomas T. Morgan, Stow, MA (US); David L. Carnahan, Needham, MA (US)

(73) Assignee: Biometry Inc., Boston, MA (US)

( * ) Notice: Subject to any disclaimer, the term of this patent is extended or adjusted under 35 U.S.C. 154(b) by 89 days.

(21) Appl. No.: 16/319,173

(22) PCT Filed: Jul. 19, 2017

(86) PCT No.: PCT/US2017/042830
§ 371 (c)(1),
(2) Date: Jan. 18, 2019

(87) PCT Pub. No.: WO2018/017699
PCT Pub. Date: Jan. 25, 2018

(65) Prior Publication Data
US 2020/0200733 A1     Jun. 25, 2020

Related U.S. Application Data

(60) Provisional application No. 62/363,971, filed on Jul. 19, 2016.

(51) Int. Cl.
*G01N 33/497* (2006.01)
*G01N 1/28* (2006.01)
(Continued)

(52) U.S. Cl.
CPC ............. *G01N 33/497* (2013.01); *G01N 1/28* (2013.01); *G01N 33/5438* (2013.01); *G01N 33/552* (2013.01); *G01N 2001/2893* (2013.01)

(58) Field of Classification Search
CPC .... G01N 33/497; G01N 1/28; G01N 33/5438; G01N 33/552; G01N 2001/2893;
(Continued)

(56) References Cited

U.S. PATENT DOCUMENTS 4,802,487 A     2/1989   Martin et al.
5,169,512 A    12/1992   Wiedenmann et al.
(Continued)

FOREIGN PATENT DOCUMENTS

CA     2849868 A1    5/2013
CA     2849872 A1    5/2013
(Continued)

OTHER PUBLICATIONS

Binions et al., "Discrimination Effects in Zeolite Modified Metal Oxide Semiconductor Gas Sensors", IEEE Sensors Journal, vol. 11, No. 5, May 1, 2011, pp. 1145-1151.
(Continued)

*Primary Examiner* — Benjamin R Schmitt
(74) *Attorney, Agent, or Firm* — Wilmer Cutler Pickering Hale and Dorr LLP

(57) ABSTRACT

Systems and methods for measuring analytes in fluid samples are disclosed. The systems and methods employ test strips which are generally comprised of a substrate, at least one electrical connection, at least one sensing chemistry and at least one additional layer. The test strips can be batch calibrated.

26 Claims, 56 Drawing Sheets

(51) Int. Cl.
*G01N 33/543* (2006.01)
*G01N 33/552* (2006.01)

(58) Field of Classification Search
CPC . A61B 2010/0087; A61B 13/00; A61B 5/151; A61B 10/00
USPC .................................................. 73/23.3, 31.05
See application file for complete search history.

(56) References Cited

U.S. PATENT DOCUMENTS

| | | | |
|---|---|---|---|
| 5,239,483 | A | 8/1993 | Weir |
| 5,698,083 | A | 12/1997 | Glass |
| 6,200,444 | B1 * | 3/2001 | Ahlers ................. G01N 31/221 204/416 |
| 6,612,306 | B1 | 9/2003 | Mault |
| 7,179,421 | B1 | 2/2007 | Ho |
| 7,189,360 | B1 | 3/2007 | Ho |
| 7,956,525 | B2 | 6/2011 | Armitage et al. |
| 9,170,248 | B2 | 10/2015 | Fleischer et al. |
| 9,315,463 | B2 | 4/2016 | Prat Quinones et al. |
| 9,329,161 | B2 | 5/2016 | Fleischer et al. |
| 2003/0057109 | A1 | 3/2003 | Wang et al. |
| 2003/0175161 | A1 | 9/2003 | Gabriel et al. |
| 2004/0133116 | A1 | 7/2004 | Abraham-Fuchs et al. |
| 2007/0048180 | A1 | 3/2007 | Gabriel et al. |
| 2007/0114130 | A1 | 5/2007 | Lankheet et al. |
| 2007/0114138 | A1 | 5/2007 | Krasteva et al. |
| 2007/0281288 | A1 | 12/2007 | Belkin et al. |
| 2008/0026473 | A1 | 1/2008 | Wang et al. |
| 2008/0214917 | A1 | 9/2008 | Boecker |
| 2009/0320560 | A1 | 12/2009 | Ross |
| 2010/0106039 | A1 | 4/2010 | Abraham-Fuchs et al. |
| 2010/0176006 | A1 | 7/2010 | Bickford et al. |
| 2010/0183620 | A1 | 7/2010 | Bhawe et al. |
| 2010/0282245 | A1 | 11/2010 | Star et al. |
| 2011/0070634 | A1 | 3/2011 | Takahashi et al. |
| 2011/0077544 | A1 | 3/2011 | Abraham-Fuchs et al. |
| 2011/0098591 | A1 | 4/2011 | Haick et al. |
| 2011/0138904 | A1 | 6/2011 | Nakaso |
| 2012/0065535 | A1 | 3/2012 | Abraham-Fuchs et al. |
| 2012/0148634 | A1 | 6/2012 | Dodd et al. |
| 2012/0263760 | A1 | 10/2012 | Dodd et al. |
| 2013/0062211 | A1 | 3/2013 | Deshusses et al. |
| 2013/0274716 | A1 | 10/2013 | Say et al. |
| 2014/0042025 | A1 | 2/2014 | Furuta |
| 2014/0065219 | A1 | 3/2014 | Bosch et al. |
| 2014/0130574 | A1 | 5/2014 | Happ et al. |
| 2015/0112221 | A1 | 4/2015 | von Sicard et al. |
| 2016/0081589 | A1 | 3/2016 | Reisinger et al. |

FOREIGN PATENT DOCUMENTS

| | | | |
|---|---|---|---|
| CA | 2892931 | A1 | 6/2014 |
| CN | 101742964 | A | 6/2010 |
| CN | 102023178 | A | 4/2011 |
| CN | 102253105 | A | 11/2011 |
| CN | 102368953 | A | 3/2012 |
| CN | 102596030 | A | 7/2012 |
| CN | 104883971 | A | 9/2015 |
| CN | 105050501 | A | 11/2015 |
| CN | 106687035 | A | 5/2017 |
| DE | 102007049715 | A1 | 7/2008 |
| DE | 102014210574 | A1 | 12/2015 |
| DE | 102014219132 | A1 | 3/2016 |
| GB | 2469803 | A | 11/2010 |
| JP | H06-265499 | A | 9/1994 |
| JP | H06-288974 | A | 10/1994 |
| JP | 2002-357589 | A | 12/2002 |
| JP | 2007/192805 | A | 8/2007 |
| JP | 2008-180529 | A | 8/2008 |
| JP | 2009-537219 | A | 10/2009 |
| JP | 2010/025721 | A | 2/2010 |
| JP | 2010-048580 | A | 3/2010 |
| JP | 2014-522973 | A | 9/2014 |
| JP | 2016-136152 | A | 7/2016 |
| KR | 2008-0038541 | A | 5/2008 |
| KR | 10-1786803 | B1 | 11/2017 |
| WO | WO-2005/082934 | A2 | 9/2005 |
| WO | WO-2006/012451 | | 2/2006 |
| WO | WO-2007/006926 | | 1/2007 |
| WO | WO-2007/039297 | | 4/2007 |
| WO | WO-2007/064912 | | 6/2007 |
| WO | WO-2007/136523 | A2 | 11/2007 |
| WO | WO-2007/141510 | A1 | 12/2007 |
| WO | WO-2008/039165 | A2 | 4/2008 |
| WO | WO-2008/099072 | | 8/2008 |
| WO | WO-2010/106898 | | 9/2010 |
| WO | WO-2010/121321 | | 10/2010 |
| WO | WO-2011/015620 | | 2/2011 |
| WO | WO-2011/057757 | | 5/2011 |
| WO | WO-2011/141180 | | 11/2011 |
| WO | WO-2014/045584 | A1 | 3/2014 |
| WO | WO-2015/191558 | A1 | 12/2015 |
| WO | WO-2016/105464 | A2 | 6/2016 |

OTHER PUBLICATIONS

European Search Report dated Nov. 15, 2017, in European Application No. 15806563.1, 8 pages.
European Search Report dated Nov. 7, 2017, in European Application No. 15873758.5, 9 pages.
International Search Report and Written Opinion dated Feb. 23, 2016, in the International Application No. PCT/US2015/00180, 18 pages.
International Search Report and Written Opinion dated Sep. 1, 2015, in the International Application No. PCT/US2015/034869, 21 pages.
International Search Report and Written Opinion dated Sep. 29, 2017, in the International Application No. PCT/US2017/042830, 14 pages.
Lange et al., "Chemiresistors based on conducting polymers: A review on measurement techniques", Analytica Chimica Acta, (2011) vol. 687, No. 2, published online Nov. 19, 2010, pp. 105-113.
Seesaard et al., "Health Status Monitoring by Discrimination of Exhaled Breath with an Electronic Nose", The 2012 Biomedical Engineering International Conference (BMEiCON), IEEE, Dec. 5, 2012, pp. 1-5.
English machine translation of JPH06288974. 7 pages.
Binions et al., "Discrimination Effects in Zeolite Modified Metal Oxide Semiconductor Gas Sensors," IEEE Sensors 2009 Conference, Christchurch, New Zealand Oct. 25-28, 2009 pp. 1090-1095.
European Search Report dated Oct. 15, 2019, in the European Patent Application 17831778.0, 15 pages.

* cited by examiner

Figure 12
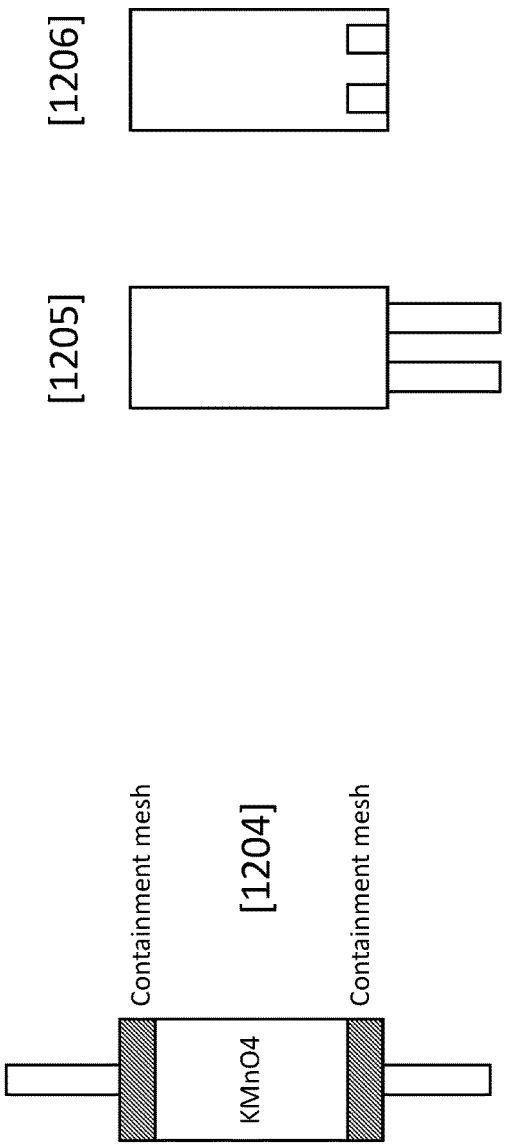

Figure 16

Examples of Coating Techniques for Test Strip Chemistry & Layer

| |
|---|
| Air knife coating |
| Curtain coating |
| Dip coating |
| Doctor blade |
| Drop casting |
| Electropainting |
| Electrophoretic deposition |
| Electrospray |
| Flexography |
| Gravure |
| Hot melt |
| Ink rolling |
| Inkjet |
| Knife over roll (tape casting) |
| Lamination |
| Meyers rod coating |
| Offset |
| Pad printing |
| Press Fitting |
| Roll coating |
| Rotary screen |
| Screen |
| Slot-die |
| Spin coating |
| Spray Coating |

| | Sensing Chemistry Additives |
|---|---|
| Alkyltrimethylammimumsalts | Polyoxyethylenenonylphenylether |
| Anionicsurfactants | Polysaccharides |
| Cationicsurfactants | Polyurethanes |
| Cellulosics | Polyvinyl butyral |
| Clays | Proteins |
| Ethyleneglycol | Silica |
| Fluorosurfactants | Silicones |
| Glycerol | Sodiumdodecylsulfate |
| Nonionicsurfactants | Stearicacid |
| Organicsolvents | Water |
| Polyacrylicacid | Zwitterionicsurfactants |

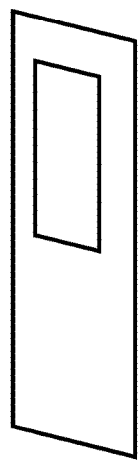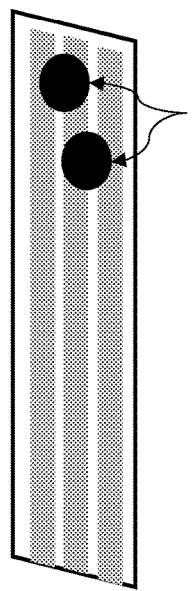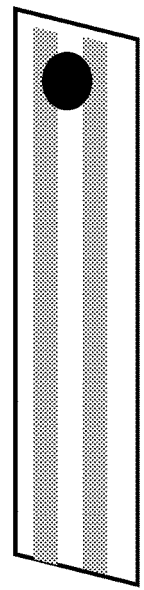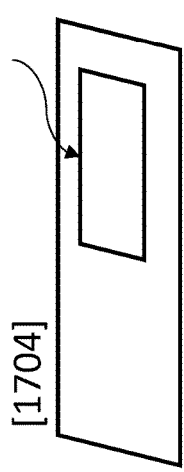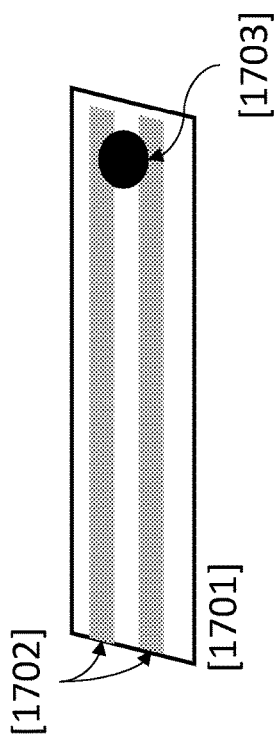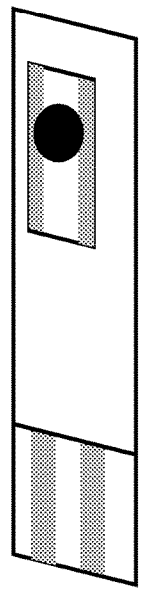
Figure 17A

Figure 17C
[1722] 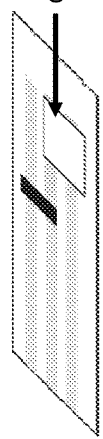
Off Set Chemistry
[1723] 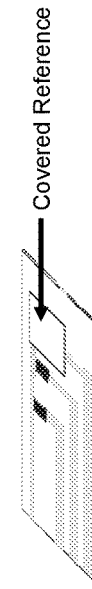
Off Set Chemistry with Covered Reference
[1724] 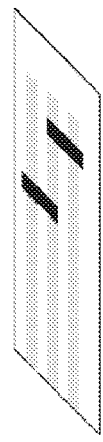
Multiplex
[1725] 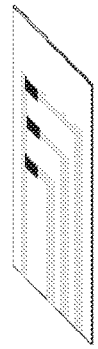
Multiplex with One Covered Reference
[1726] 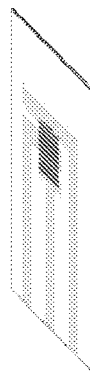
Working, Reference, Counter Electrode Figure 21A
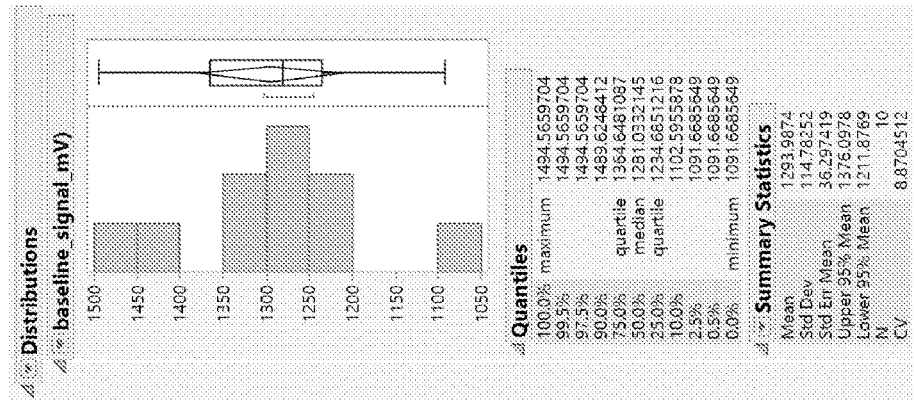
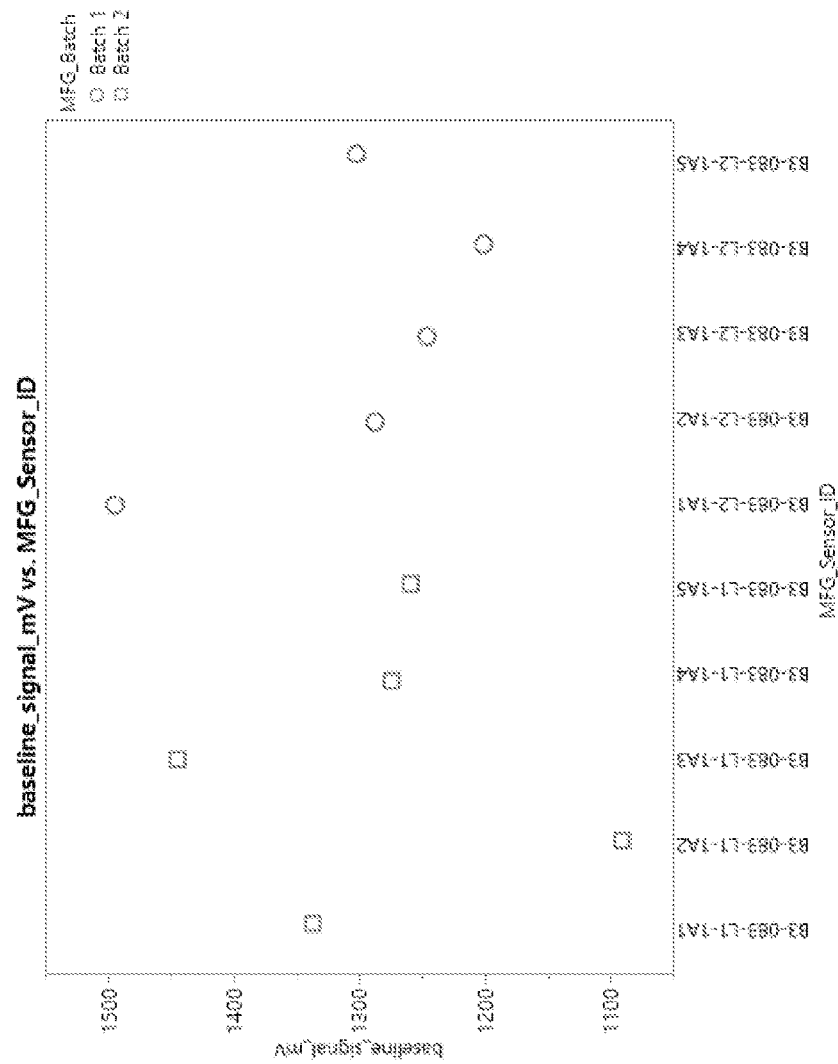

4 point standard curve derived from Batch 1 sensors

Calibration Equation:
Unknown concentration = (AnalogInput - Intercept)/Slope

Figure 25

Patient Questionnaire

In the past 4 weeks, how much of the time did your asthmas keep you from getting as much done at work, school, or at home?

_____

In the past 4 weeks, how often have you had shortness of breath?

_____

In the past 4 weeks, how often did your asthma symptoms (wheezing, coughing, shortness of breath, chest tightness or pain) wake you up at night or earlier than usual in the morning?

_____

In the past 4 weeks, how often have you used your rescue inhaler or nebulizer (such as albuterol)?

_____

How would you rate your asthma control during the past 4 weeks?

_____

METHODS OF AND SYSTEMS FOR MEASURING ANALYTES USING BATCH CALIBRATABLE TEST STRIPS

CROSS-REFERENCE TO RELATED APPLICATIONS

This application is a National Stage Entry of PCT International Application Number PCT/US2017/42830, titled METHODS OF AND SYSTEMS FOR MEASURING ANALYTES USING BATCH CALIBRATABLE TEST STRIPS, filed Jul. 19, 2017, which claims priority under 35 U.S.C. § 119(e) to U.S. Provisional Application No. 62/363,971, filed Jul. 19, 2016, entitled "Methods Of and Systems for Test Strip Regeneration and Sample Manipulation for Use with Same," the content of which is incorporated herein in its entirety.

REFERENCES TO RELATED APPLICATIONS

This application is related to the following listed applications: International Patent Application Number PCT/US15/00180, entitled *MINI POINT OF CARE GAS CHROMATOGRAPHIC TEST STRIP AND METHOD TO MEASURE ANALYTES*, filed Dec. 23, 2015, International Patent Application Number PCT/US15/34869, entitled *LOW COST TEST STRIP AND METHOD TO MEASURE ANALYTE*, filed Jun. 9, 2015, which are included in the attached appendix and incorporated by reference in their entirety.

BACKGROUND

Field of Invention

This invention relates to a gas sensing system that includes a low-cost limited-use test strip configured to measure gas, a system for delivering gas to the test strip and a device for controlling and reading the output of the test strip. In other aspects, the invention is generally related to the diagnosis and monitoring of therapy for patients with chronic respiratory disease such as asthma and chronic obstructive pulmonary disease, and digestive disorders such as food intolerances or irritable bowel syndrome etc. Other medical and non-medical applications for detection of gas are possible without deviating from the spirit of the invention. Examples include but are not limited to hydrogen, methane, sulfur dioxide, nitric oxide, nitrogen dioxide, NOx, ozone, ammonia, etc. Additional background has been previously described by the authors.

Description of Related Art

There are many different types of sensors and technologies available for gas and analyte detection known in the art. The problems associated with these sensors and detection systems has been discussed in the related applications by the authors. Some of those shortcomings include cost, complexity, calibration, quality control, shelf life, ease of use etc. This is not intended to be an exhaustive list.

One of the shortcomings of existing gas sensors is the cost and complexity of calibration. Existing sensors may be batch manufactured but each individual sensor requires calibration. This is often requires building a calibration curve across multiple analyte concentrations, temperatures and humidities. Calibration can take hours or days depending on the sensor which adds significantly to its cost. Sensors must also be frequently re-calibrated or quality controlled to compensate for drifting baseline and/or aging also adding to its cost. One example of this is a metal oxide semiconducting sensor (MOS or CMOS). These sensors are produced on a single wafer in a semiconductor fabrication facility. Post production, the variability in initial or baseline resistance can be 5× across the wafer and the internal heating element may take up to 24 hours with constant power to reach a stable baseline. The variability combined with a non-linear response to the analyte of interest requires each sensor to be individually calibrated to accurately calculate the change in resistance and to correlate that change with an analyte concentration. The ability to batch manufacture and batch calibrate gas sensors is a significant improvement versus existing technology because it reduces the cost associated with production and calibration enabling the sensor to be disposed of after use.

To address these problems, a single use, disposable sensor and re-usable measurement system has been previously described by the applicant in the PCT patent applications incorporated above.

SUMMARY OF THE INVENTION

One aspect of the invention involves a low cost test strip and methods to measure an analyte in a breath sample.

In another aspect of the invention, a system for determining the concentration of at least one analyte in a fluid sample is disclosed, in which the system comprises a test strip and a meter configured to accept a fluid sample from a human user as previously described by the authors. In some embodiments, the meter contains a chamber to convert the analyte of interest into another analyte to be measured. In some embodiments, the meter contains a chamber to alter the physical and/or chemical state of the analyte of interest. In one embodiment, the chamber converts nitrogen monoxide into nitrogen dioxide to be measured by the test strip. In one embodiment of the invention, the conversion chamber is disposable. In another embodiment, the conversion chamber is configured as a removable cartridge. In another embodiment, the conversion chamber has a limited life. In another embodiment of the invention, the conversion chamber is removable and can optionally be replaced by a user.

In some embodiments, the meter contains valves to divert at least a portion of the flow path of exhaled breath. In other embodiments, the meter contains valves to trap at least a portion of exhaled breath for analysis. In other embodiments, the meter contains pressure or flow sensors to measure the exhalation flow rate of the human user.

In some embodiments, the meter contains another chamber to house the test strip. In some embodiments, the meter contains another chamber to buffer the analyte sample prior to measurement. In some embodiments, a pump or pumps move the sample between the buffer chamber and the sensor chamber. In another embodiment, the sample is re-circulated by a pump. A fan or blower may be a suitable alternative to a pump.

In some embodiments, the meter is designed to clean or re-set or re-baseline or re-calibrate the test strip. In one embodiment, the chamber containing the test strip also contains an energy source. In some embodiments, the energy source is UV, RF or IR (non-exhaustive list). In other embodiments, the chamber contains a magnetic field to change the binding properties of the analyte to the test strip, or to clean, re-set, re-baseline or re-calibrate the test strip. In other embodiments, the meter provides additional current or voltage to clean, re-set, re-baseline or re-calibrate the test strip. In some embodiments, the applied energy is designed remove chemical species prior to sensing. In some embodiments, this is done to extend the shelf life or for calibration purposes. In other embodiments, this is done at multiple points during the analysis. In one embodiment, this is done while at least a portion of the sample is delivered to the test strip.

In other embodiments, the energy source is designed to alter the chemical state of at least one analyte in the sample. In yet other embodiments, the magnetic field is designed to alter the electronic, physical or chemical state of at least one analyte in the sample.

In other embodiments, combinations of valves, meters, chambers and flow measurements are used to accurately measure the analyte of interest by controlling the sample delivery to the test strip.

In other embodiments, the chambers contain both an inlet and an outlet for the sample to be measured. In other embodiments, the chambers only contain an inlet. In other embodiments, the chambers contain at least one inlet for the sample.

In other embodiments, the meter removes humidity and/or at least one interfering substance from the device. Examples include but are not limited to nafion tubes, desiccants, energy source, oxidizing or reducing materials etc.

In one aspect, the invention involves a system for determining the concentration of at least one analyte in a fluid sample. In some embodiments, the system includes a chamber adapted for altering the chemical state of at least one analyte in the sample, and a test strip which includes, a base substrate, a first electrode pair disposed over the substrate, an active sensing chemistry in electrical communication with the first electrode pair wherein the sensing chemistry is responsive to the chemically altered analyte. In another embodiment, the system includes a second electrode pair disposed over the substrate and a second sensing chemistry in electrical communication with the second electrode pair. In other embodiment, the first sensing chemistry or the second sensing chemistry may contain at least one or more of carbonyl groups, nanostructures, functional organic dyes, heterocyclic macrocycles, metal oxides, or transition metals.

In another embodiment, the analyte molecules bind to the sensing chemistry, and the partition coefficient of the bound analyte is less than 0.5 under the required conditions for measurement. In another embodiment, the partition coefficient of the bound analyte converting to the unbound analyte is less than 0.25 under the required conditions for measurement. In another embodiment, the partition coefficient of the bound analyte is less than 0.1 under the required conditions for measurement. In another embodiment, the partition coefficient of the bound analyte is less than 0.05 under the required conditions for measurement. In another embodiment, the partition coefficient of the bound analyte is less than 0.01 under the required conditions for measurement.

In some embodiments, the analyte saturates the sensing chemistry after a single exposure to the analyte. In some embodiments, the analyte saturates the sensing chemistry after multiple exposures to the analyte. In some embodiments, the analyte saturates the sensing chemistry after 365 exposures to the analyte. In some embodiments, the analyte saturates the sensing chemistry after 52 exposures to the analyte. In some embodiments, the analyte saturates the sensing chemistry after 12 exposures to the analyte. In some embodiments, the chemical bond is selected from the group consisting of coordination bonds, covalent bonds, hydrogen bonds, ionic bonds, and polar bonds. In some embodiments, the sensing chemistry comprises one or more of carboxyl groups, nanostructures, functional organic dyes, heterocyclic macrocycles, metal oxides, or transition metals.

In some embodiments, the sensing chemistry is a line shape bridging the electrode pair. In some embodiments, the sensing chemistry is a coffee ring shape bridging the electrode pair.

In some embodiments, the system includes a layer that defines a window to expose the sensing chemistry to at least one analyte. In some embodiments, the layer contains an adhesive. In some embodiments, the adhesive is a pressure sensitive adhesive.

In some embodiments, the system is adapted to sense one or more of nitrogen dioxide, nitrogen monoxide, hydrogen, methane, acetone, sulfur dioxide, carbon monoxide, or ozone.

In some embodiments, the system includes one or more of a blower, fan, or pump configured to move the fluid sample to the test strip. In some embodiments, the fluid sample moves to the test strip using the force of exhaled breath.

In some embodiments, the system includes a test strip chamber to house the test strip in fluid communication with the conversion chamber. In some embodiments, the test strip is removable from the test strip chamber. In some embodiments, the system is adapted to track the number of uses of the conversion chamber. In some embodiments, one or more of a blower, pump, fan, or the force of exhaled breath to move the fluid sample through the conversion chamber. In some embodiments, the fluid sample is recirculated between the conversion chamber and the test strip chamber. In some embodiments, the system includes at least one sensor to determine one or more of humidity, temperature, or pressure.

In some embodiments, the system includes a microprocessor adapted to determine or accept information about calibration of a manufacturing lot or batch of test strips.

In some embodiments, the system includes a dehumidifier adapted to remove humidity from the sample. In some embodiments, the dehumidifier includes nafion tube. In some embodiments, the dehumidifier includes a desiccant. In some embodiments, the desiccant includes a silica gel. In some embodiments, the desiccant includes an oxidizer.

In some embodiments, the system includes a filter adapted to remove a gas from the sample determined to interfere with the sensor. In some embodiments, the filter comprises a nafion tube.

In some embodiments, the conversion chamber is removable. In some embodiments, the conversion chamber includes one or more of an oxidizing agent, a reducing agent, a charge transfer agent, an adduct, or a complexation agent. In some embodiments, the conversion chamber is configured to oxidize nitrogen monoxide to nitrogen dioxide. In some embodiments, the conversion chamber includes potassium permanganate. In some embodiments, the potassium permanganate is suspended on a substrate. In some embodiments, the potassium permanganate is suspended on a silica gel. In some embodiments, the conversion chamber comprises sodium permanganate. In some embodiments, the sodium permanganate is suspended on a substrate In some embodiments, the conversion chamber comprises one or more of a UV source, an infrared source, a radio frequency source, or a corona discharge source. In some embodiments, the conversion chamber is adapted to oxidize nitrogen monoxide to nitrogen dioxide. In some embodiments, the sensing chemistry is configured to be responsive to nitrogen dioxide.

In another aspect, the invention includes a method for determining the concentration of an analyte in a fluid sample, including the steps of providing a system for determining the concentration of at least one analyte in a fluid sample, the system including, a conversion chamber for changing the chemical state of at least one analyte in the sample; and a test strip including a base substrate; a first electrode pair disposed over the substrate; an active sensing chemistry in electrical communication with the first electrode pair wherein the sensing chemistry is responsive to the chemically altered analyte; and measuring at least one of a voltage across the first electrode pair, a resistance across the first electrode pair, and a current flow across the first electrode pair. In some embodiments, the fluid is a gas. In some embodiments, the test strips are calibrated by at least one of a manufacturing lot, a manufacturing batch, and sensor position within the lot or batch. Some embodiments, include the further step of accepting a calibration associated with the test strip. In some embodiments, the calibration is accepted by one or more of digital, optical, or manual signal. In some embodiments, the system includes a microprocessor in electrical communication with the test strip. In some embodiments, the microprocessor converts the analog voltage, resistance, or current into an analyte concentration based on the calibration.

In another aspect, the invention includes a system for determining the concentration of at least one analyte in a fluid sample, the system including a plurality of test strips, each test strip including; a base substrate; a first electrode pair disposed over the substrate; and an active sensing chemistry in electrical communication with the first electrode pair, wherein the sensing chemistry is responsive to the analyte and wherein the sensing chemistry is sufficiently homogenous to allow for calibration information from a subset of the plurality of test strips to be used for the plurality of test strips. In some embodiments, the sensing chemistry is disposed over the electrode pair in a line wherein a majority of the sensing chemistry between the electrode pair is concentrated within the line. In some embodiments, the sensing chemistry is disposed over the electrode pair in a coffee ring wherein a majority of the sensing chemistry between the electrode pair is concentrated within the coffee ring.

In another aspect the invention includes a system for determining the concentration of at least one analyte in a fluid sample, the system including a base substrate; a first electrode pair disposed over the substrate; and an active sensing chemistry in electrical communication with the first electrode pair, wherein the sensing chemistry is responsive to the analyte and wherein the sensing chemistry forms a chemical bond with the analyte having a partition coefficient less than 0.5 under the required conditions for measurement. In some embodiments, the chemical bond is selected from the group consisting of coordination bonds, covalent bonds, hydrogen bonds, ionic bonds, and polar bonds. In some embodiments, the sensing chemistry contains one or more of carboxyl groups, nanostructures, functional organic dyes, heterocyclic macrocycles, metal oxides, or transition metals. In some embodiments, the partition coefficient of the bound analyte is less than 0.25 under the required conditions for measurement. In some embodiments, the partition coefficient of the bound analyte is less than 0.1 under the required conditions for measurement. In some embodiments, the partition coefficient of the bound analyte is less than 0.05 under the required conditions for measurement. In some embodiments, the partition coefficient of the bound analyte is less than 0.01 under the required conditions for measurement.

BRIEF DESCRIPTION OF THE DRAWINGS

In the drawings:

FIG. 12 shows illustrative examples of disposable reaction chamber/cartridge configurations according to embodiments of the invention.

FIG. 16 shows a non-exhaustive list of coating techniques for the test strip chemistry and layers and sensing chemistry additives.

FIGS. 17A-17D show configurations of the test strip, sensing chemistry, and layers.

FIG. 21A demonstrates the uniformity of the initial or baseline signal of sensing chemistries manufactured on a test strip prior to sensing.

FIG. 25 depicts certain embodiments of a questionnaire.

DETAILED DESCRIPTION

Figure 1A:
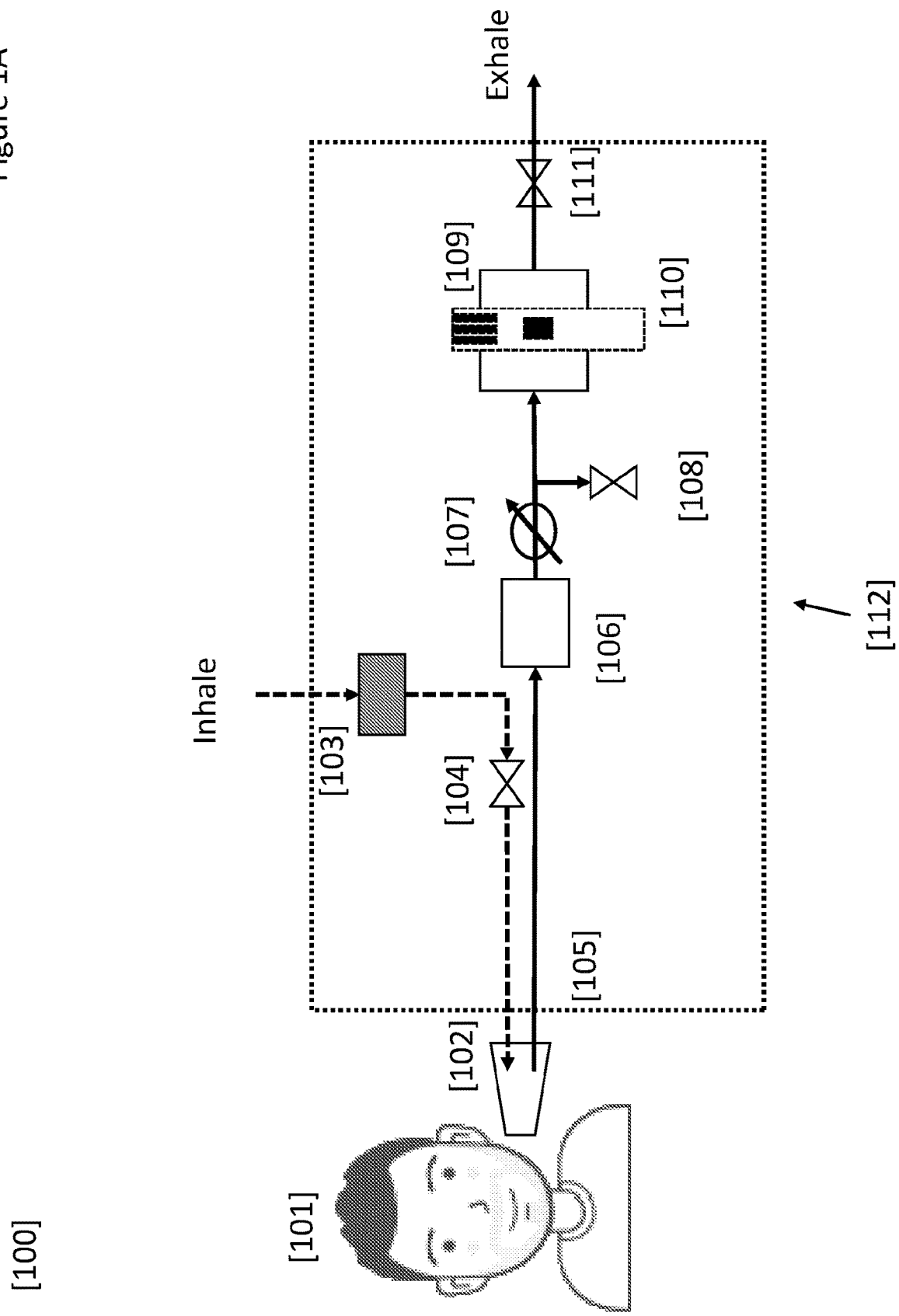
FIG. 1A shows an illustrative example of a system that includes a reaction/conversion chamber, a chamber for the test strip, valves, and a flow rate measurement device according to an embodiment of the invention.

FIG. 1A shows one embodiment [100] of use of a system for measuring an analyte in a gaseous sample in which a patient [101] inhales through a mouth piece [102] connected to a meter [112]. The mouthpiece is in fluid communication with a one-way valve [104] and scrubber [103]. One-way valve [104] permits gas to only pass from the outside environment to the patient. The scrubber [103] removes certain gases from the incoming ambient air that passes into the patient's lungs. In one embodiment, the scrubber is configured to remove NO and $NO_2$ from ambient air. A suitable scrubbing material is activated charcoal but many materials are possible depending on the desired analyte removal. Another example is potassium permanganate or potassium permanganate on silica. Yet another example is activated alumina. The patient then exhales through the mouth piece [102] and into the fluid path of the meter [105]. The flow path may also include a structure to dehumidify the sample stream or to remove certain chemical species. Suitable examples include activated charcoal, activated alumina, potassium permanganate, desiccants, nafion or nafion tubing etc. This is not intended to be an exhaustive list. A reaction chamber (also called a conversion chamber herein) [106], described in more detail below, is in fluid connection with the mouthpiece. Although not shown, a one-way valve is included in the flow path from the mouthpiece [102] to the reaction chamber [106] that permits flow only toward the reaction chamber. A flow rate measurement device (e.g., a flow meter, pressure sensor, venture tube, flow tube, pitot tube, etc.) [107] is positioned in the fluid path of the meter [105]. The flow rate measurement device [107] may also be a side stream from the main fluid path. The flow rate measurement [107] device may be located proximally or distally to the conversion chamber [106]. As mentioned above, the flow rate measurement device may measure pressure and/or pressure differential across an orifice or a flow meter. This is not intended to be an exhaustive list. A valve [108] in fluid connection with the reaction chamber and the test strip chamber [109] allows for at least a portion of the sample to be diverted out of the device (e.g. bypassing the test strip [110]) or to be used in conjunction with another valve [111] to trap the analyte sample in the test strip chamber [109]. Many types of valves are possible without deviating from the spirit of the invention. Types of valves and their function are known in the art. In one embodiment, valves [108] and [111] are solenoid valves modulated by a controller. In another embodiment, valve [108] is opened to atmosphere while the first portion of the exhaled sample is passed through the valve [108]. In some embodiments, the duration of the sample vented through valve [108] is between 0 and 10 seconds. In one embodiment, the duration is less than or equal to 7 seconds. After the pre-determined time has passed, valve [108] is closed by the controller and the sample passes to the test strip chamber [109]. Valve [111] may start opened or closed to atmosphere. In one embodiment, the controller opens valve [111] to atmosphere when valve [108] begins to direct the gas flow to the chamber [109]. After a pre-determined amount of time from the beginning of the exhalation, the controller closes both valves [108] and [111] to trap the gas sample in the chamber [109] with the test strip [110]. In some embodiments, the system may be configured to circulate the trapped gas over the test strip for a prescribed amount of time. In this embodiment, the trapped gas may be circulated using any method known to the art, for example a fan, pump, or blower. In one embodiment, the system is configured to trap at least a portion of the last three seconds of a ten second exhale. In yet another embodiment, valve [108] opens under a set pressure, which acts to vent the sample when valve [111] is closed. In this embodiment, the controller open modulates valve [111] open to cause the sample to pass through the test strip chamber, thereby causing valve [108] to close. In some embodiments, inhaling through the meter is not necessary and the patient may only exhale through the device. In these embodiments [103] and [104] are optional. In some embodiments, the test strip chamber does not fully enclose the test strip. In this embodiment the test trip chamber ensures electrical communication between the test strip and the meter. In another embodiment the test strip chamber ensures the fluid sample is directed to the precise location of the sensing chemistry on the test strip.

Figure 1B:
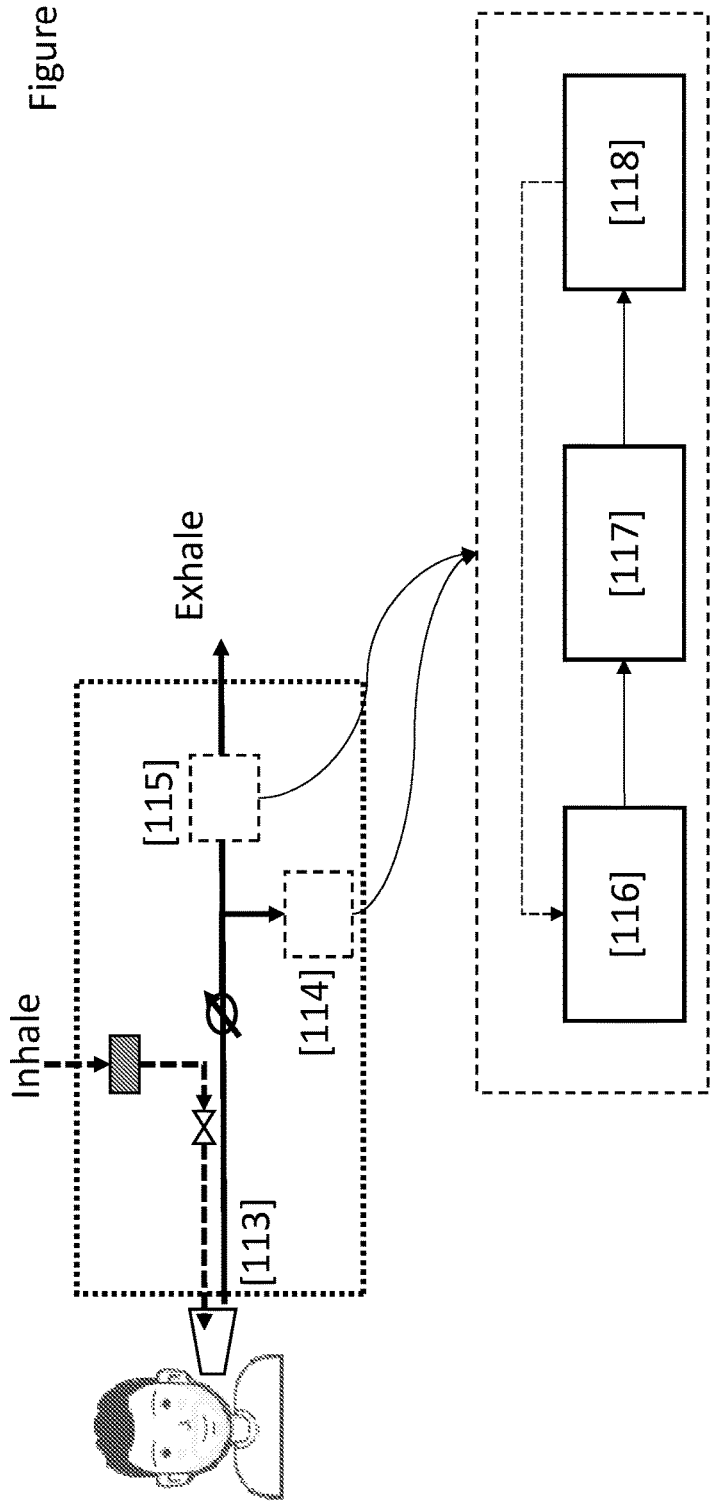
FIG. 1B shows alternative configurations and sequence of events for a system that includes a reaction/conversion chamber, a test strip chamber, and pumps/fans/blowers to measure an analyte.

FIG. 1B shows alternative configurations for the flow paths and sequence of events between the pump or blower or fan, the conversion chamber, and the sensor or sensor chamber. The position in the meter of these elements may be in line with the fluid sample [115] or a side stream from the main fluid sample path [114]. The fluid sample [113] enters the first element [116] then sequentially passes through [117] and [118]. [116], [117], [118] may consist of a pump/fan/blower or a conversion chamber or a sensor/sensor chamber in various configurations. Optionally, one or more of these elements may be removed. In some embodiments, the fluid sample is recirculated between at least two of the elements. In some embodiments, a flow meter and/or any number of valves is placed proximally and/or distally to the elements and/or in between the elements [116], [117], 118]. In some embodiments, the conversation chamber may only remove humidity from the sample. The conversion chamber may contain one or more of an oxidizing agent, a reducing a charge transfer agent, an adduct, or a complexation agent. Examples of these materials include the following.

Oxidizing agent
  Permanganate salts (e.g. potassium permanganate, sodium permanganate)
  Perchlorate salts (e.g. ammonium perchlorate, perchloric acid)
  Peroxides (e.g. hydrogen peroxide, magnesium peroxide)
  Nitrates (e.g. iron nitrate, sodium nitrate, nitric acid)
  Ozone gas
  Peroxy acids (peroxy disulfuric acid)
  Hypochlorites (e.g. sodium hydochlorite)
Reducing agent
  Metal hydrides (e.g. lithium aluminum hydride, sodium borohydride)
  Hydrogen gas
  Iron (II) compounds (e.g. $FeCl_2$)
  Oxalic acid
  Ascorbic acid
Charge Transfer agents
  Acids (e.g. citric acid, hydrochloric acid)
  Bases (e.g. sodium hydroxide, ammonia)
  Ion exchange resins
Adducts
  Lewis acids (e.g. borane)
  Lewis bases (e.g. tetrahydrofuran, ammonia)
Complexation agents
  Ethylene diamine tetraacetic acid
  Herterocyclic macrocycles
  Organometallic compounds In one embodiment, the device is configured to measure ambient levels of nitrogen dioxide and nitrogen monoxide. In a preferred embodiment, the source of the nitrogen monoxide is human breath (i.e. a fractional exhaled nitric oxide FeNO test). In this embodiment, a test strip is sensitized to nitrogen dioxide and the conversion cartridge is configured to oxidize nitrogen monoxide into nitrogen dioxide. A second conversion cartridge may be supplied to record levels of ambient nitrogen dioxide. In this embodiment, the conversion cartridge does not oxidize nitrogen monoxide to nitrogen dioxide. The cartridge may be configured as an empty chamber (i.e. no chemical alteration of the analyte occurs). In variations of this embodiment, the conversion cartridge contains a desiccant. In other variations, the conversion cartridge may alter some chemical state of the sample but does not oxidize nitrogen monoxide into nitrogen dioxide. An application where this would be suitable is to measure ambient indoor or outdoor pollution levels which are known to cause respiratory symptoms and exacerbations in patients with asthma and COPD in the same device that measures exhaled nitric oxide which is an indicator of risk for an exacerbation in asthma and COPD.

Figure 2:
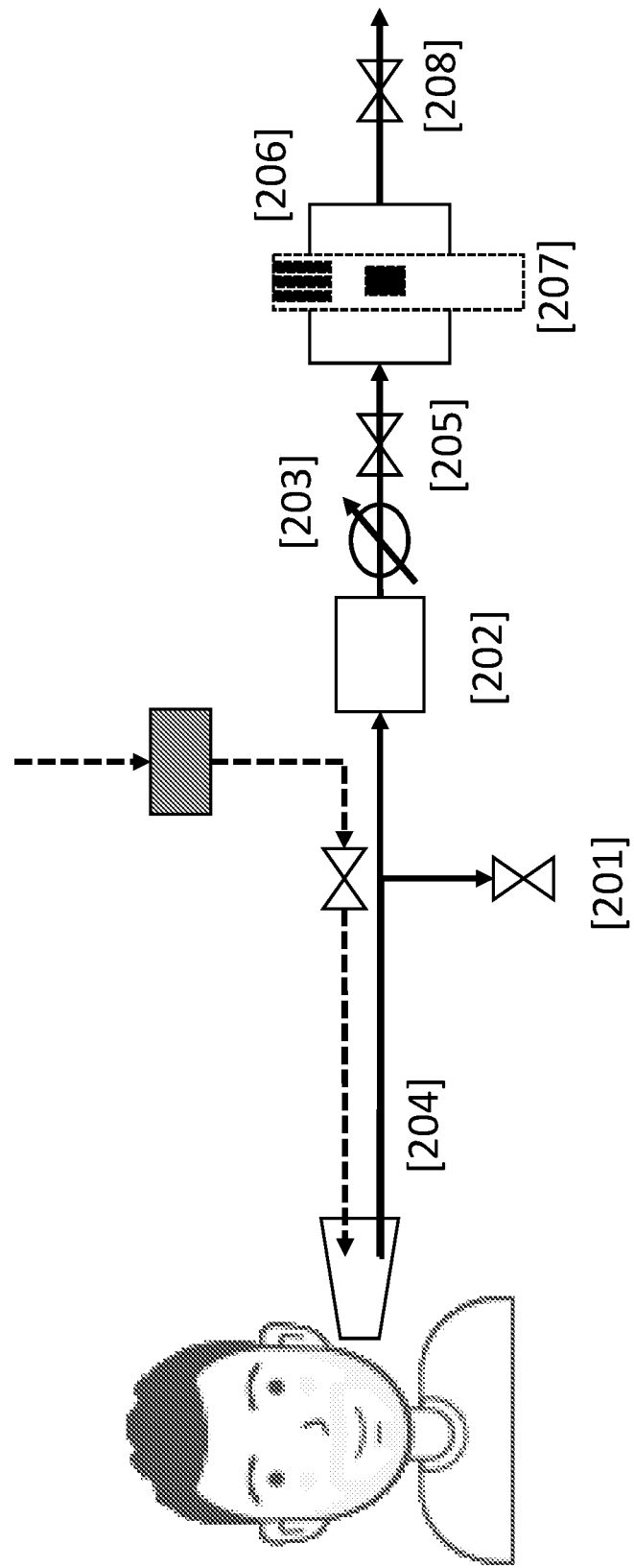
FIG. 2 shows an illustrative example of a system that includes chambers, valves, and a flow rate measurement device according to an embodiment of the invention.

FIG. 2 shows another embodiment [200] of use of a system for measuring an analyte in a gaseous sample in which a diversion valve [201] is disposed between a reaction chamber [202] and a flow rate measurement device [203]. All are in fluid communication with the exhalation fluid flow path of the meter [204]. A second valve [205] is positioned downstream of the reaction chamber [202] and upstream of a test strip [207] and test strip chamber [206]. Another valve [208], which is downstream of the test strip chamber, may be used to trap the analyte or a portion of the analyte in the test strip chamber [206]. Many combinations are possible without deviating from the spirt of the invention. Like the embodiments described in connection with FIG. 1A, the valves can be modulated between open and closed by a controller, or some may open under a set pressure and close when the pressure falls below a threshold. In this way, valves [205] and [208] trap the sample in the test strip chamber [206]

Figure 3:
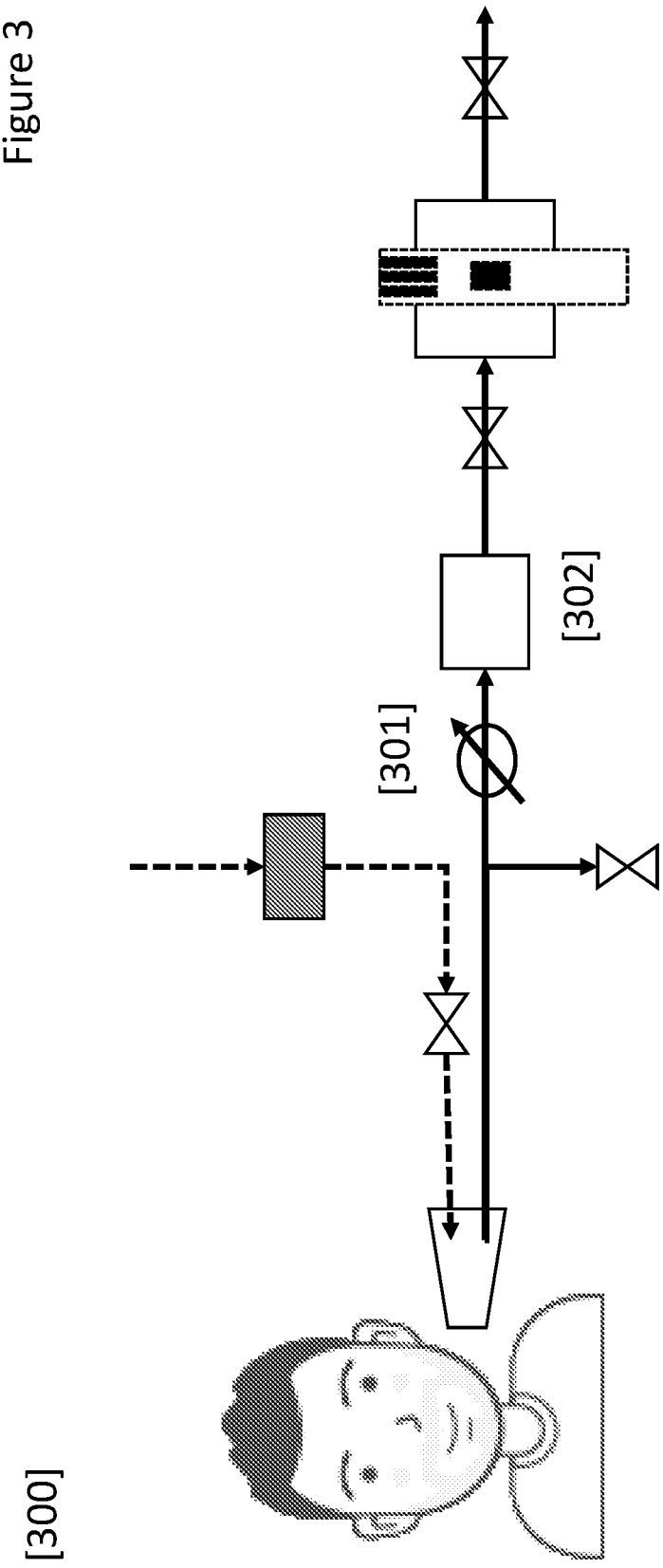
FIG. 3 shows an illustrative example of a system that includes chambers, valves, and flow meter in a different configuration according to an embodiment of the invention.

FIG. 3 shows another embodiment [300] of use of a system for measuring an analyte in a gaseous sample in which a flow measurement device [301] is upstream of the reaction chamber [302]. Flow measurement may be calculated or measured by various types of pressure sensors or flow meters. Examples include but are not limited to rotary flow meters, thermal flow meters, acoustic flow meters, Doppler flow meters, hot wire flow meters, differential pressure sensors, mass flow meters, and pressure sensors all of which are known to those skilled in the art. Many different configurations and numbers of reaction chambers are possible without deviating from the spirit of the invention. The flow rate may be measured in any number of locations without deviating from the spirit of the invention. In one embodiment, the system is configured so that the patient exhales at a flow rate of 50 mL/sec plus or minus 10%.

Figure 4:
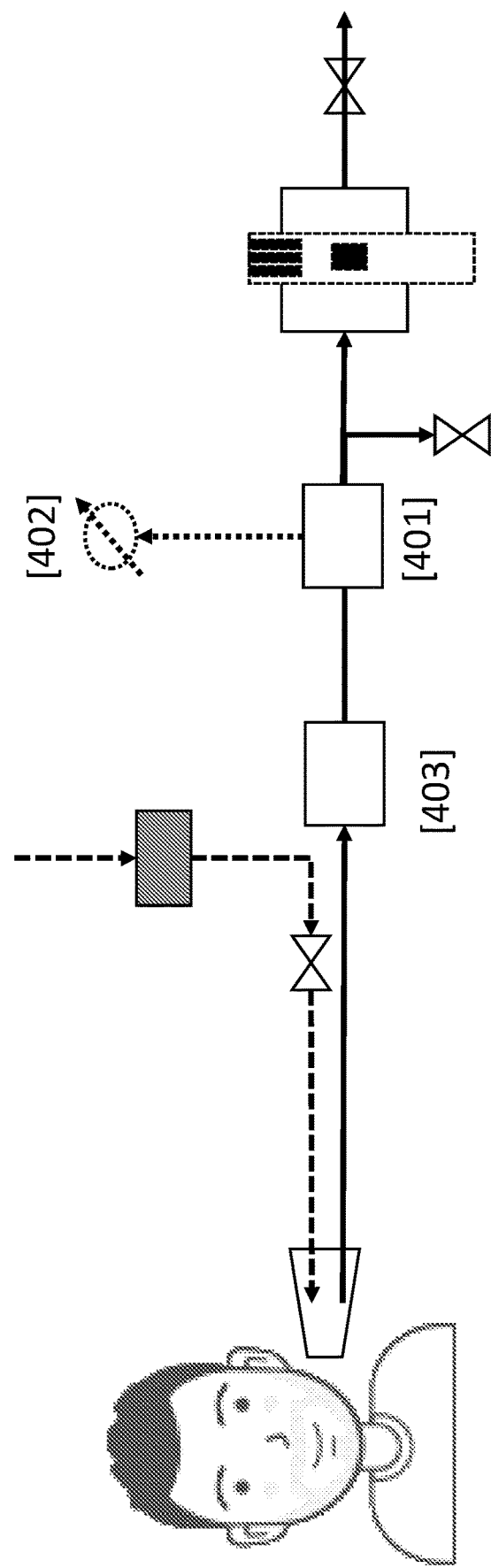
FIG. 4 shows an illustrative example of a system that includes a reaction chamber, a buffer chamber, a chamber for the test strip, valves, and a flow rate measurement device according to an embodiment of the invention.

FIG. 4 shows another embodiment [400] of use of a system for measuring an analyte in a gaseous sample in which the flow rate measurement device [402] is sampled from a buffer chamber [401]. In some embodiments, the buffer chamber [401] is an accumulator for at least a portion of the incoming sample. The buffer chamber [401] can be a static chamber or can be expandable as described in the incorporated applications. Sampling from the buffer chamber may occur by diverting at least a portion of the sample to a pressure sensor or flow meter. The buffer chamber differs from the reaction chamber [403] in that it is inert. The buffer chamber may be placed upstream from or downstream to the reaction chamber. In some embodiments, it may be suitable to have the conversion chamber also serve as a buffer chamber.

Figure 5:
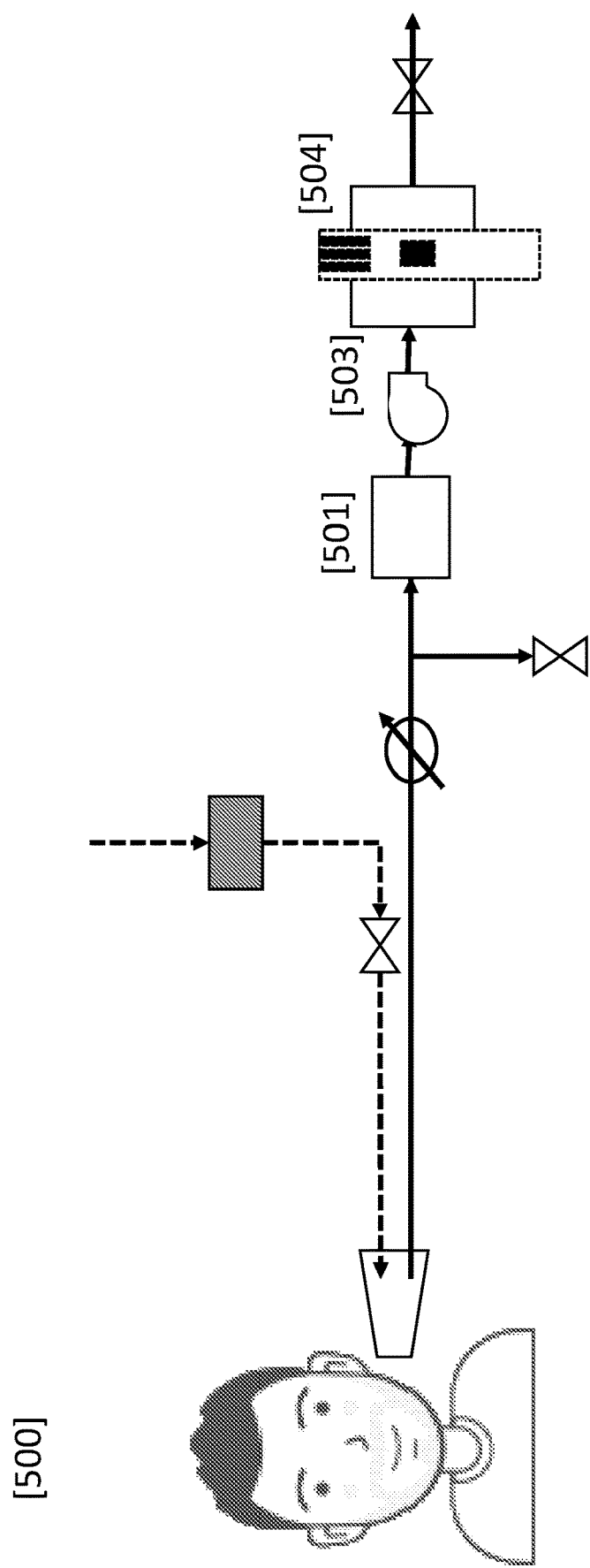
FIG. 5 shows an illustrative example of a system that includes a reaction chamber, a chamber for the test strip, a pump, valves, and a flow rate measurement device according to an embodiment of the invention.

FIG. 5 shows another embodiment [500] of use of a system for measuring an analyte in a gaseous sample in which a pump or blower [503] is in fluid communication with the test strip chamber [504] and at least one other chamber [501]. The pump may be used to control the flow of the sample from one chamber [501] to another [504]. The chamber [501] may be a buffer chamber or a reaction chamber. In another embodiment, a second chamber (not shown) is located upstream to or downstream from chamber [501] so that the two chambers contain at least one buffer chamber and one reaction chamber in fluid communication. In some embodiments, a controller (not shown) controls the pump [503] to provide a set flow rate of sample gas from chamber [501] to the chamber [504].

Figure 6A:
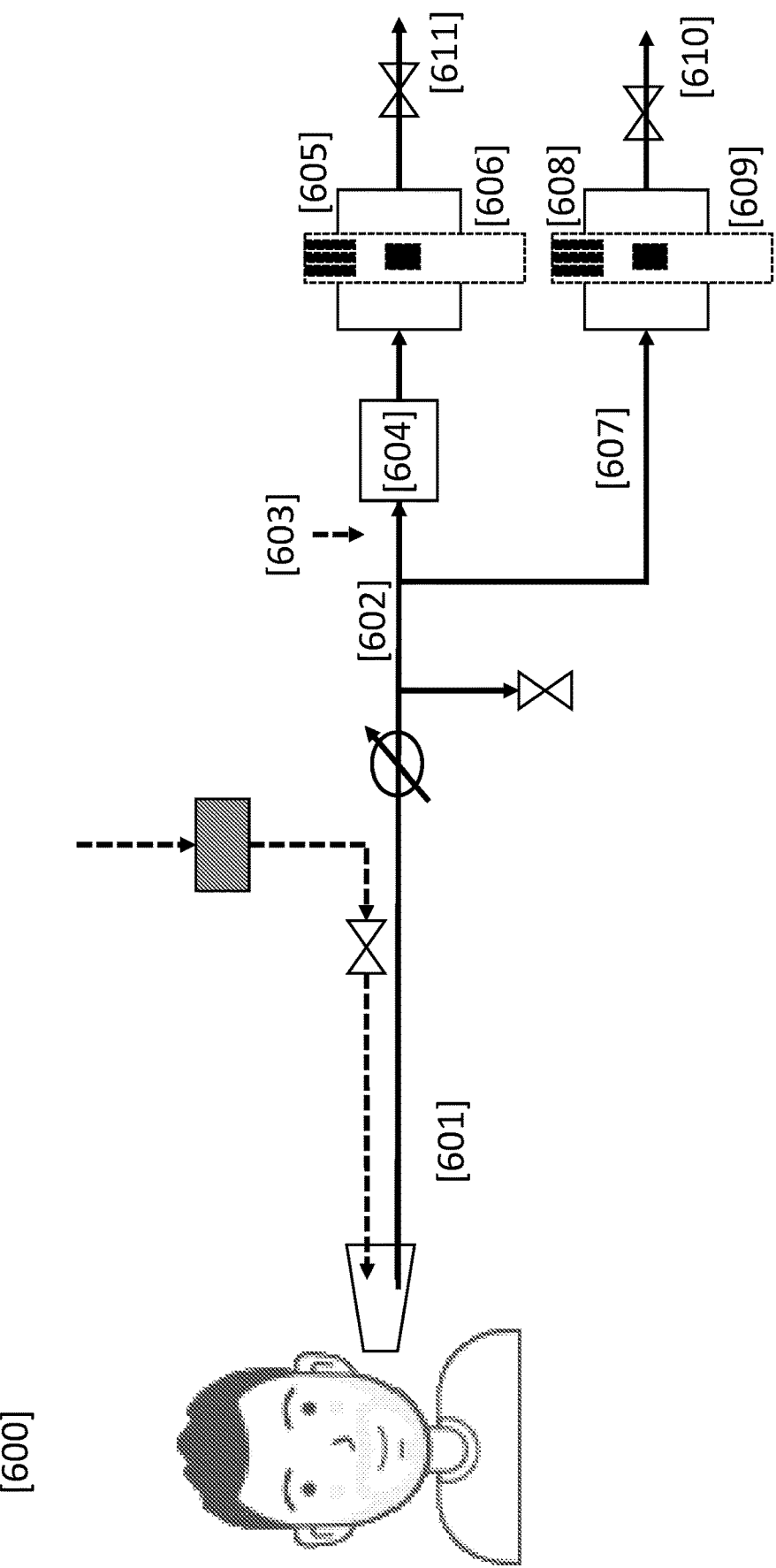
FIGS. 6A and 6B show illustrative examples of systems that include two sample flow paths according to embodiments of the invention.

FIG. 6A shows another embodiment [600] of use of a system for measuring an analyte in a gaseous sample in which a fluid flow path of a meter [601] is divided into more than one stream. In one embodiment, the exhaled stream is bifurcated [602] with one stream [603] passing through a reaction chamber [604] in fluid communication with a first test strip chamber [605] containing a test strip [606] and a second stream [607] in fluid communication with a second test strip chamber [608] containing a second test strip [609]. In one embodiment, the two gas streams exit the meter in separate paths [610] and [611]. In one embodiment, the sensing chemistry present on the two test strips are the same. In another embodiment, sensing chemistry present on the two test strips is different from one another. In some embodiments, the purpose of the second stream [607] is to provide a reference for signal analysis so that test strip [606] is exposed to the converted analyte and second test strip [609] is exposed to the same sample without the converted analyte. In one embodiment, the system is configured to evenly distribute the flow between the two streams. In one embodiment, a buffer chamber (not shown) and pump or pumps (not shown) are used to control the flow through the two chambers. Alternatively, blowers, whether piezoelectric or fan or other type, may be used in place of pumps.

Figure 6B:
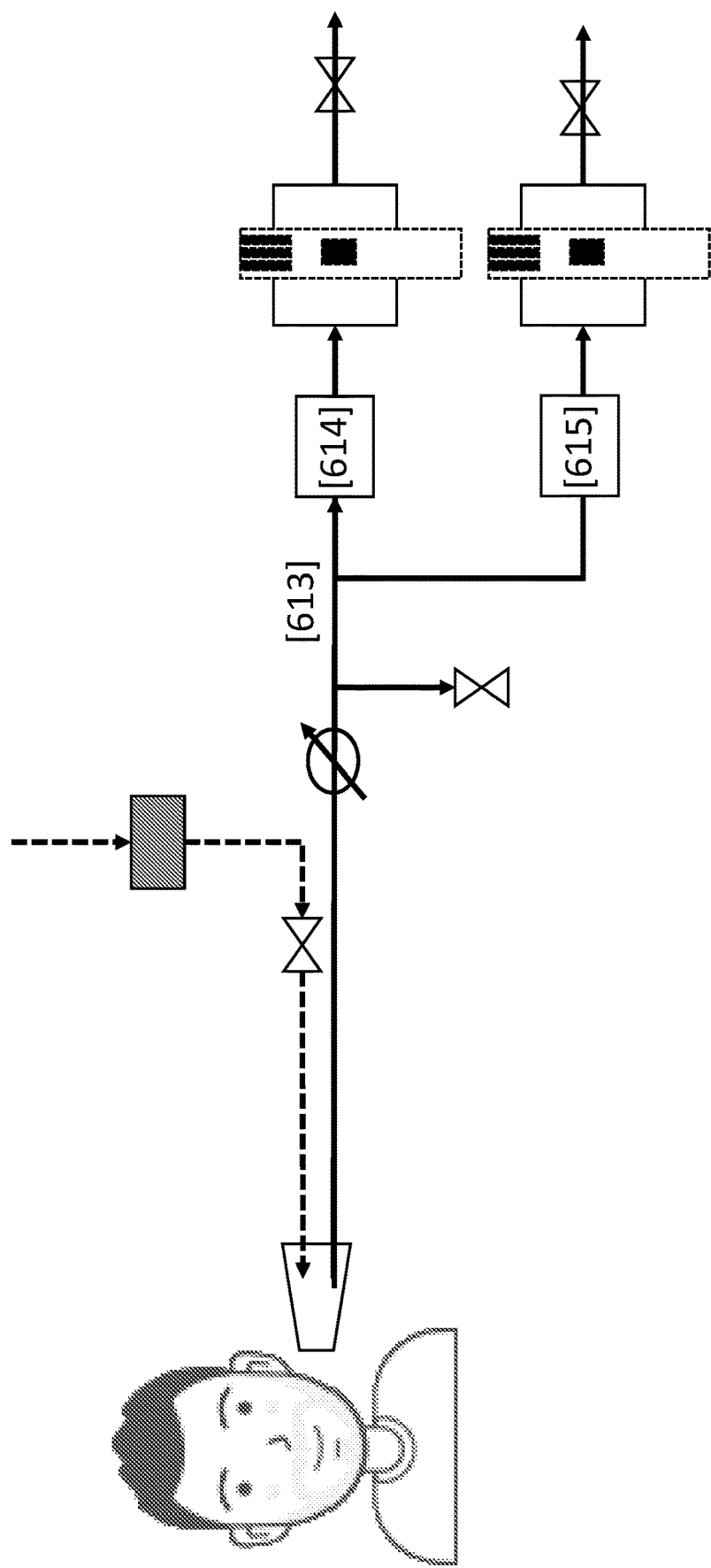

FIG. 6B shows another embodiment [612] of use of a system for measuring an analyte in a gaseous sample which is similar to the use [600] shown in FIG. 6A, except that each branch of the bifurcated stream [613] passes through a separate reaction chamber (chambers [614] and [615], respectively). In some embodiments, the reaction chambers contain the same materials. In other embodiments, the reaction chambers contain different materials. In one example, one chamber [614] contains an oxidizing agent and chamber [615] does not. In one example, reaction chamber [614] may be packed with $KMnO_4$ on silica and reaction chamber [615] may be packed with silica. In some embodiments, the flows to the two streams are controlled as set forth in the examples described in connection with FIG. 6A. In some embodiments, the gaseous sample may be divided into n number of flow paths, in order to flow through n number of reaction chambers, which may or may not contain different materials. In this embodiment, the divided flow paths may flow to n number of sample chambers, or may be recombined or further divided into any number of sample chambers. In this embodiment, the sample chambers may contain the same type of test strips, or may contain different type of test strips, or any combination thereof. One example of a dual flow path device would be a device which measures both hydrogen and methane for lactose intolerance assessment.

Figure 7:
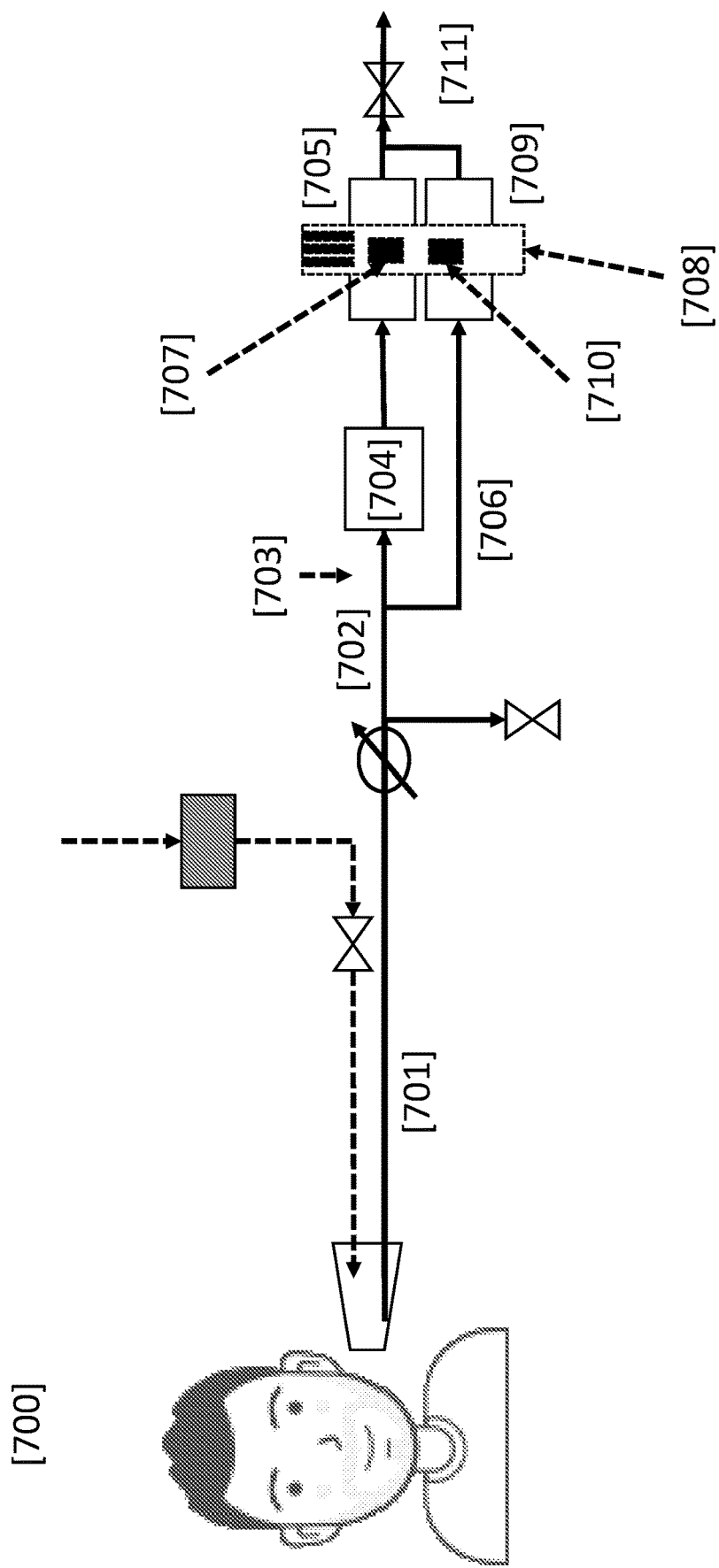
FIG. 7 shows an illustrative example of a system that includes two sample flow paths according to an embodiment of the invention.

FIG. 7 shows another embodiment [700] of use of a system for measuring an analyte in a gaseous sample in which a fluid flow path of the meter [701] is divided into more than one stream. In one embodiment, the exhaled stream is bifurcated [702] with one stream [703] passing through a reaction chamber [704] in fluid communication with a first test strip chamber [705] that exposes the sample of the stream [703] to a first sensing chemistry [707] on a test strip [708]. The second exhaled stream [706] is in fluid communication with a second test strip chamber [709] that exposes the sample of the stream [706] to a second sensing chemistry [710] on the same test strip [708]. In some embodiments, the sensing chemistries are the identical. In other embodiments, the sensing chemistries are different. In some embodiments, the sample re-joined [711] and pass out of the meter. In some embodiments, the gaseous sample may be divided into n number of flow paths, in order to flow through n number of reaction chambers, which may or may not contain different materials. Examples of the fluid sample passing through multiple reaction chambers as described earlier are possible without deviating from the spirit of the invention. Techniques for controlling the flows to either or both streams include any described herein for two stream or single stream embodiments.

Figure 8:
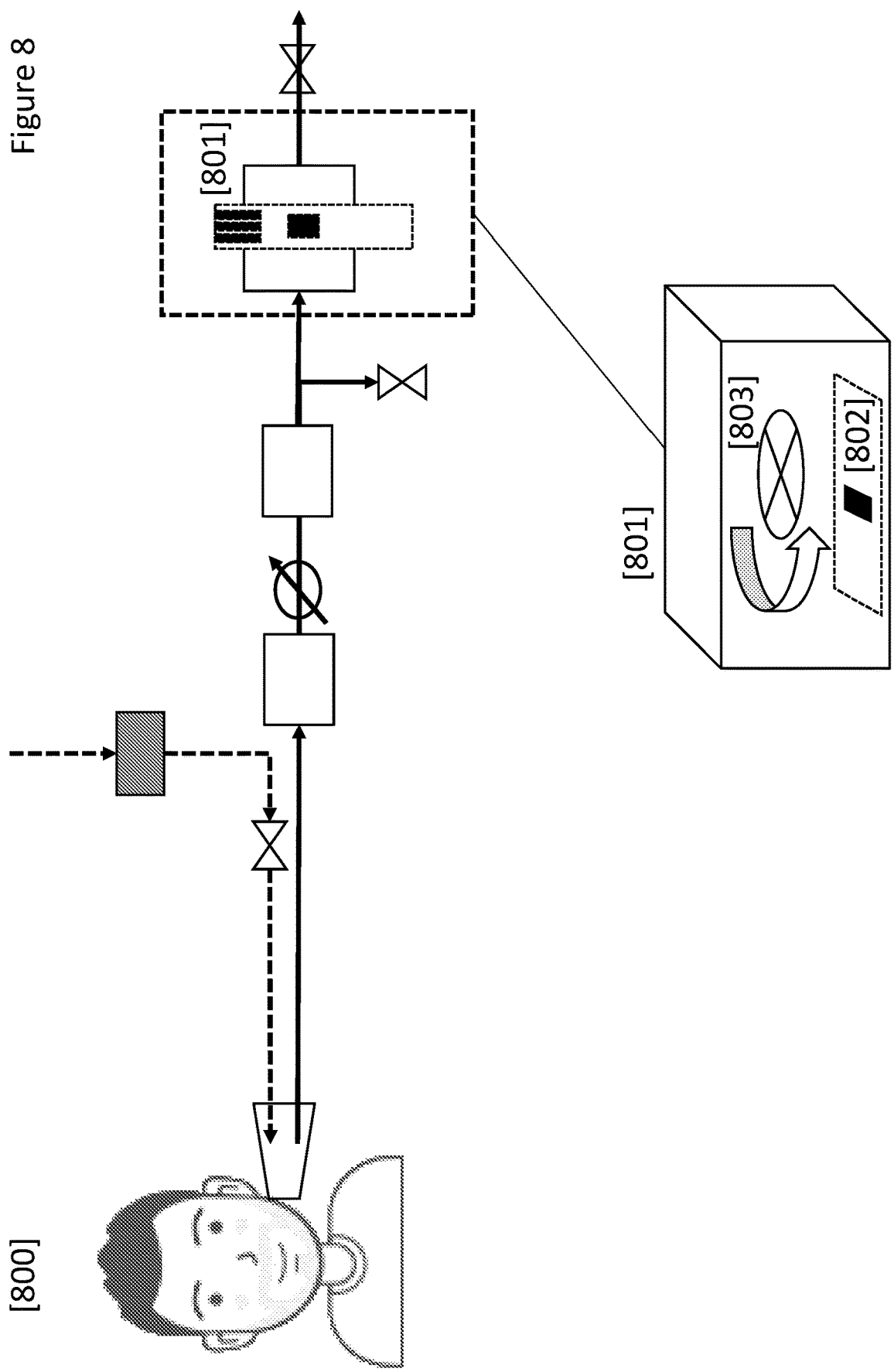
FIG. 8 shows an illustrative example of a reaction chamber that includes a test strip chamber that contains an analyte circulator and/or agitator according to an embodiment of the invention.

FIG. 8 shows another embodiment [800] of use of a system for measuring an analyte in a gaseous sample in which a chamber [801] containing a test strip [802] contains a computer controlled, motorized device for circulating, re-circulating, disrupting, agitating or exciting or otherwise altering the energetic or magnetic state of the gas sample [803]. Numerous methods are possible without deviating from the spirit of the invention. Examples include but are not limited to a fan, a source of ultraviolet (UV) energy, a source of radio frequency (RF) energy, a magnetic source, a heater, a cooler, a pump, an auger, a whisk, blades, blower, piezoelectric fan or blower etc. Any combination is possible without deviating from the spirit of the invention (including more than one of the same item). In one embodiment, the device [803] speeds up the measurement time. In another embodiment, the test strip [802] consumes or irreversibly binds to the analyte of interest and the device [803] is configured to ensure the test strip [802] is exposed to the entire sample that is contained or trapped in the test strip chamber [801]. In another embodiment, the device provides sufficient energy to allow the analyte to react. In another embodiment, the device changes the chemical state of the analyte to alter the reactivity of the analyte with the test strip.

Figure 9:
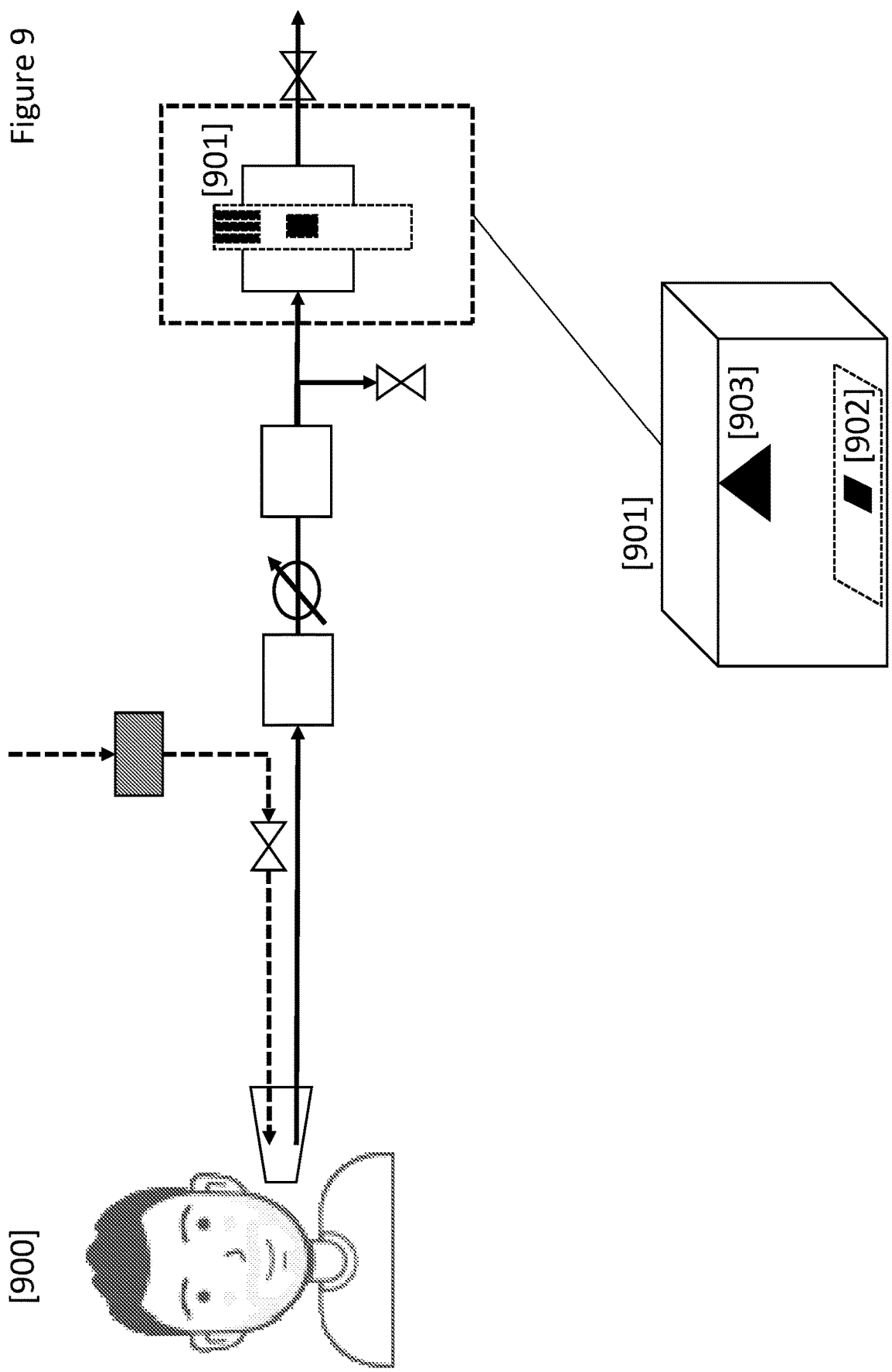
FIG. 9 shows an illustrative example of a system that includes a test strip chamber that contains an energy source or magnetic field according to embodiments of the invention.

FIG. 9 shows another embodiment [900] of use of a system for measuring an analyte in a gaseous sample in which a chamber [901] containing the test strip [902] contains an energy source [903]. In one embodiment, the energy source is used to clean the sensor. In one embodiment, the energy source is a source of UV or RF. Cleaning the sensor may be for the purpose of removing chemical species from the surface or to stabilize a baseline measurement or for calibration or analyte measurement. In another embodiment, the energy source is used to alter the sample. In one embodiment, this may be achieved by applying current or voltage at a steady or variable rate. Embodiments including one or more energy sources can be used in conjunction with the embodiments and techniques disclosed in the incorporated applications.

Figure 10:
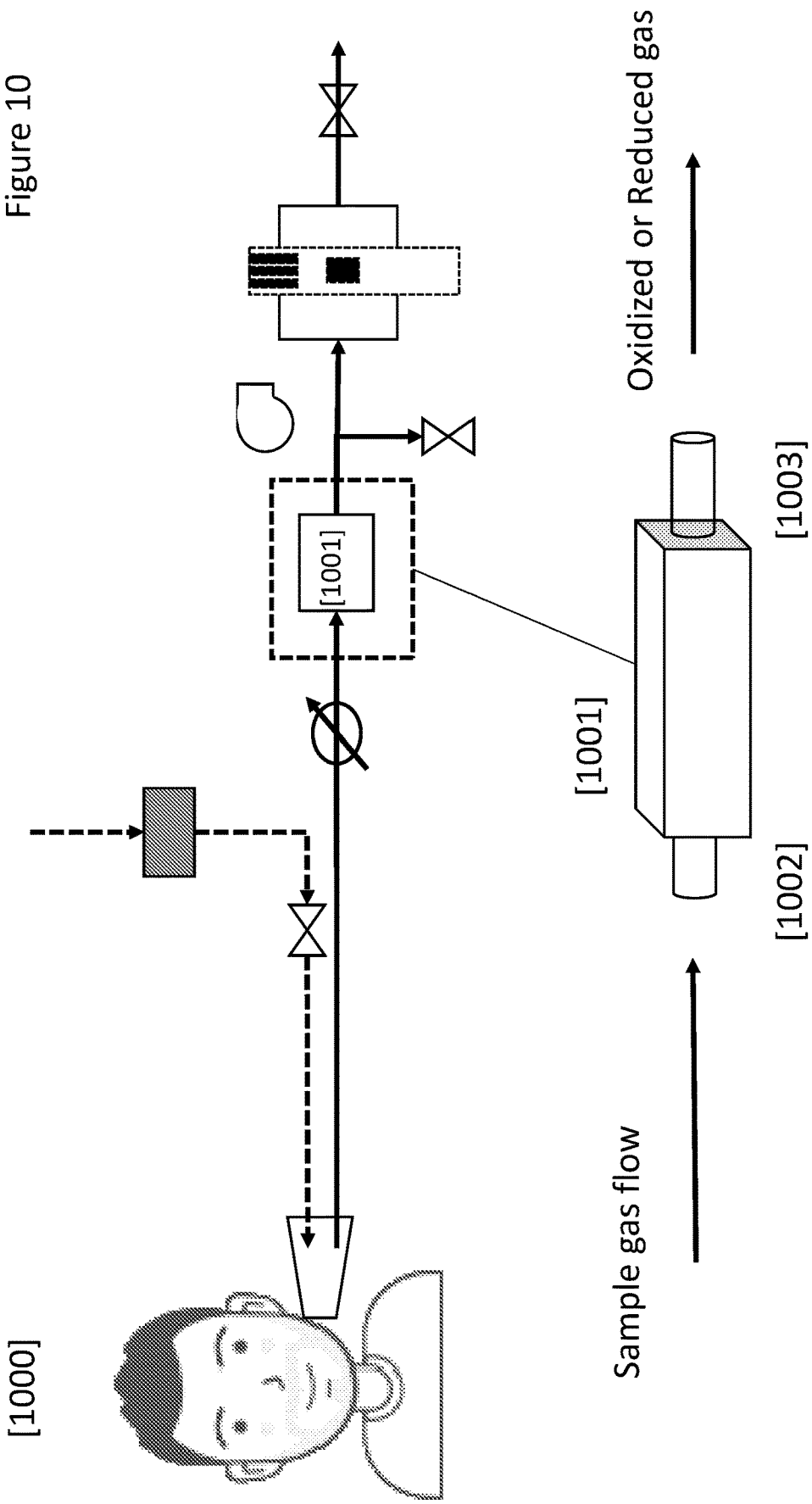
FIG. 10 shows an illustrative example of a reaction chamber/cartridge according to embodiments of the invention

FIG. 10 shows another embodiment [1000] of use of a system for measuring an analyte in a gaseous sample in which a reaction chamber [1001] contains a sample inlet [1002] and a sample outlet [1003]. The sample is passed through the reaction chamber to alter and/or fundamentally change the physical, chemical, or electrochemical properties of the sample. Examples include but are not limited to oxidation, reduction, ion exchange reactions, coordination reactions, oligomerization, condensation from the gaseous or liquid phases, volatilization from a solid or liquid phase, dissolution into a carrier gas or liquid, adsorption onto a secondary component, formation of high energy molecular states (such as stimulation via electromagnetic radiation), molecular polarization of the analyte(s) (such as through the use of magnetic fields), ionization of the analytes (such as through the use of electromagnetic radiation, or electron or particle bombardment, or other methods know to those in the field), etc. In another embodiment, the reaction chamber is designed to heat the sample. In another embodiment, the reaction chamber is designed to alter the chemical make-up of the sample and heat the sample. In one embodiment, the reaction chamber is configured to convert NO to $NO_2$. Oxidation may occur by any number of methods without deviating from the spirit of the invention. In another body, the reaction chamber also dehumidifies the sample stream. In some embodiments, the reaction chamber (FIGS. 10, 11, and 12) and the sample chamber (e.g. FIG. 8) may be the same chamber. Sample chamber and test strip chamber are used interchangeable and refer to the same structure.

Figure 11:
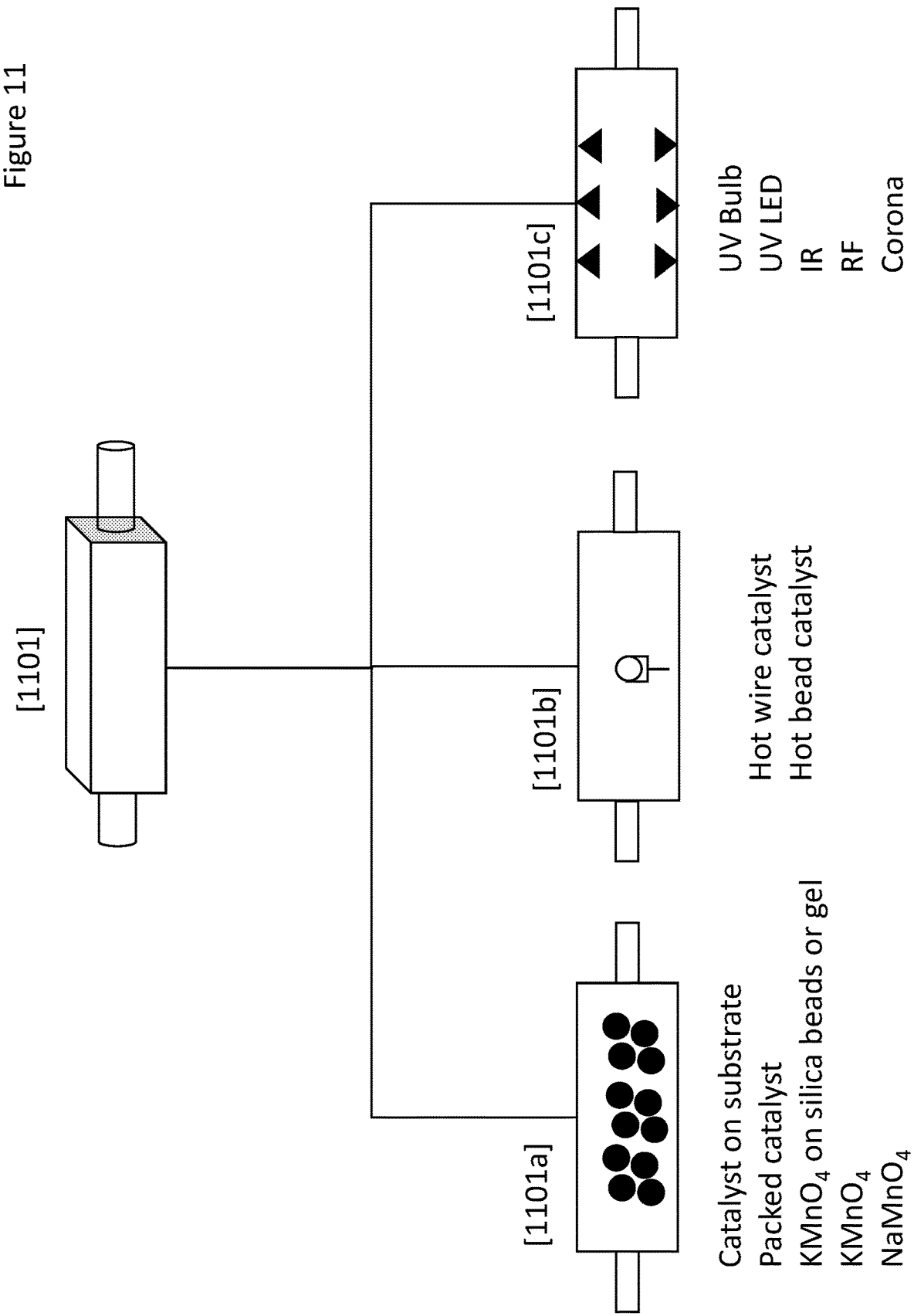
FIG. 11 shows illustrative examples of disposable reaction chamber/cartridge configurations according to embodiments of the invention.

FIG. 11 shows various embodiments of reaction chambers [1101], [1101a], [1101b], [1101c] and potential methods for oxidation. In one embodiment, a reaction chamber [1101a] contains a catalyst to alter the chemical properties of the sample. In another embodiment, a substrate in the reaction chamber [1101a] has been functionalized with a catalyst. In one embodiment, the catalyst is an oxidizer. In one embodiment, the reaction chamber contains sodium or potassium permanganate as the catalyst. In another embodiment, the potassium permanganate is on a silica substrate. In another embodiment, the potassium permanganate is on an activated alumina substrate. In another embodiment, a catalyst is impregnated on a porous substrate. The reaction chamber may also include a device to contain the catalyst. In one embodiment a filter, mesh or metal mesh prevents the catalyst from escaping the inlet or outlet port during an inhalation/exhalation by the patient. In another embodiment, a reaction chamber [1101b] contains a hot wire or bead catalyst. In another embodiment, a reaction chamber [1101c] includes a computer controlled energy source to apply energy to the sample as it passes through the chamber. Examples include but are not limited to UV, UV LED, UV Bulb, infrared (IR), RF, corona discharge, etc. In one embodiment, energy is used to produce ozone and oxidize NO to $NO_2$. Various methods of ozone production are possible without deviating from the spirit of the invention.

FIG. 12 shows various configurations of reaction chambers [1200], [1202], [1204], [1205], [1206]. In one embodiment, the reaction chambers are disposable cartridges with a limited life. In another embodiment, the cartridge may also include a device for managing or controlling the number of uses (not shown). Examples include RFID, barcodes, circuit or fuse burn out, memory on cartridge, etc. In one example, the life of the cartridge is designed to match the number of sensors sold in a package. In each of these embodiments, the cartridge is configured to enable the fluid sample to enter and exit. In another embodiment, the reaction chamber is part of the sample chamber. In one embodiment, the conversation/reaction chamber contains its own calibration which may be accepted by the meter by at least one of optical, digital or physical signal.

Figure 13:
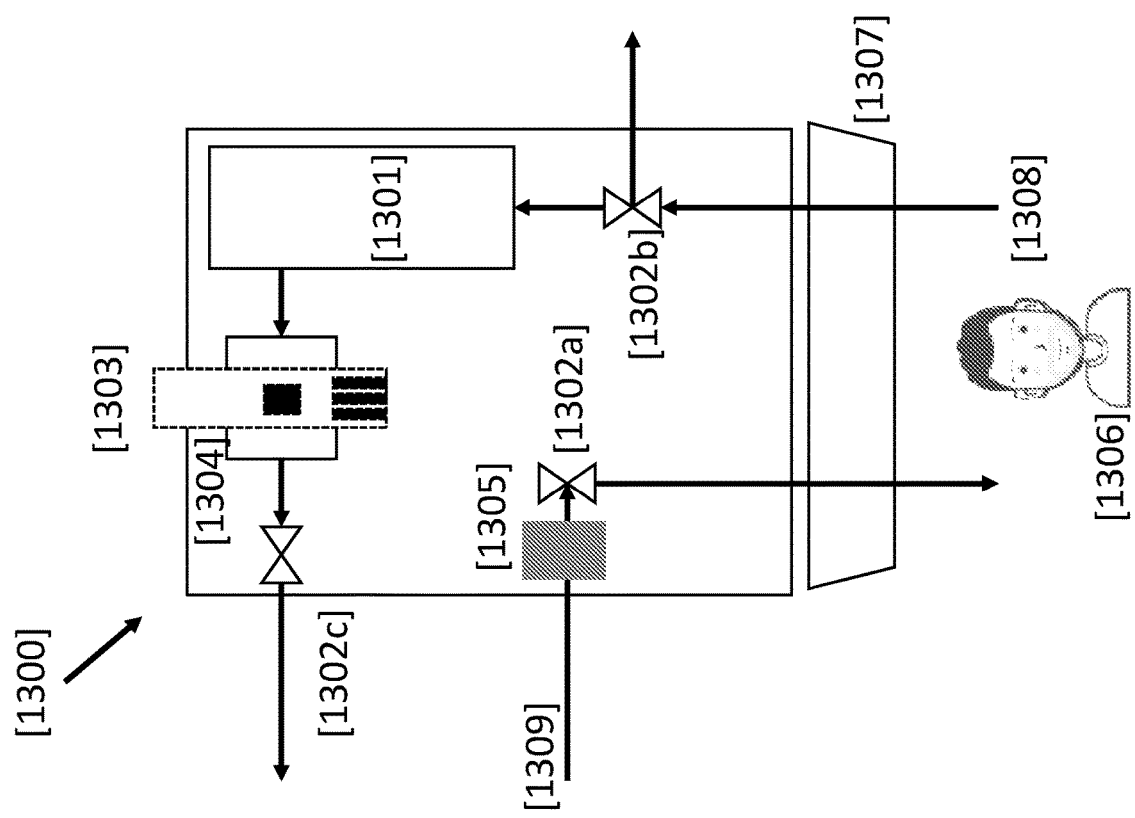
FIG. 13 shows an illustrative example of a compact configuration of a system with a removable and/or disposable test strip and reaction chamber/cartridge according to an embodiment of the invention.

FIG. 13 demonstrates a compact design for a system for measuring an analyte in a gaseous sample according to one embodiment of the invention. A device [1300] contains a reaction chamber [1301], multiple valves [1302a], [1302b], [1302c] a test strip [1303] and test strip chamber [1304] and a filter [1305] to remove chemical species from ambient air. In this embodiment [1300] the patient [1306] inhales through a mouth piece [1307] drawing ambient air [1309] through a filter [1305] and one-way, mechanical valve [1302a]. The patient exhales [1308] through the mouth piece [1307] and through a computer controlled solenoid valve [1302b] and the sample is dumped to ambient air. The exhalation flow rate is measured as previously described (not show in this embodiment). In one embodiment, the flow rate is 50 ml/sec plus or minus 10%. In one embodiment, the pressure is between 5-20 cm $H_2O$. After a pre-determined period of time (e.g. <7 seconds) the valve [1302b] is closed to ambient and the flow is directed to a reaction chamber [1301] containing a material to oxidize the NO in the sample to $NO_2$. The oxidized sample passes through the test strip chamber [1304] and exits the device through valve [1302c]. Valve [1302c] may be a one-way mechanical valve or a computer controlled solenoid valve. In the case of a solenoid valve, the beginning position may be open or closed but the valve [1302c] is in the open position when valve [1302b] directs flow to the reaction chamber [1301].

Measurements from the test strip may be taken continuously or at any point or points in the measurement. In one embodiment, valves [1302b] and [1302c] close after 10 seconds trapping a portion of the sample in the test strip chamber [1304]. Valve [1302c] may be closed electronically, as is the case of a solenoid valve, or mechanically due to a pressure drop, as is the case with a one-way mechanical valve. Alternatively, valve [1302b] may be placed downstream from reaction chamber [1301] and upstream from the test strip chamber [1304]. Alternatively, a buffer chamber (not shown) may be placed upstream from or downstream to the reaction chamber.

Figure 14B:
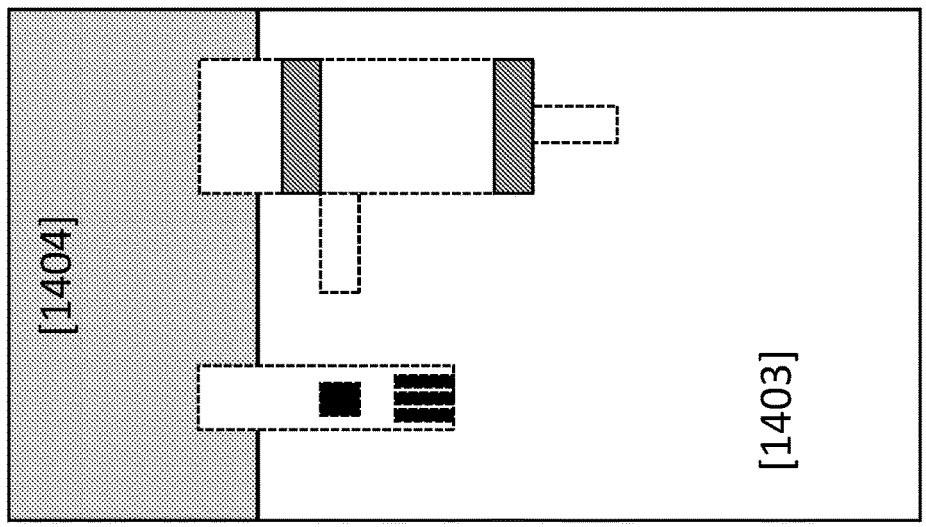
FIGS. 14A and 14B show an illustrative example of a device with a removable test strip and a reaction chamber/cartridge according to embodiments of the invention.
Figure 14A:
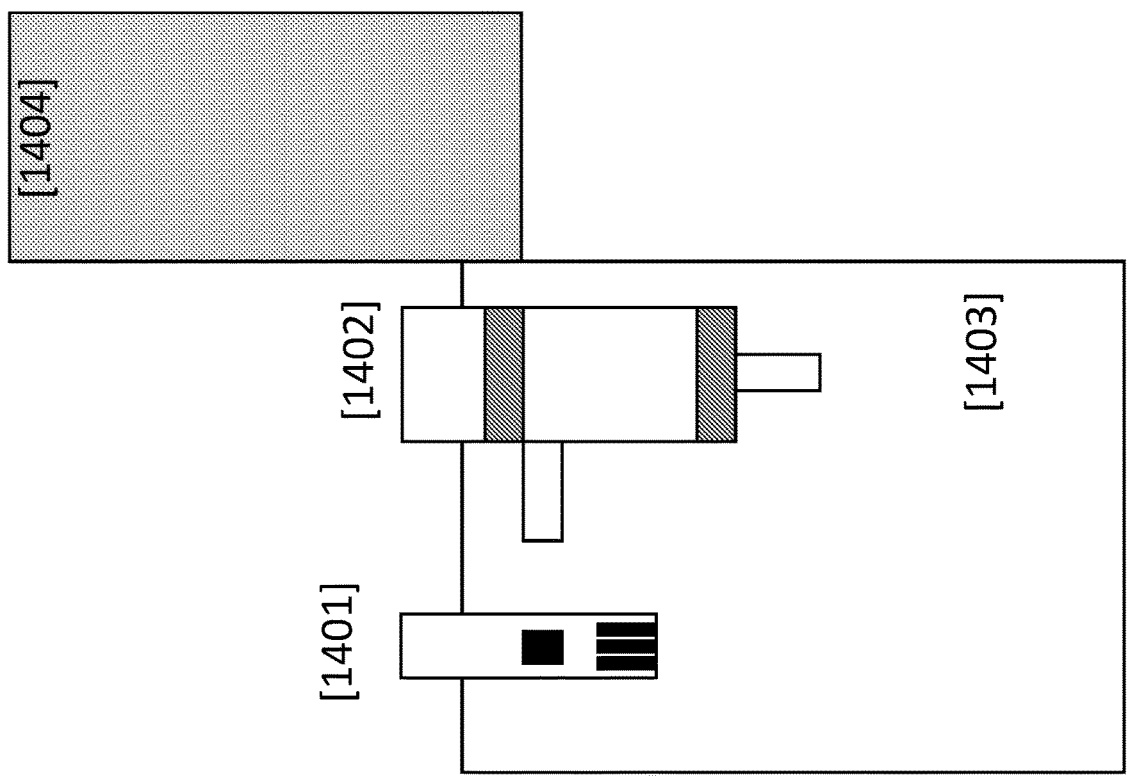

FIGS. 14A and 14B show a device [1403] for measuring an analyte in a gaseous sample. The device [1403] contains a removable test strip [1401] and reaction chamber/cartridge [1402]. The device [1403] also has a cover [1404] that covers and seals the test strip [1401] and reaction chamber/cartridge [1402] into the device [1403]. FIG. 14A illustrates the cover [1404] in an open configuration, while FIG. 14B shows the cover [1404] in a closed configuration. The cover [1404] can be attached to the device [1403] via a hinge or other known techniques. The internal workings are described in earlier embodiments (e.g. [1300])

Figure 15B:
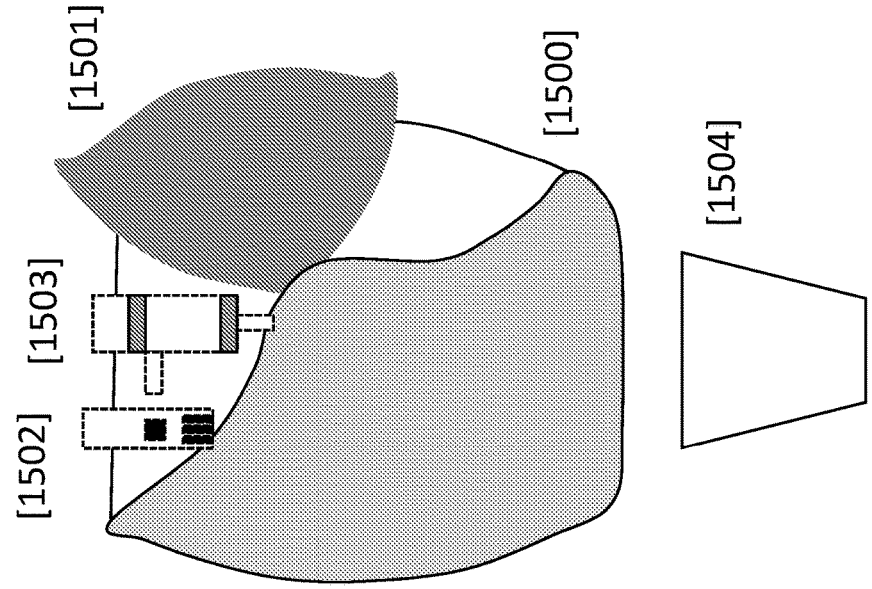
FIGS. 15A and 15B show an illustrative example of a device with a removable test strip and reaction chamber/cartridge configuration with a mouth piece according to an embodiment of the invention.
Figure 15A:
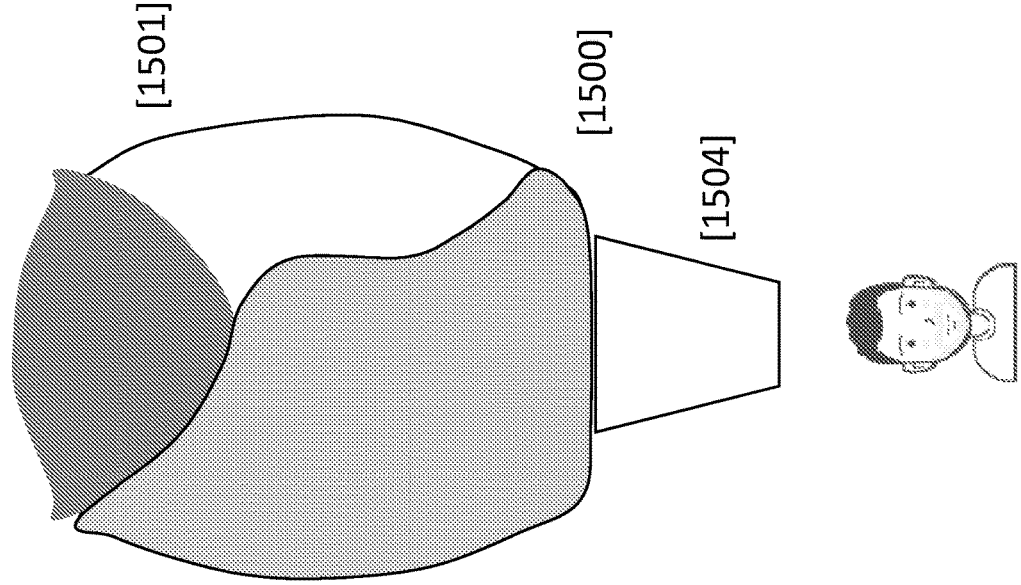

FIGS. 15A and 15B show an embodiment of a device [1500] that includes a hinged top [1501] to seal the test strip [1502] and reaction chamber/cartridge [1503] into the device [1500]. In this embodiment, a separate mouth piece [1504] also connects to the device [1500]. FIG. 15A illustrates the cover [1501] in a closed configuration with the mouthpiece [1504] in place, while FIG. 15B shows the cover [1501] in an open configuration with the mouthpiece [1504] removed.

In some embodiments of the invention the output of the device is selected from a plurality of endpoints. In one embodiment, the measurement of resistance or voltage corresponds to at least one of a plurality of analyte concentration ranges. In one embodiment, the outputs are quantitative or semi quantitative. In another embodiment, the outputs are qualitative. In yet another embodiment, the endpoints may be determined from the age of the patient. The endpoint for an age less than 12 correlates to three ranges of analyte concentrations (i) less than 20 parts per billion, (ii) between 20 and 35 parts per billion, (iii) greater than 35 parts per billion of the analyte. The endpoint for an age greater than 12 correlates to three ranges of analyte concentrations (i) less than 25 parts per billion, (ii) between 25 and 50 parts per billion, (iii) greater than 50 parts per billion of the analyte. In another embodiment, the device may determine the type of output based on the input received from one or a plurality of sources. In some embodiments, the output is above or below a pre-determined analyte concentration. In some embodiments, the pre-set analyte concentration is selected from a range of concentrations between 1 and 50 parts per billion. When the analyte is nitric oxide the pre-set analyte concentration may preferably be 20 parts per billion, 25 parts per billion, 30 parts per billion, 35 parts per billion, 40 parts per billion, 50 parts per billion. When the analyte is methane the preferable pre-set analyte concentration is 15 parts per million or 20 part per million. When the analyte is hydrogen the preferable pre-set analyte concentration is 15 parts per million or 20 part per million.

Test Strip—General: At its most basic level, the test strip is comprised of a substrate/base and sensing chemistry. Embodiments of the test strip include a substrate, a means of establishing an electrical connection (i.e. electrode), at least one sensing chemistry and optionally at least one additional layer. The configuration and design may be modified based on the gas of interest and environment in which the test strip will be placed. The sensing chemistry is selected based on the gas of interest, and the electrodes are configured to measure the change of properties of the sensing chemistry that occurs during the interaction with the analyte. The layer, or layers, may serve multiple purposes including, but not limited to, support for the sensing materials and chemistry, sensing the analyte, masking for chemistry deposition, adhesion between layers, protection from interfering substances, enhancing the selectivity and/or sensitivity of the test strip, protecting the sensing chemistry and spacing. Layers may include features such as windows or holes to enable at least a portion of the fluid sample to pass through. Details regarding the electrode, the chemistry, and the layers are described below.

In some embodiments the test strip is single use. In some embodiments, the test strip is multi use. In some embodiments, the test strip is limited use. In still other embodiments the test strip can be used for less than or equal to three uses.

In one embodiment, the test strip may contain electrodes in a specific configuration or of a specific resistance indicating to the device the type of output to display. In another embodiment, a bar code is used to determine the type of output to display. The bar code may be located in any number of places without deviating from the spirit of the invention. Examples include but are not limited to the test strip or packaging. In another embodiment, a chip is inserted into the device to provide information regarding the at least one of a plurality of outputs. In another embodiment, the type of output is manually entered into the device.

In another embodiment, the bar code or chip may also enable the device to utilize a specific calibration table. In another embodiment, the bar code or chip may contain information pertaining to a calibration table.

In another embodiment, information regarding the plurality of outputs or information regarding calibration is received from a paired mobile computing device.

Test Strip Sensing Chemistry: Many sensing chemistries are possible without deviating from the spirit of the invention. In one embodiment, the sensing chemistry is comprised of nanostructures functionalized to bind to an analyte causing an electrical resistance change across the nanostructures. In other embodiments, the analyte causes a redox reaction at the sensor surface which is measured. In another embodiment, the analyte causes a change in the electron environment of the sensing chemistry, resulting in changes in the optical characteristics, which are measured. Nanostructures may include, but are not limited to, carbon nanotubes (single walled, multiwalled, or few-walled), graphene, graphene oxides, nanowires etc. The nanostructures can be assembled to form macroscopic features, such as papers, foams, films, etc. or may be embedded in or deposited on macrostructures. Examples of functionalization materials include:

Heterocyclic macrocycles
  i. Examples include but are not limited to: crown ethers, phthalocyanines, porphyrins etc.

Metal oxides
  ii. Examples include but are not limited to: $AgO$, $CeO_2$, $Co_2O_3$, $CrO_2$, $PdO$, $RuO_2$, $TiO_2$ Transition metals
  iii. Examples include but are not limited to: Ag, Cu, Co, Cr, Fe, Ni, Pt, Ru, Rh, Ti Carbonyl groups
  iv. Examples include but are not limited to: Carboxylic acids, Amides, Aldehydes, etc Functional Organic Dyes
  v. Examples include but are not limited to: Azo dyes, Cyanines, Fluorones, indigo dyes, photochromic dyes, Phthalocyanines, Xanthens, etc.

The functionalized nanostructure, herein referred to as sensing chemistry, is disposed over a substrate to form the basic components of a test strip. Electrodes are in communication with the sensing chemistry as described below.

Sensing chemistry means a compound or set of compounds that change some physical property when exposed to an analyte. The physical property may be transduced into an electrical signal and measure as at least one of a resistance, a voltage, or a current. The sensing chemistry may be active, meaning designed to respond to the analyte or analytes of interest or a reference sensing chemistry. A reference sensing chemistry is a compound or set of compounds that is either protected from interaction with at least one analyte or not responsive to at least the analyte of interest.

In another embodiment, the sensing chemistry is a non-functionalized (i.e. un-sensitized) nanostructure. This embodiment may be used in conjunction with a functionalized nanostructure or it may stand-alone.

Secondary additives may be used to affect the drying characteristics and process ability of the sensing chemistry for deposition onto a substrate. Non-limiting examples of deposition methods are listed in FIG. 16. Additives may be used to change the viscosity, surface tension, wettability, adhesion, drying time, gelation, film uniformity, etc. These additives include, but are not limited to, secondary solvents, thickeners, salts, and/or surfactants. These additives may serve one or multiple purposes. Examples may include, but are not limited to, those in FIG. 16 and:

i. Thickeners—polymeric and non-polymeric
    1. Glycerol
    2. Polypropylene glycol
  ii. Surfactants—ionic and non-ionic
    3. Sodium dodecyl sulfate
    4. Triton X-100

In some embodiments, the volume of sensing chemistry disposed on the substrate may be less than or equal to 1 milliliter of material.

In some embodiments the sensing chemistry irreversibly binds to the analyte of interest under the specified conditions for measurement. Examples of irreversible interactions include, but are not limited to, covalent bonding, ion-ion interaction, or non-covalent interactions with large equilibrium constants, such as coordination bonds, dipole-dipole interactions, ion exchange reactions, or hydrogen bonded networks. As used herein, a bond is considered irreversible if there is little to no signal recovery over a relevant time scale within a relevant range of operating conditions after the sensor stops being exposed to the analyte (i.e. the partition coefficient is <0.5). Upon further exposure to new analyte, it is expected that the sensor retains a degree of sensitivity. In some embodiments, the range of conditions include that which the sensor is exposed to during normal operations, e.g. normal operating levels of temperature, pressure, humidity, light exposure etc. With regard to relevant time scales, ideally, an irreversible system never recovers 100% back to the original baseline. In one implementation, a sensor recovers less than 10% in twice the sensing time after the sensor is no longer exposed to the analyte. Thus, if the sensing time is 3 days the sensor signal for an irreversible binding system would decrease by less than 10% in 6 days after the sensor is no longer exposed to the analyte and never fully recover to its original baseline. Likewise, if the sensing time is 10 seconds, the signal would decrease by less than 10% in 20 seconds following removal from the analyte and never fully recover to its original baseline. Another way to express irreversible binding is that the binding never reaches a steady state equilibrium up until the point where the number of binding sites has been saturated by the analyte. Rather, analyte accumulates on the sensor with each additional exposure.

In some embodiments, an analyte is considered irreversibly bound to the sensing chemistry when the fraction of bound molecules leaving the sensor surface is, for example less than 0.5. This fraction is referred to herein as the partition coefficient. The partition coefficient is defined as the proportion of bound analyte molecules leaving the sensor surface after exposure to the analyte is removed at the application use temperature. In one embodiment, the partition coefficient is less than 0.5. In another embodiment, the partition coefficient is less than 0.25. In another embodiment, the partition coefficient is less than 0.1. In another embodiment, the partition coefficient is less than 0.05. In yet another embodiment, the partition coefficient is less than 0.01.

Due to the irreversible nature of the chemistry, in some embodiments, each time a test strip is used most of the analyte from the previous measurement remains on the test strip. Thus, prior to each measurement a baseline measurement is taken. In some embodiments, the initial baseline is also taken at the point of care or point of use because ambient conditions such as temperature, humidity, and pressure can influence some types of measurements. Following the baseline measurement, the sensor is exposed to the analyte and a measurement is taken. The signal may be measured either as an absolute or relative change as compared to the baseline.

In some embodiments, the test strip is single use, meaning the sensing chemistry is saturated after a single exposure to the analyte. In some embodiments, the test strip is multiple use, meaning the sensing chemistry is not saturated after a single exposure to the analyte. Instead, the sensing chemistry accumulates analyte with each exposure, and does not become saturated until it has been subjected to multiple exposures. In some embodiments, the analyte saturates the sensing chemistry after 365 exposures to the analyte. In some embodiments, the analyte saturates the sensing chemistry after 52 exposures to the analyte. In some embodiments, the analyte saturates the sensing chemistry after 12 exposures to the analyte.

Test Strip—Substrate, Electrode, Sensing Chemistry Configuration and Layers:

Various configurations or combinations of the substrate, electrode, and chemistry deposition are possible without deviating from the spirit of the invention. Configurations are dictated by the characteristics of the sensing chemistry, analyte of interest, and the environment in which the unit will be placed. Sensing chemistries may also be coated or covered to prevent specific interactions (such as those with the analyte), so as to provide a reference, as in a chemresistive bridge circuit. Multiple sensing chemistries may be used, or the same chemistry may be deposited more than once, to serve as a reference, for multiplexed analysis, or for signal averaging. FIG. 17A shows examples of various configurations of substrate, electrode, sensing chemistries and layers of the test strip. In one embodiment [1709], the test strip consists of a base substrate [1701], at least one electrode pair [1702] and at least one sensing chemistry [1703] in electrical communication with the electrode pair [1702] and optionally an additional layer [1704] with a window or holes [1705] to expose at least the sensing chemistry when assembled [1707]. The additional layer [1704] may serve as a spacing or a protective layer. Optionally the test strip may contain a second sensing chemistry [1706]. Optionally, the test strip may not contain a second layer [1708]. Additional layers may be incorporated into the test strip for a variety of reasons depending on the sensing chemistry, electrode configuration, interfering substances and manufacturing process. Examples include but are not limited to: masking for chemistry deposition, support for chemistry deposition, protection from interfering substances, enhancing the selectivity and/or sensitivity of the test strip, acting as the sensing chemistry, spacing, protection of the sensing chemistry, formation of gas chamber(s), test strip rigidity or structural configuration. Layers may be comprised of porous and non-porous polymers, composite materials, fibrous materials such as paper or fiber glass, woven and non-woven textiles, membranes, polymers, adhesives, films, gels, etc. The layers may be modified, for example, in some embodiments, by chemically treating or coating and/or mechanically altering. The layers may serve one, or more than one, purpose. For example, in some embodiments, a layer may serve as a structural component (e.g. improve rigidity or as a spacer), and a selective gas permeable membrane. In another example, a layer may serve as a structural component (e.g. a spacer or protective layer) and further define a window to enable the analyte of interest to reach the sensing and/or reference chemistry. Layers may be used in conjunction with each other to provide selective permeation of the gas of interest while protecting the test strip from interfering substances. In some embodiments, there is a dielectric layer disposed above the electrodes.

Figure 17B:
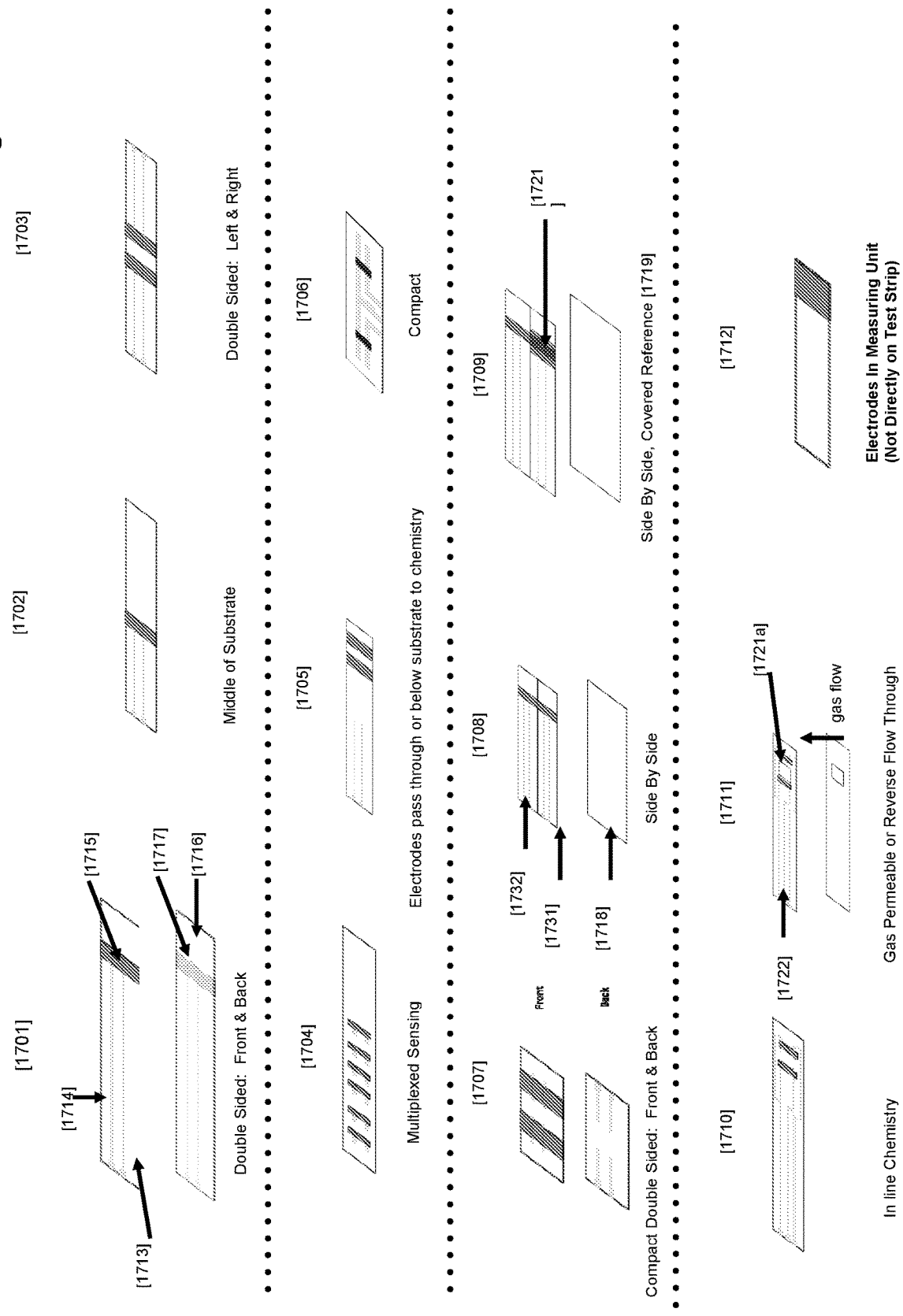

FIG. 17B and FIG. 17C shows examples [1701 through 1712 and 1722 through 1726] of various configurations of substrate, electrode, and sensing chemistries on one layer of the test strip.

In one embodiment [1701] a substrate [1713] contains electrodes [1714] and a sensing chemistry [1715] deposited across the electrodes [1714] on one side. The reverse side of the substrate [1716] also contains electrodes and a sensing chemistry. The reverse side of the substrate [1716] may be symmetric or asymmetric. Asymmetry may include different sensing chemistries, chemistry or electrode configurations, etc. The second sensing chemistry [1717] may be the same or different from the first sensing chemistry [1715]. This may be used to adjust sensitivity and selectivity to the analyte of interest. In another embodiment [1708], two test strips are manufactured separately [1732] [1731] and then assembled onto a separate substrate [1718] to form a finished test strip. This may be done to increase the ease of manufacturability if the sensing chemistries are different. In another embodiment in which the sensing chemistries are side by side [1709], one of the two sensing chemistries is covered [1721]. Another, embodiment, [1710] has in line chemistry. In another embodiment [1711], the substrate [1722] allows for the passing of gas [1721a] through it to the sensing chemistry. This allows for the test strip to be placed facing away from the gas stream as described. Examples of additional configurations [1722] and [1723] are shown with two chemistries offset on the test strip sharing one electrode. In one example [1723] one of the two chemistries is covered. In another embodiment [1724], multiple sensing chemistries are shown. In this example, the chemistries may share at least one electrode. In another embodiment [1725], at least one of the chemistries is covered. In another embodiment [1726], shows a chemistry bridging three electrodes. In this embodiment, the three electrodes may represent a working, reference and counter electrode.

Figure 17D:
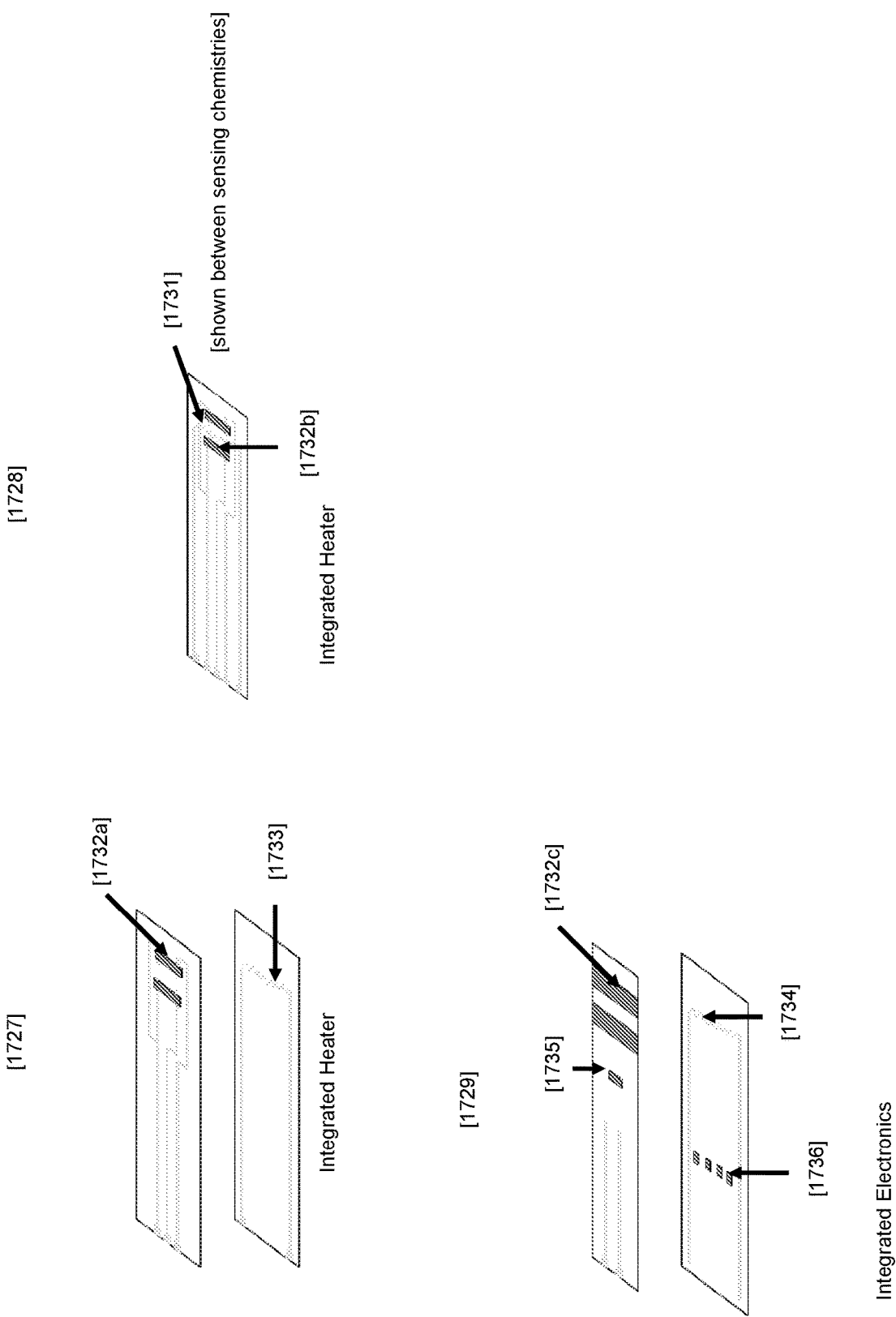

FIG. 17D shows embodiments of more complex configurations. In certain embodiments, [1727], [1728], and [1729], an integrated heater [1731], [1733], [1734] is incorporated into the test strip either on the same layer as the sensing chemistry [1732a], [1732b], [1732c] (as show in [1728]) or on a different layer (as shown in [1727]). In other embodiments [1729] the test strip has additional sensor elements [1735] and integrated electronics [1736] on at least one layer. Examples of additional sensor elements [1735] may include, but are not limited to, temperature, and/or humidity sensors. Examples of integrated electronics [1736] may include, but are not limited to, resistors, fuses, capacitors, switches, etc. The test strip may also include a means for managing or controlling the number of uses (not shown). Examples include RFID, barcodes, circuit or fuse burn out, memory on the test strip, serial number, switch, etc.

Figure 18A:
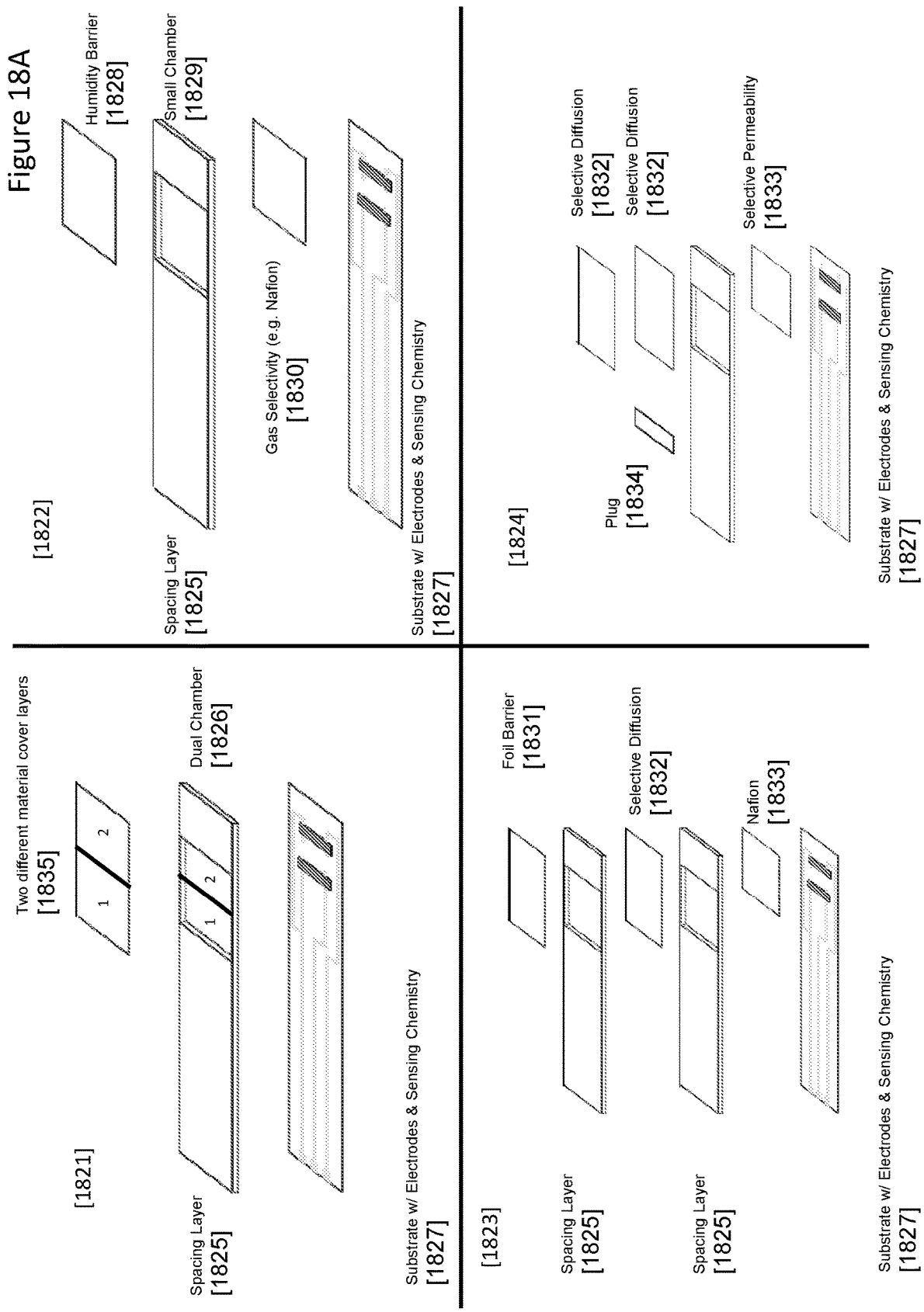
FIGS. 18A-18C show examples of the sensing chemistry configured in a line and in electrical communication with an electrode pair.

FIG. 18A shows examples of a test strip with multiple layers. Layers may be incorporated into the test strip for a variety of reasons depending on the sensing chemistry, electrode configuration, interfering substances and manufacturing process. Examples include but are not limited to: masking for chemistry deposition, support for chemistry deposition, protection from interfering substances, enhancing the selectivity and/or sensitivity of the test strip, acting as the sensing chemistry, spacing, formation of gas chamber(s), test strip rigidity or structural configuration. Layers may be comprised of porous and non-porous polymers, composite materials, fibrous materials such as paper or fiber glass, woven and non-woven textiles, membranes, polymers, adhesives, films, gels, etc. The layers may be modified, for example, in some embodiments, by chemically treating or coating and/or mechanically altering. The layers may serve one, or more than one, purpose. For example, in some embodiments, a layer may serve as a structural component (e.g. improve rigidity or as a spacer), and a selective gas permeable membrane. Layers may be used in conjunction with each other to provide selective permeation of the gas of interest while protecting the test strip from interfering substances. In some embodiments, there is a dielectric layer disposed above the electrodes.

As shown in the dual chamber example [1821], spacing layers [1825] may also be used to create a single chamber or multiple chambers [1826]. The spacing layer [1825] is disposed above the substrate with the electrode and sensing chemistry [1827]. The chambers may be uniformly covered or differentially covered [1835]. In one embodiment, the differentially coated chambers allow for different gases to diffuse into the different chambers in order to be sensed by the sensing chemistry. In another embodiment [1822] a gas selective layer [1830] is disposed above the substrate with the electrode and sensing chemistry [1827]. The spacing layer [1825] containing a small single chamber [1829] is disposed above the gas selective layer [1830]. A humidity barrier is disposed above the spacing layer and covering the small chamber [1828]. In another embodiment [1823] two spacing layers [1825] are used. The two spacing layers may be used to create a larger chamber for the gas to accumulate at the sensor surface or to separate multiple diffusion layers. The spacing layers may also serve as structural support for the test strip and its layers. A Nafion layer [1833] is disposed above the substrate with the electrode and sensing chemistry [1827]. A spacing layer [1825] is disposed above the Nafion layer [1833]. A selective diffusion layer [1832] is disposed above the first spacing layer [1825]. A second spacing layer [1825] is disposed above the selective diffusions layer [1832]. A foil barrier [1831] is disposed above the second spacing layer [1825]. In another embodiment [1824] a different combination of layers is used. A selectively permeable layer [1833] is disposed above the substrate with the electrode and sensing chemistry [1827]. Two selective diffusion layers [1832] and a plug [1834] are disposed above the spacing layer [1825]. In one embodiment, the plug [1834] functions as a sealing mechanism when a test strip is inserted into a chamber.

Layers may be designed to be reactive to certain gases.

The layers may be applied by various coating methods including but not limited to those illustrated in FIG. 16.

Examples of interferences may include but are not limited to: gases, condensed liquids, dissolved solids, particulate matter, humidity, temperature variations, etc. In the example of measuring nitric oxide in exhaled breath, examples of interferences may include:

Interfering Substances for Measuring Nitric Oxide in Exhaled Breath

| | |
|---|---|
| $CO_2$ | $H_2O$ |
| $C_2H_3N$ | $H_2O_2$ |
| $C_2H_4O$ | $H_2S$ |
| $C_2H_6O$ | $NH_3$ |
| $C_3H_6O$ | $NO_2$ |
| $C_5H_8$ | $O_2$ |
| $CO$ | pH |
| $H_2$ | |

Figure 18B:
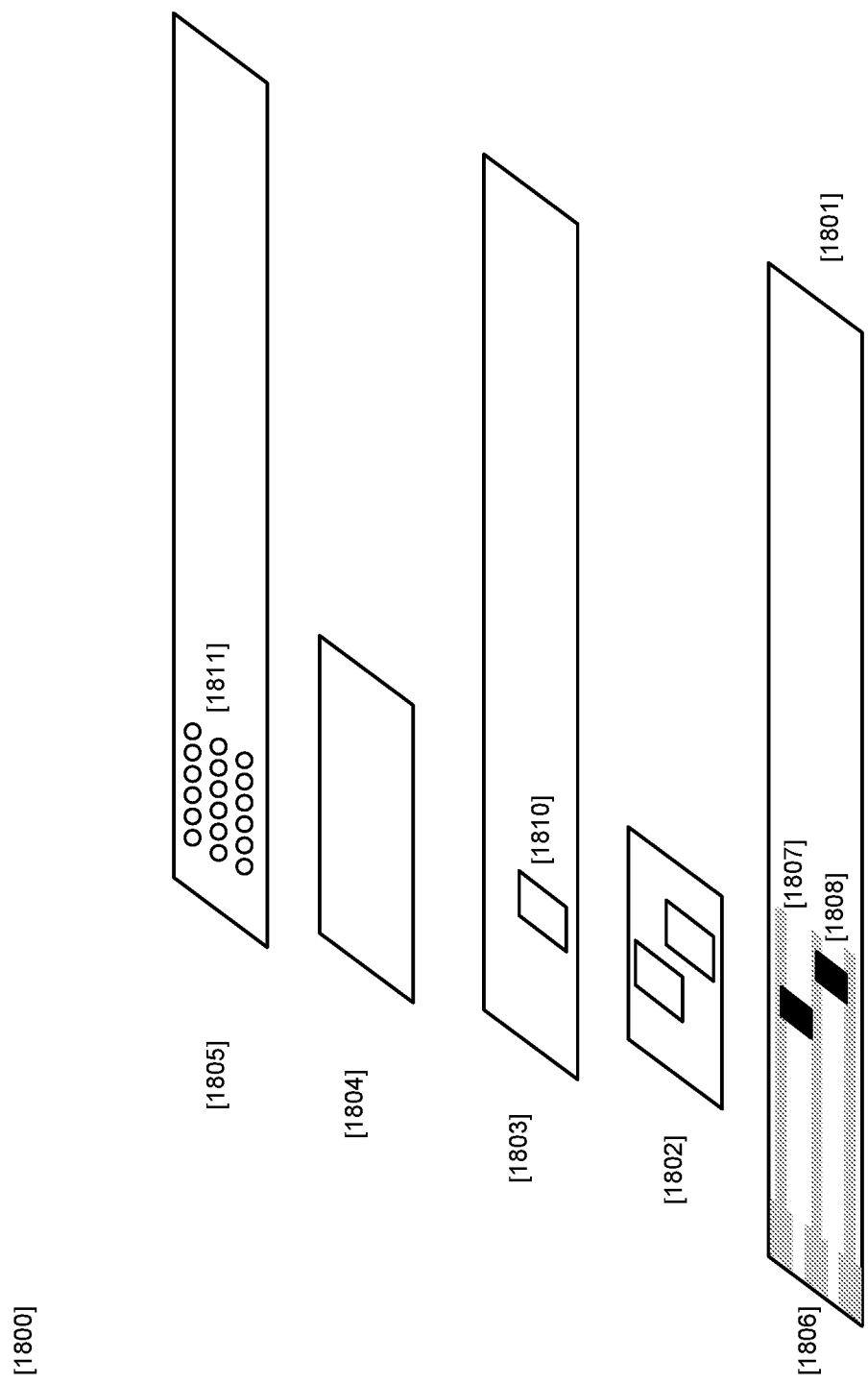

FIG. 18B demonstrates an embodiment. In this example [1800], the test strip includes a base substrate [1801] with electrodes [1806] and a sensing chemistry [1808] and reference chemistry [1807], an optional dielectric layer [1802], a layer to cover the reference chemistry [1803] and expose the sensing chemistry [1810], a membrane layer [1804], and a protective layer [1805]. The protective layer [1805] employs a means [1811] to allow gas to flow to the membrane layer [1804]. In one embodiment, the membrane layer [1804] contains silicone.

Figure 18C:
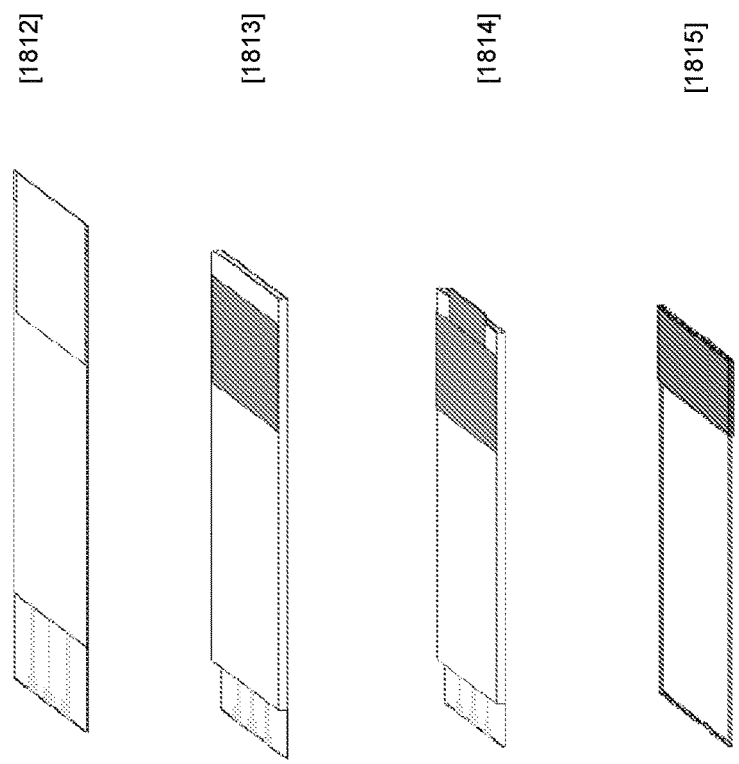

FIG. 18C demonstrates examples of assembled test strips. [1812] depicts a fully assembled test strip. Embodiment [1813] depicts test strip with a foil barrier for puncture with a companion device. Embodiment [1814] depicts a test strip with a foil barrier that has a manual removal tab. Embodiment [1815] depicts a test strip with electrodes in the measuring unit rather than on the test strip itself. This this later embodiment, electrodes disposed in a companion device contacts the sensing chemistries on the test strip when the device and test strip are mated.

In other embodiments, the heater, additional sensor elements, and integrated electronics described herein are incorporated into the reader meter.

In other embodiments, the heater, additional sensor elements, and integrated electronics described herein are incorporated into the reader and/or the chamber in which the test strip is placed.

Other examples (not shown) may include an electrode configuration suitable to measure an electrochemical reaction (i.e. working electrode, counter electrode, reference electrode).

In one embodiment, the test strip may be comprised of a substrate, at least one electrode, at least one sensing chemistry, and, optionally, at least one layer to protect the sensing chemistry from interfering substances. The sensing area may consist of at least two nanonetworks in electrical communication with one or more electrical contacts. One network will act as the active sensing chemistry and will be sensitive to a particular set of analytes (e.g. nitric oxide or nitrogen dioxide). Additional networks will act either as a reference, as sensors for different analytes, or for the same analyte for signal averaging. The reference may be sensitive to a different set of analytes such that the differential signal between the active sensing chemistry, and the reference results in signal sensitivity towards a single analyte, a small set of analytes, or a subset of analytes with which the test strip is sensitive. In the case of multiplexed analysis, there may be more than one reference.

In another embodiment, the test strip may be comprised of a substrate, at least one electrode, at least one sensing chemistry, and optionally at least one layer to protect the sensing chemistry from interfering substances. The sensing area may consist of at least two nanonetworks deposited between two or more electrodes. One network will act as the active sensing chemistry and will be sensitive to a particular set of analytes (e.g. nitric oxide, nitrogen dioxide, carbon dioxide, hydrogen, or methane). The second network will act as a reference. The reference may consist of the same sensing chemistry as the active nanonetwork and may be covered or uncovered. The test strip and chemistries may be configured as a resistive circuit or bridge circuit.

In some embodiments the active chemistry and sensing chemistry are pre-mixed before deposition on the substrate. In some embodiments, the active and sensing chemistry are deposited in less than or equal to four steps.

In some embodiments of the invention, the test strip contains a chromatographic layer. A chromatographic layer enables at least one of the analytes in the sample to move through the chromatographic layer at a different rate relative to the movement of other analytes in a plurality of analytes (e.g. breath or ambient air).

An aspect of the invention provides a system for determining the concentration of at least one analyte in a fluid sample having a plurality of analytes, the system comprising, a base substrate, a first electrode pair disposed over the base substrate, a first sensing chemistry responsive to at least one analyte in the sample, wherein the first sensing chemistry is in electrical communication with the first electrode pair, and a first chromatographic layer disposed over the at least one sensing chemistry, wherein at least one analyte of the plurality of analytes moves through the first chromatographic layer at a different rate relative to the movement of other analytes of the plurality of analytes.

In another embodiment the system of further comprises at least one of a blocking layer and a second chromatographic layer disposed over the second sensing chemistry, wherein the blocking layer inhibits contact between the second sensing chemistry and at least one analyte in the fluid sample, and wherein at least one analyte of the plurality of analytes moves through the second chromatographic layer at a different rate relative to the movement of other analytes of the plurality of analytes. Other aspects of the invention may contain any number of chromatographic layers.

One aspect of the invention provides a method for determining the concentration of at least one analyte in a fluid sample, the method comprising, providing a system comprising, a base substrate, a first electrode pair disposed over the base substrate, a first sensing chemistry responsive to at least one analyte in the sample, wherein the first sensing chemistry is in electrical communication with the first electrode pair, and a first chromatographic layer disposed over the at least one sensing chemistry, wherein at least one analyte of the plurality of analytes moves through the first chromatographic layer at a different rate relative to the movement of other analytes of the plurality of analytes, and measuring at least one of a voltage across the first electrode pair, a resistance across the first electrode pair, and a current flow across the first electrode pair.

Figure 30:
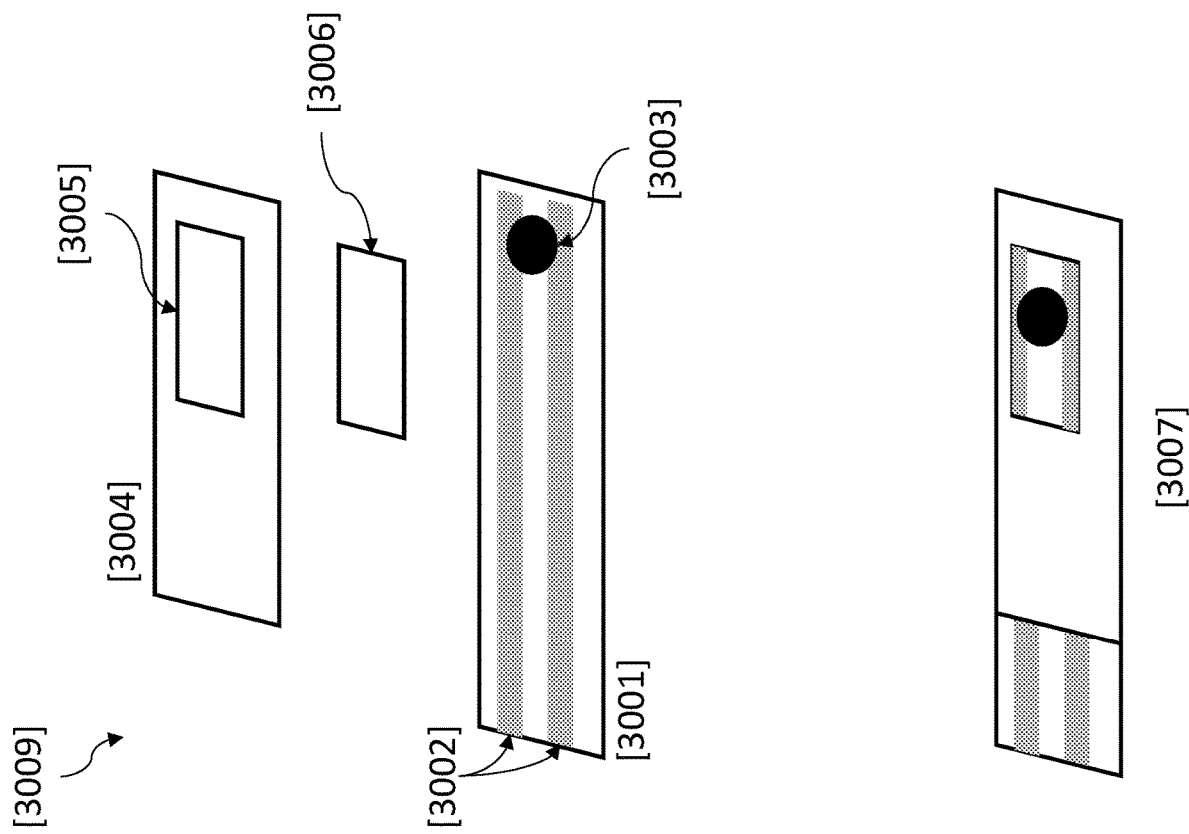
FIG. 30 is an example of a test strip with a chromatographic layer containing a single sensing chemistry.

FIG. 30 demonstrates one embodiment of a test strip [3009] configured to sense gas or gases utilizing a chromatographic separation layer. The test strip consists of a substrate [3001], electrodes [3002], at least one sensing chemistry [3003] and layer [3004] containing a chromatographic separation material [3006]. In a preferred embodiment, the chromatographic separation material [3006] is disposed over a sensing chemistry [3003] that bridges an electrode pair [3002]. The chromatographic separation material may be integrated into another layer or may stand as its own layer. If integrated, the layer [3004] may provide structural support for a chromatographic material for example while defining a window to enable the analyte to reach the chromatographic layer [3008] and sensing chemistry [3003]. A fully assembled test strip with a chromatographic layer is shown [3007]. Herein, a chromatographic layer shall mean any layer that contains a chromatographic material that enables at least one of the analytes in a sample to move through the chromatographic material at a different rate relative to the movement of other analytes of the plurality of analytes. The chromatographic material and any additional layer may be processed in many ways prior integration. Examples of processing include but are not limited to die cutting, laser cutting, kiss cutting, surface energy modification (UV radiation, plasma and corona discharge or by flame or acid treatments or other techniques known in the art.), spray treatment with adhesive, lamination with or without a pressure sensitive adhesive etc.

Figure 31:
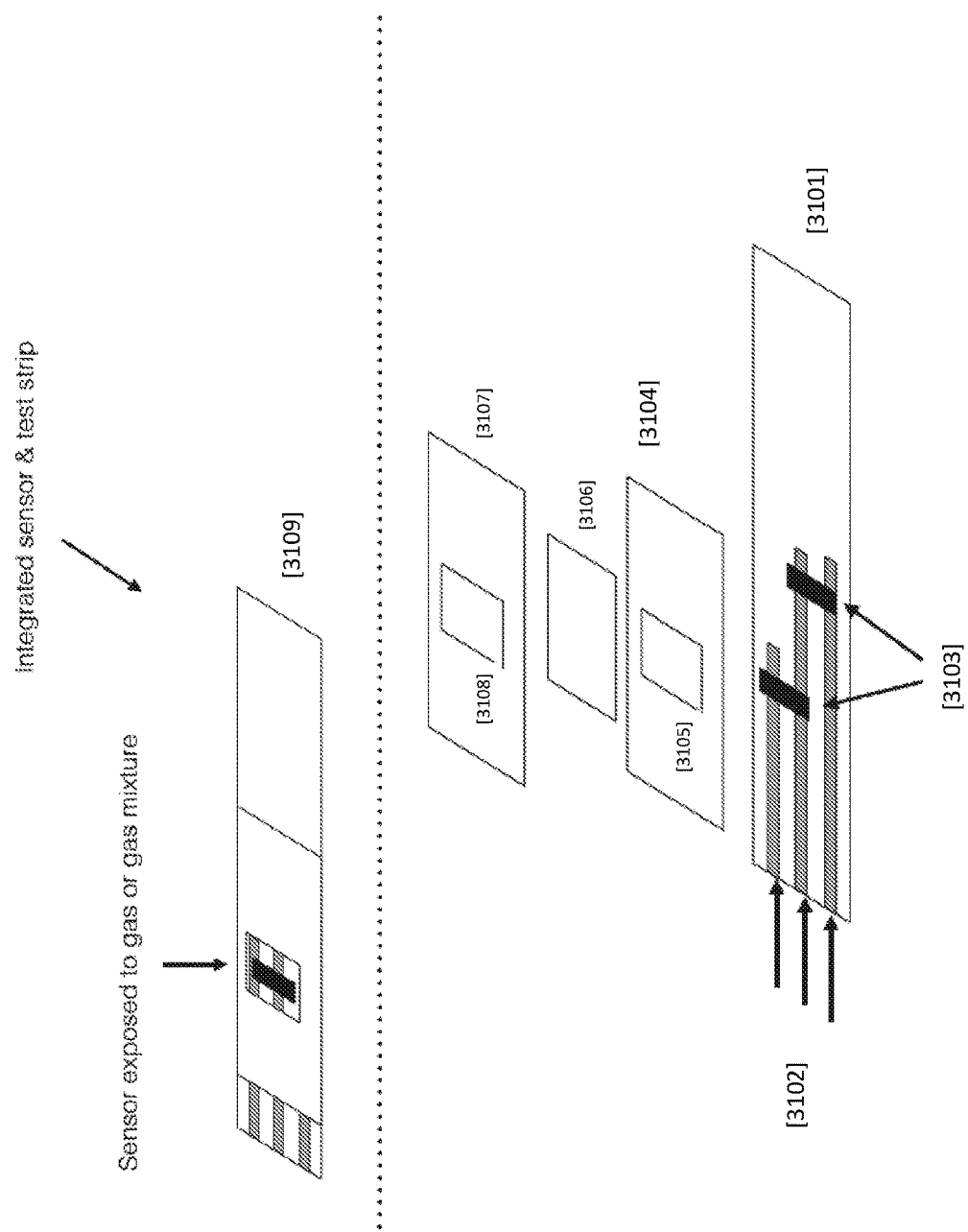
FIG. 31 is an example of a test strip with a chromatographic layer containing two sensing chemistries and additional structural layers.

FIG. 31 demonstrates one embodiment of a test strip [3109] configured to sense gas or gases utilizing a chromatographic separation layer. The test strip consists of a substrate [3101], electrodes [3102], optionally a dielectric layer (not shown), two sensing chemistries [3103], a layer designed to cover one of the sensing chemistries and expose the second sensing chemistry [3104], a chromatographic separation layer [3106], a protective layer [3107] with a window [3108] to expose the sensor to the gas or gas mixture. The layers [3104] and [3107] may be processed in many ways to create openings [3108] and [3105] that expose one of the chemistries for sensing. Examples of processing include but are not limited to die cutting or laser cutting. The layers [3104], [3106], [3107] may be processed in many ways prior to assembling the layers together in a test strip. Examples of processing include but are not limited to die cutting, laser cutting, kiss cutting, surface energy modification (UV radiation, plasma and corona discharge or by flame or acid treatments or other techniques known in the art.), spray treatment with adhesive etc.

Figure 32:
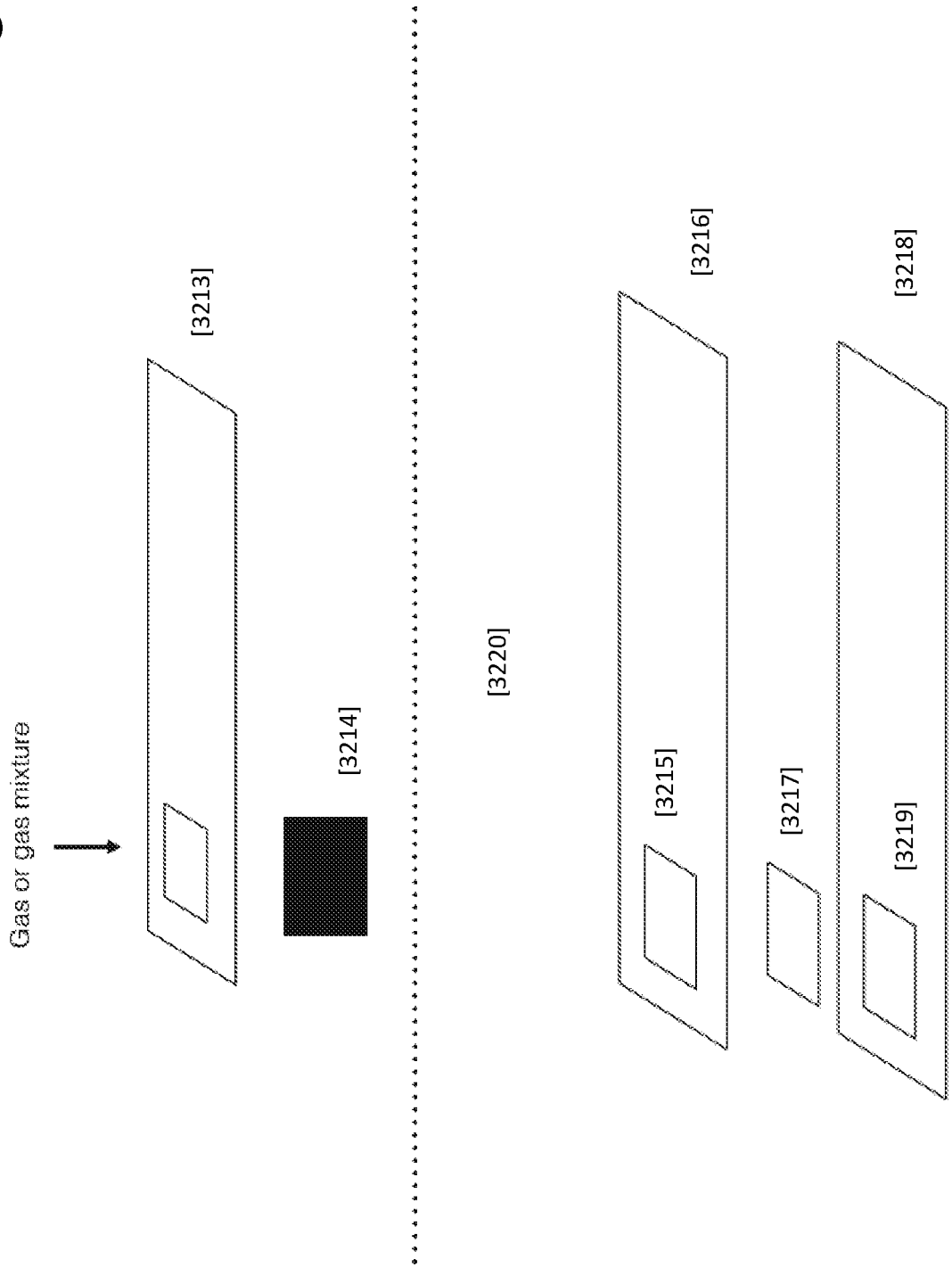
FIG. 32 is an example of a test strip with a chromatographic layer that is not integrated with a sensor.

In another embodiment, the test strip only serves as a chromatographic layer and does not contain a sensing element (FIG. 32). In this embodiment, the test strip with chromatographic layer [3213] is used in conjunction with another sensor [3214]. In addition to test strips, other sensors may include metal oxide (MOS, CMOS etc), electrochemical, optical, MEMS, FET, MOSFET, ChemFET, or other type of sensor known in the art. The test strip [3213] may be single use, multi-use or limited use. It may be disposable or reusable. It may also be single patient use. One embodiment of a test strip that only serves as a chromatographic layer is shown [3220]. In this embodiment, the chromatographic layer [3217] is layered in-between two substrates [3216] and [3218]. The substrates may contain windows [3215] and [3219] to allow gas to pass through the chromatographic layer [3217]. Other substrate configurations are possible without deviating from the spirit of the invention. One example would be a chromatographic material [3217] and structural layer [3216]. Other examples include but are not limited to substrates that provide structural support for the chromatographic layer or are used to integrated the chromatographic layer with a sensor or device.

In some implementations, the chromatographic diffusion and/or permeation layer may consist of an impregnate, may be comprised of porous and non-porous polymers, composite materials, fibrous materials such as paper or fiber glass, woven and non-woven textiles, membranes, polymers, adhesives, films, gels, etc. In some implementations, the layer or layers may be modified, for example, in some embodiments, by chemically treating or coating and/or mechanically altering its surface. Other examples of materials suitable for chromatographic layers are incorporated herein (Test Strip—Layers). In some implementations, the layer may contain additional materials or undergo additional processing to make it suitable for manufacturing.

In one embodiment, the chromatographic layer is made up of silicone or a membrane or film containing silicone. In one embodiment, its thickness is between 1 μm and 200 μm for fast analysis. In another embodiment the thickness is greater than 200 μm for delayed analysis (hours or days). In another embodiment the thickness is greater than 1 inch for analysis over a period of days, weeks or years.

In another embodiment, the chromatographic layer is treated with a material to selectively remove chemicals and/or water (including water vapor). Treatment includes but is not limited to coating, spraying, chemically bonding etc.

In another embodiment, the chromatographic layer is designed to prevent water vapor from condensing on the sensing chemistry.

In another embodiment, the chromatographic layer is treated with Nafion.

In another embodiment, the chromatographic layer is treated with a sulfonic acid.

In another embodiment, the chromatographic layer contains silicone and Nafion.

In another embodiment, the chromatographic layer contains silicone and sulfonic acid.

In another embodiment, one of the test strip layers contains sulfonic acid or Nafion.

In another embodiment, the chromatographic layer may contain sorbent particulates to modify the chromatographic properties, such as activated carbon, functionalized silica, alumina, clays, diatomaceous earth, mineral carbonates, polymers, and other filler materials known to those skilled in the art.

In another embodiment, the chromatographic layer may contain emulsified components to modify the chromatographic properties, such as emulsified water, oils, gases, organic solvents, polymers, organic molecules, and other biphasic chemicals known to those skilled in the art.

Chromatographic Detection

The gas detection method referenced hereafter is based on the selective diffusion and/or permeation properties of a chromatographic layer. The method utilizes at least one of the following methods to separate and analyze the concentration of a single gas or multiple gases: the physical and chemical properties of the material, thickness of material, time, temperature, pressure, signal strength/magnitude, and/or signal slope, change from a single baseline and/or change versus multiple baselines, overshoot and/or under shoot versus a fixed point (e.g. the baseline), change in the first or second derivative of the signal, change in the shape of a signal (e.g. the full width at half maximum of a peak, peak position, curve modality, etc), ratios of two or more signal properties, or changes in any of the signal characteristics or chromatographic layer characteristics previously mentioned. Utilizing multiple methods in combination is also possible without deviating from the spirit of the invention. The method improves sensitivity and selectivity of the sensor and allows for complex multiplexing from a single chemistry. Gas, including water vapor, passing through the chromatographic layer shall hereafter incorporate this method.

In one embodiment, the test strip is calibrated to the gas or gases of interest. The test strip may also be calibrated versus gases that have the potential to interfere with the gas of interest. Calibration may include the linearization of sensor signal to one or multiple gases to convert the signal to a quantity (e.g. part per billion or part per million) of analyte.

In one embodiment the sensor and/or sensing chemistry is designed to have a differential response to the gas of interest and to interfering gases.

In another embodiment, the chromatographic layer is designed to provide both separation and specificity to the sensor and/or sensing chemistry.

Figure 33A:
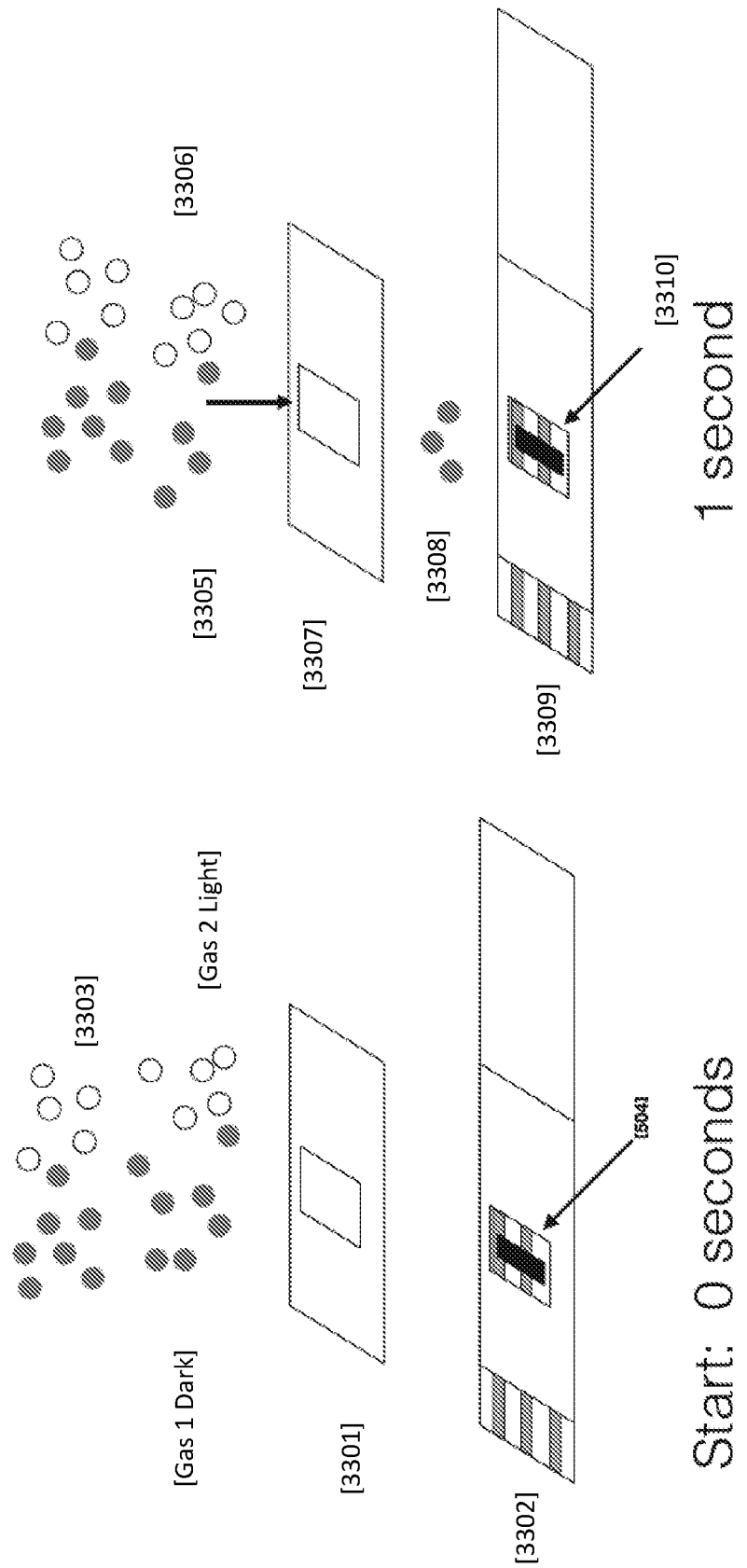
FIG. 33A is an example of a mixed gas sample arriving at the test strip, above the chromatographic layer, and beginning passing through the chromatographic layer to the sensor.
Figure 33B:
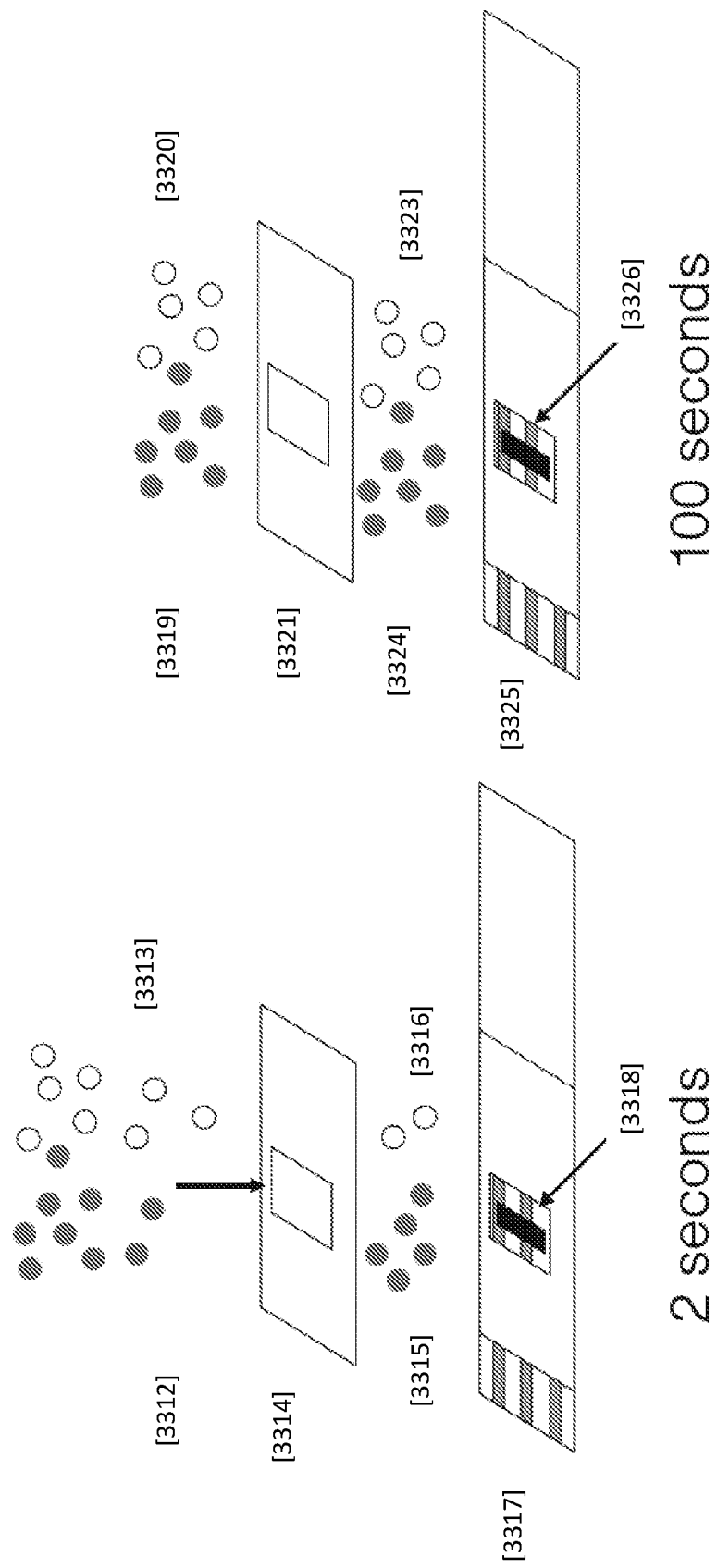
FIG. 33B is a continuation of the example from FIG. 33A.

FIG. 33A depicts a test strip [3302] with its chromatographic layer [3301] separated for illustrative purposes with a mix of gas molecules [3303] above the chromatographic layer. Two molecules are depicted but any number of molecules is possible without deviating from the spirit of the invention. As time passes, the gas above the chromatographic layer begins to pass through the layer. The properties of the chromatographic layer create a time-based separation so that gas selectively and predictively passes through the layer to the sensing chemistry for detection. In one embodiment, shown in FIG. 33A, Gas 1, represented by dark circles, and Gas 2 represented by light circles (collectively [3303]) arrive to the test strip [3302] above the chromatographic layer [3301]. At zero seconds, the initial condition, 0% of Gas 1 and 0% of Gas 2 are on one side of the chromatographic layer. After 1 second, ~43% of Gas 1 [3305] and [3308] required to reach equilibrium has passed through the chromatographic layer [3307], while 0% of Gas 2 [3306] required to reach equilibrium has passed through. At 2 seconds (FIG. 33B), Gas 1 [3312] and [3315] is at 71% equilibrium concentration on the sensor side of the chromatographic layer [3314] and Gas 2 [3313] and [3316] is at ~40% equilibrium. At some point in time, 100 seconds in this example, both Gas 1 [3319] and [3324] and Gas 2 [3320] and [3323] are at 100% of their equilibrium value below the chromatographic layer [3321] at the level of the test strip [3325]. In this context, equilibrium refers to the equilibrium of gas diffusion across the membrane, and not an equilibrium with the sensor surface. What is represented as a gas in this figure could also be any fluid including a liquid.

Figure 34:
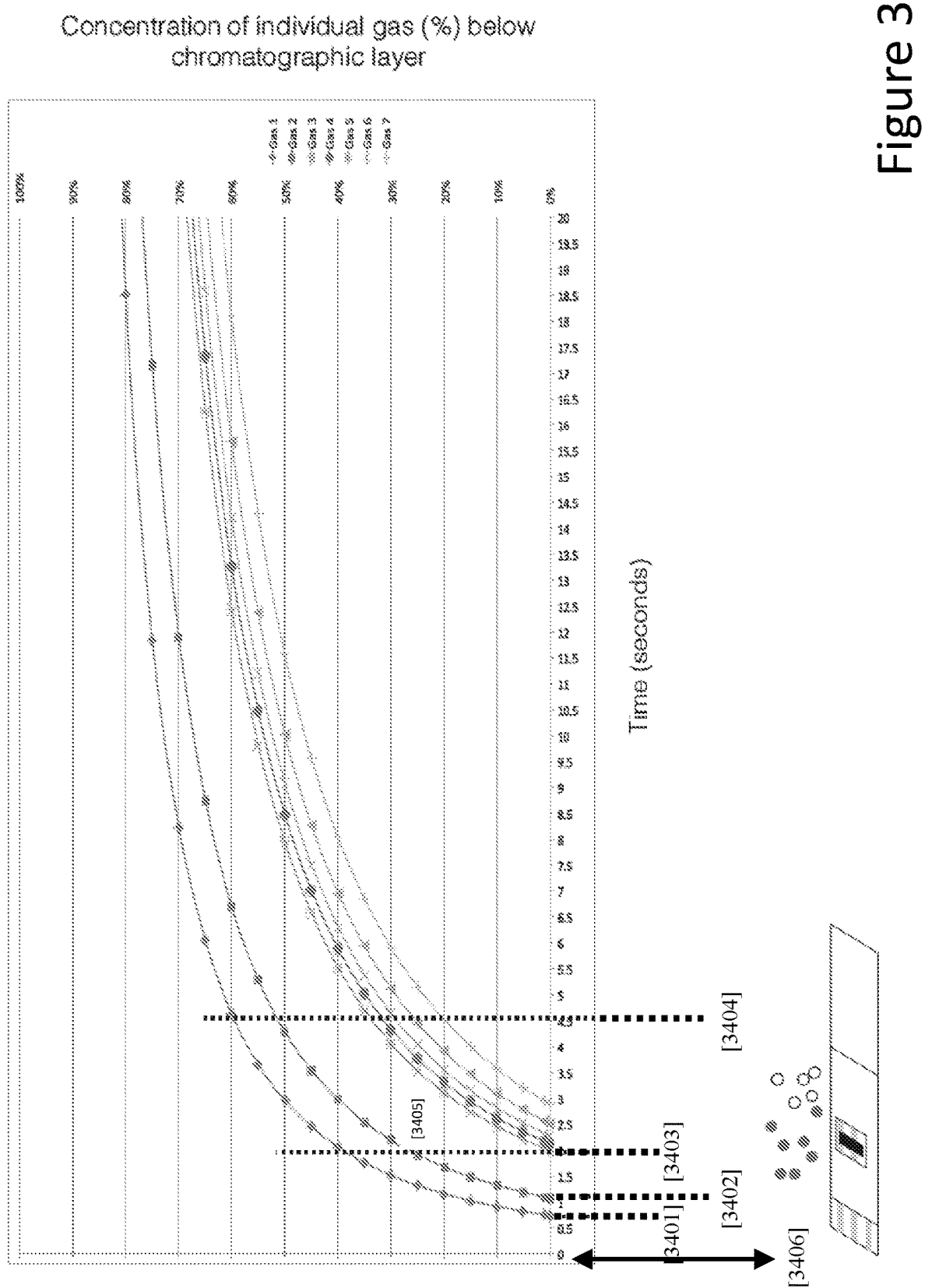
FIG. 34 shows a detailed explanation of a 7 gas mixture and percentage of gas diffused through chromatographic separation layer versus time.

FIG. 34 shows the gas-time separation provided by the chromatographic layer that contains silicone at 100 µm thick. In this example, each gas is plotted individually from the gas mixture and is expressed in relation to its own equilibrium concentration (i.e. at time 0, 100% of the individual gas is above the chromatographic layer and at time>0, a certain percentage of the individual gas has passed through the chromatographic layer to approach the equilibrium value). In FIG. 34, the gas arrives above the chromatographic layer of the test strip at time 0 [3406]. At 0.75 seconds [3401] the first molecules of Gas 1 pass through the chromatographic layer and arrives at the surface of the sensor. At 1 second [3402], the first molecules of Gas 2 pass through the chromatographic layer and arrive at the sensor. At 2 seconds [3403] Gas 5 begins to pass through the chromatographic layer. Over various time intervals between 2 and 3 seconds, the remaining gases begin to pass through the chromatographic layer. Eventually, after enough time passes, all of the gases will reach 100% of their equilibrium concentration below the chromatographic layer (not shown in FIG. 34). Any number of gases is possible without deviating from the spirit of the invention.

The sensor or detector placed adjacent to the chromatographic layer may be any number of gas or liquid sensing apparatuses, whereby the signal may be, but is not limited to, optical, acoustic, mechanical, or electronic. Other embodiments are possible without deviating from the spirit of the invention, such as those set forth elsewhere herein.

The signal produced by the sensor at 1 second [3402] is 20% of the equilibrium concentration of Gas 1 versus 0% of Gases 2 through 7. At 2 seconds [3403] the signal produced by the sensor is 35% of the equilibrium concentration of Gas 1 versus 25% of the equilibrium concentration of Gas 2 versus 0% of Gases 3, 4, 5, 6 and 7. At 4.25 seconds [3404] the signal produced by the sensor is approximately 58% of Gas 1 versus 50% of Gas 2 versus less than 40% of Gas 3 through 7 and so on. Any number of gases is possible without deviating from the spirit of the invention.

In one embodiment, the concentrations of Gas 1 and Gas 2 can be determined by comparing the signal to a calibration table at a given time before other gasses have passed through chromatographic layer. The signal may be determined from a baseline reading as the test strip acclimates to its environment.

In another embodiment, the concentration of Gas 2 may be determined by enhancing the sensing chemistry to respond more favorably to Gas 2 than to Gas 1. The system may be calibrated to detect a signal of Gas 2 against a mixture of Gas 1 or other gases that pass through the chromatographic layer before Gas 2. At a given time, for example 2 seconds in FIG. 34, the signal represents 25% of the total concentration of Gas 2 against a background of only Gas 1. The total concentration of Gas 2 may be determined by comparing the signal at 25% to a linear output of 100% of the signal in a calibration table.

In one embodiment, the test strip and sensing system is calibrated to the gases found in exhaled human breath.

In one embodiment, the test strip and sensing chemistry is calibrated against a background of at least one of the gases found in exhaled human breath, including water vapor.

In another embodiment, the test strip and sensing chemistry is designed to have a differential response to water vapor and the gas of interest.

Figure 35A:
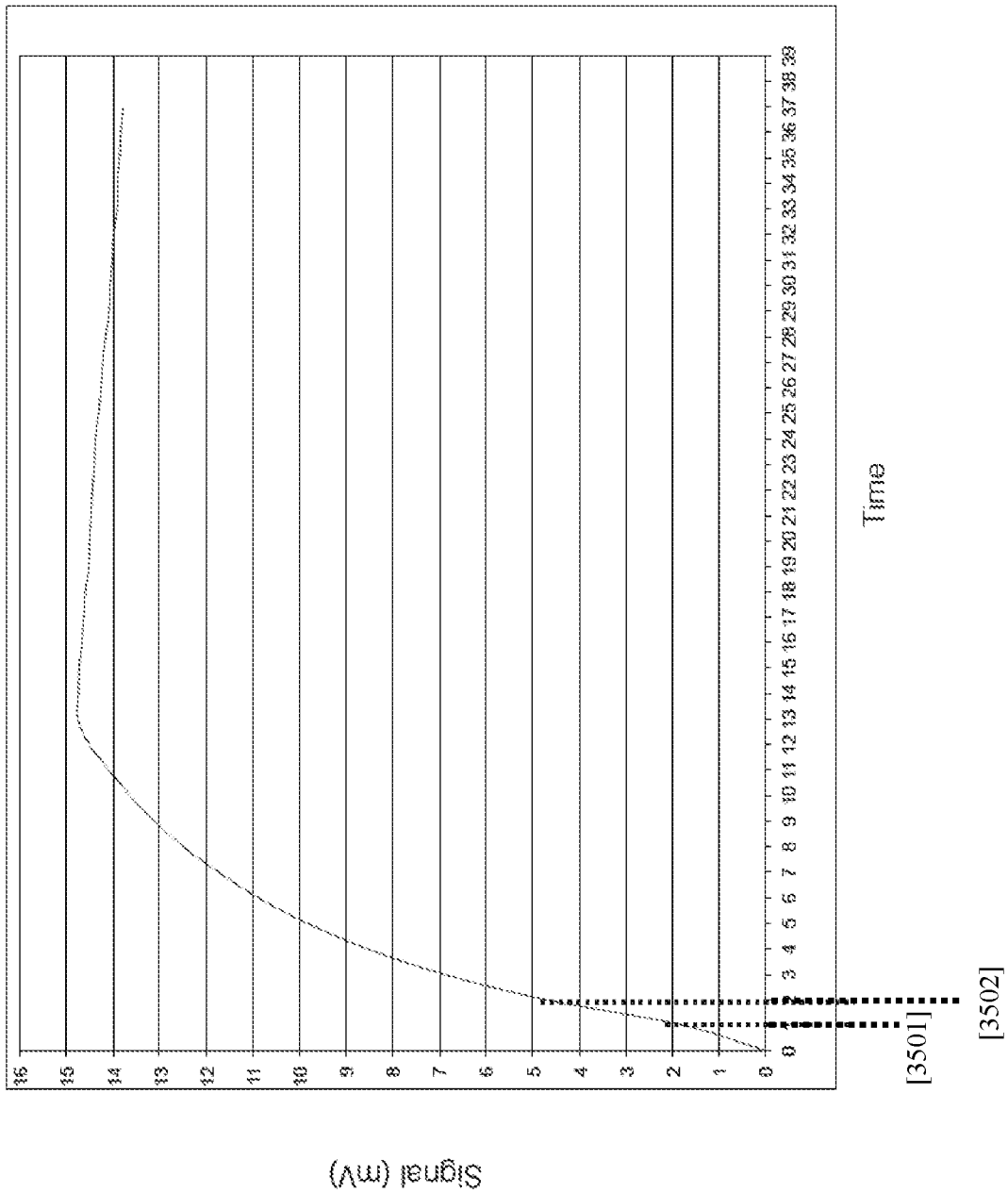
FIG. 35A demonstrates a single breath profile versus time on a test strip utilizing a chromatographic layer.
Figure 35B:
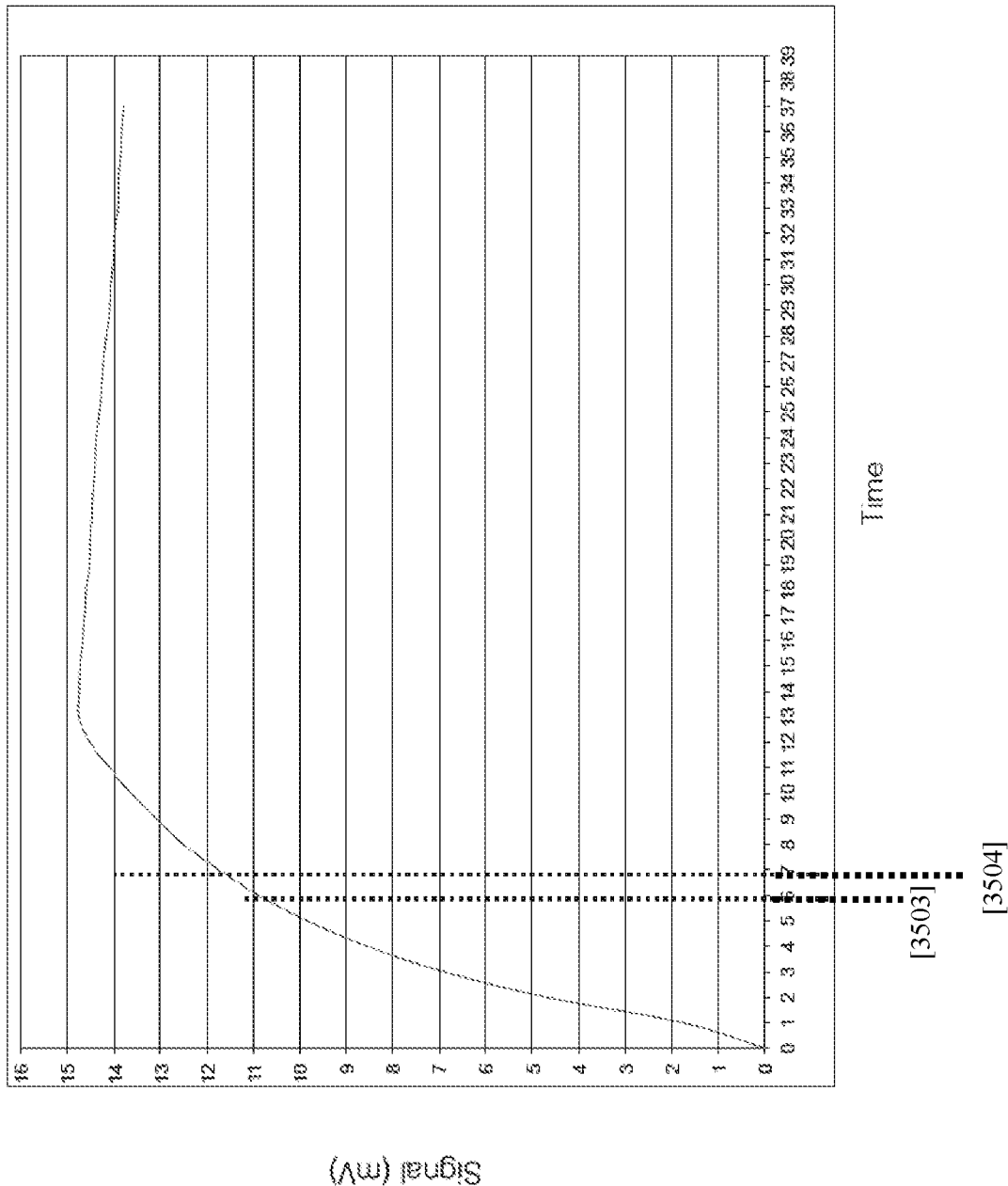
FIG. 35B shows points in time where a signal may be sampled from a single breath profile.
Figure 36:
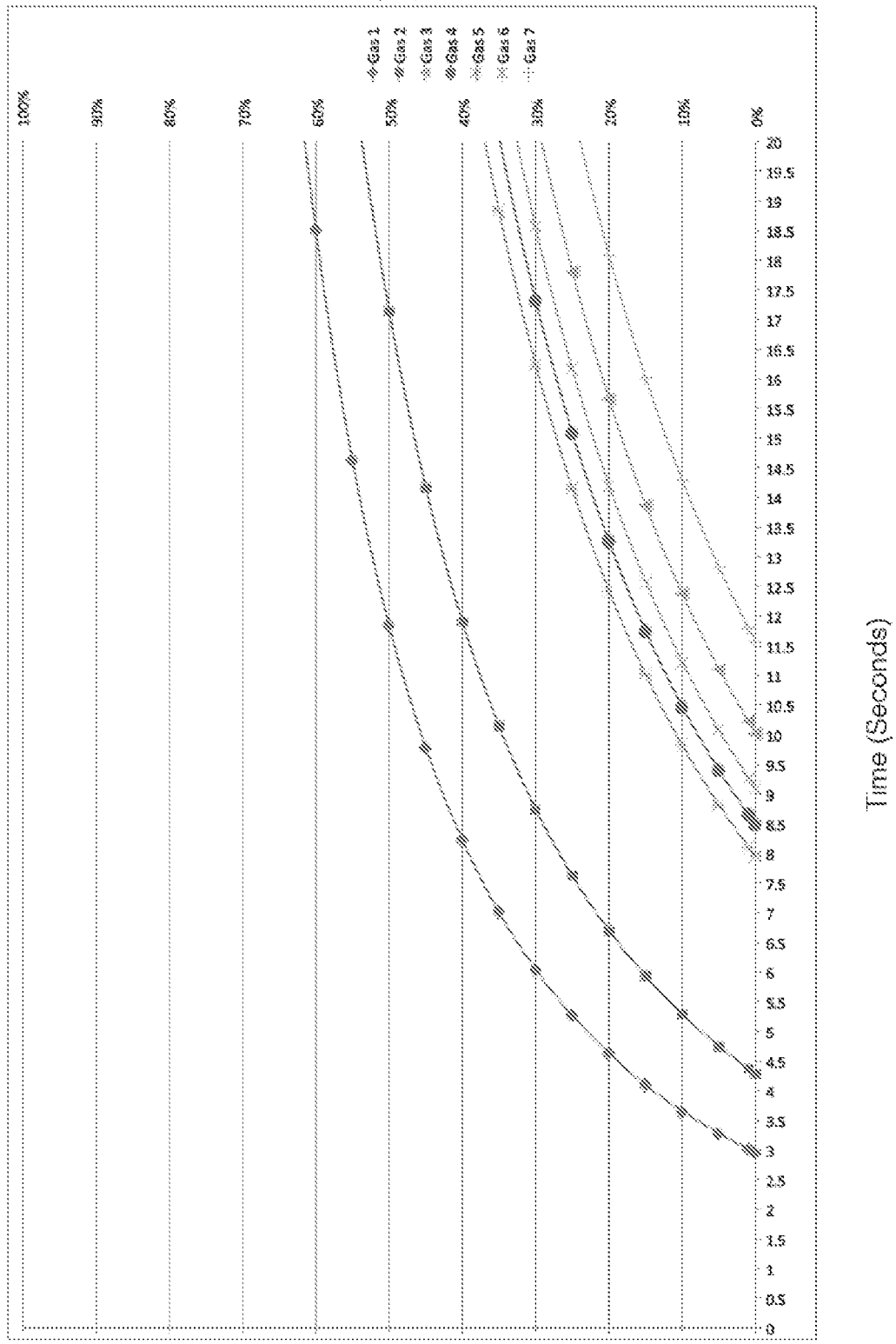
FIG. 36 demonstrates the gas separation of a 200 um thick chromatographic layer expressed as concentration of gas below the layer versus time.
Figure 37:
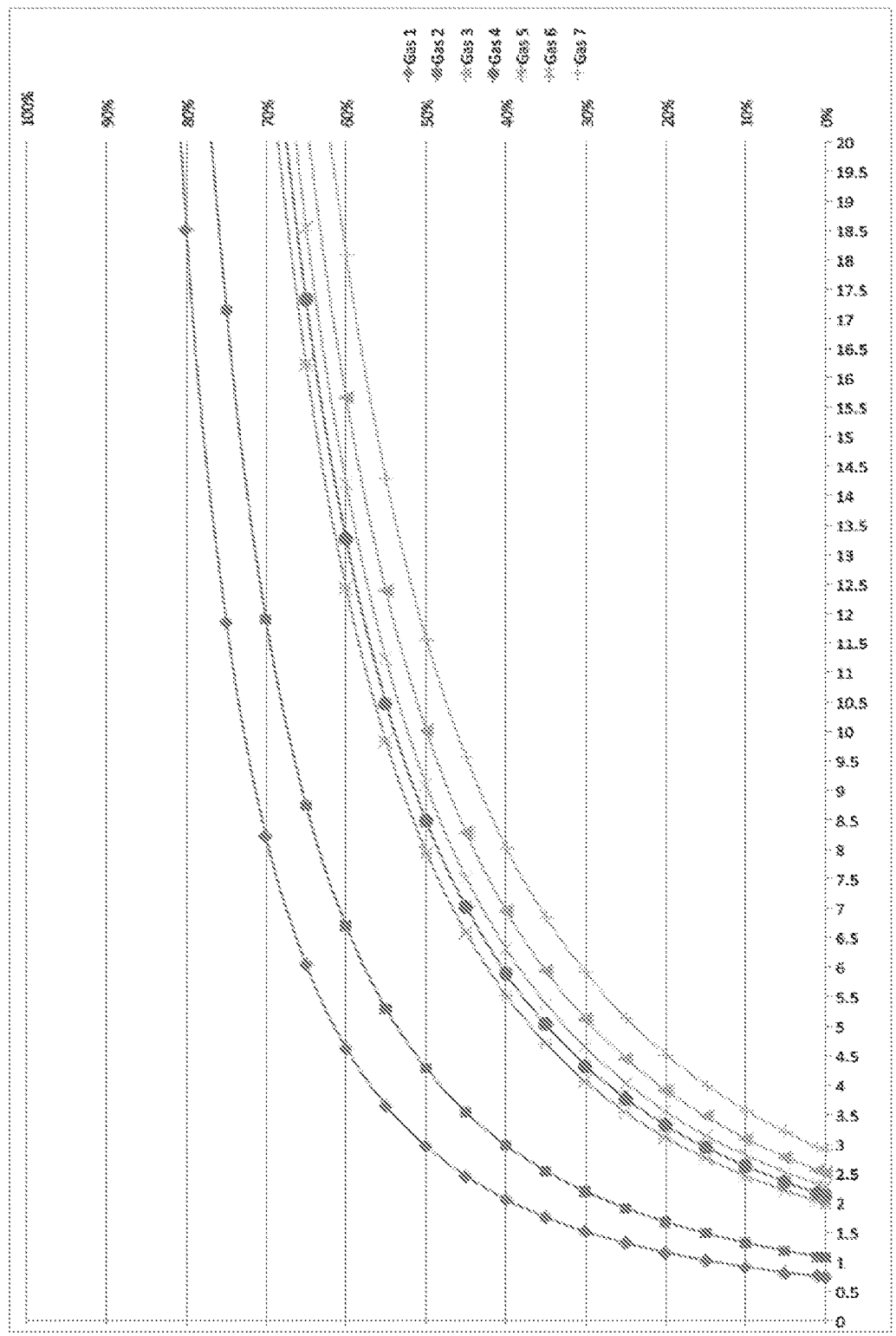
FIG. 37 demonstrates the gas separation of a 100 um thick chromatographic layer expressed as concentration of gas below the layer versus time.
Figure 38:
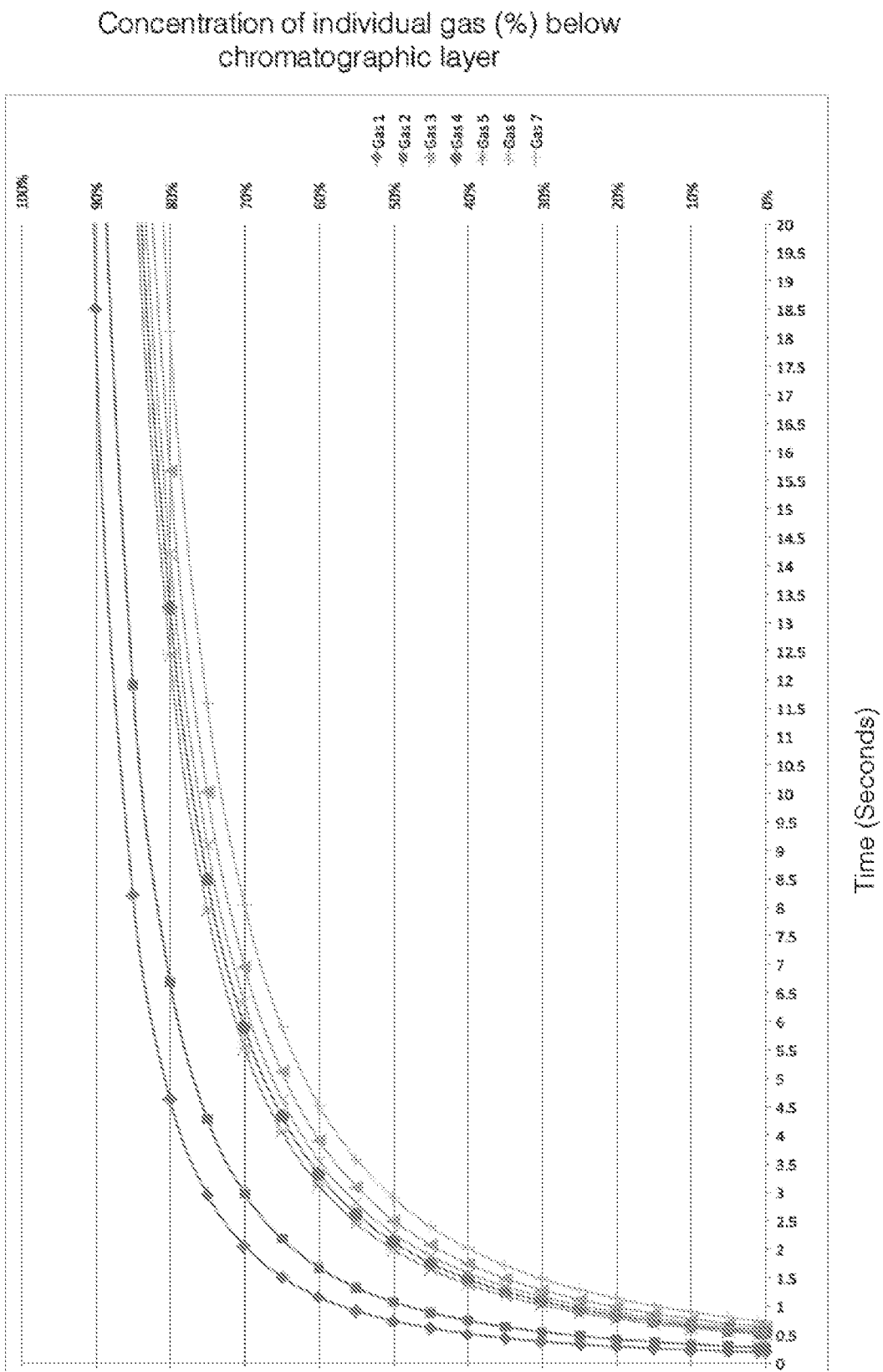
FIG. 38 demonstrates the gas separation of a 50 um thick chromatographic layer expressed as concentration of gas below the layer versus time.
Figure 39:
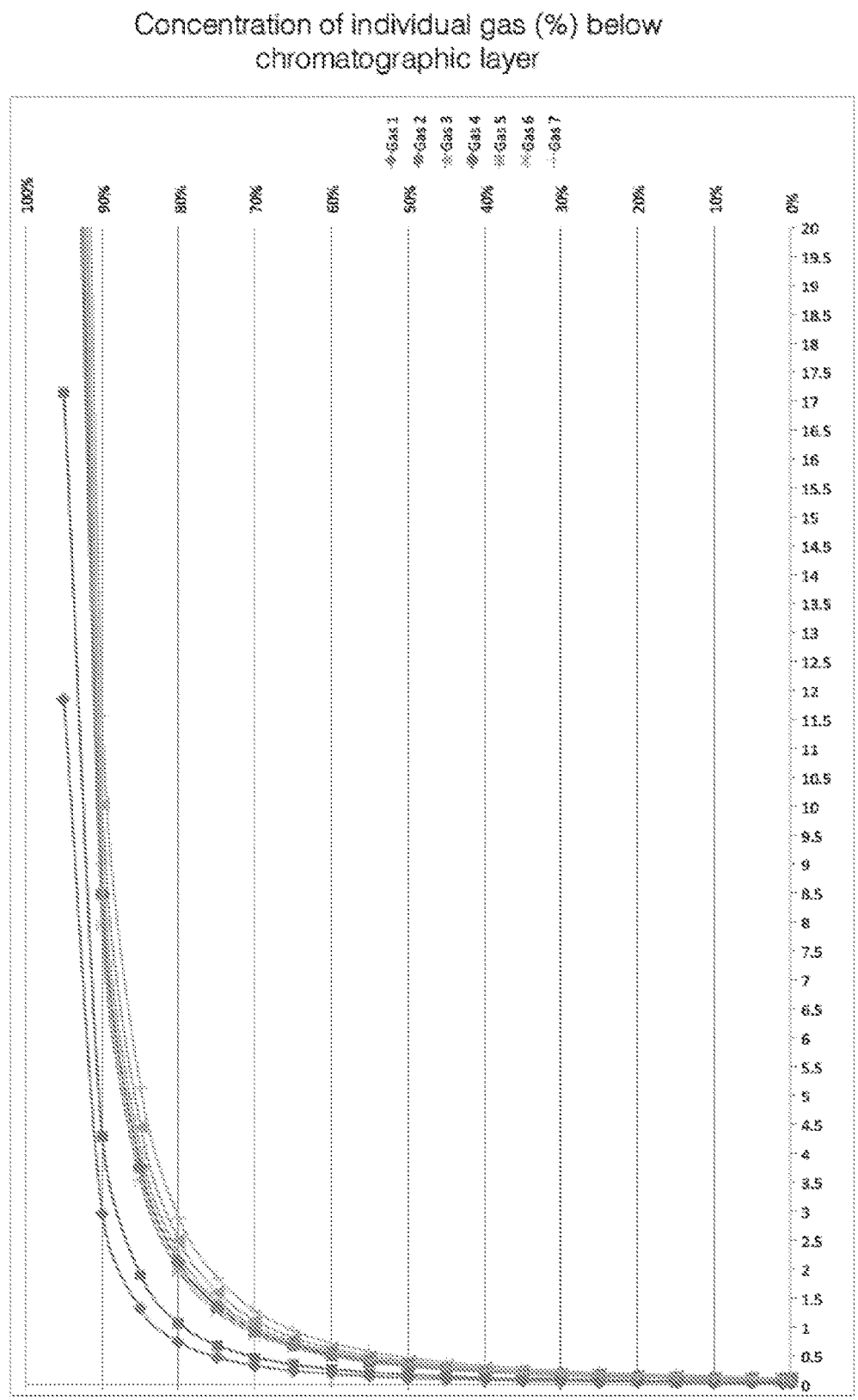
FIG. 39 demonstrates the gas separation of a 20 um thick chromatographic layer expressed as concentration of gas below the layer versus time.

FIG. 35A and FIG. 35B demonstrate a single breath profile versus time as recorded and plotted by the sensor with a 100 µm chromatographic layer. The signal represents a relative measurement (e.g. a change expressed in millivolts vs. time) from a baseline measurement. The millivolt signal is compared to a calibration table for quantitative and/or qualitative analysis (e.g. signal equals 10 parts per billion of nitric oxide or the signal is <20 parts per billion of nitric oxide). In this example the gas mixture contains the gases found in human breath arrive at the test strip at Time 0. The gas of interest to be detected is nitric oxide. At 1 second [3501], nitric oxide begins to pass through the chromatographic layer. At two seconds [3502], the signal is 4.75 mv which can be translated in a part per billion quantity. In one embodiment, measurements of the signal are sampled at various time [3501], [3502], [3503], [3504] to determine the quantity of a second gas or gases and/or confirm the initial signal sampled.

In one embodiment nitrogen monoxide is converted in nitrogen dioxide and the chromatographic layer and sensor are configured to allow nitrogen dioxide to pass and be sensed.

In one embodiment a baseline is taken to confirm the accuracy (e.g. quality control check) of the test strip prior to introduction of the gas sample.

In one embodiment, the gas sample interacts with the test strip and sensing chemistry, further described herein, changing the resistance or other electrical property of the sensor which is measured and displayed, for example, in millivolts.

In one embodiment, a known current is passed through the test strip electrodes to perform the resistive or voltage measurements.

In one embodiment, resistance is measured directly.

In one embodiment, the current passed through the test strip electrodes is pulsed.

In one embodiment, the signal is converted into the frequency domain.

In another embodiment, the test strip and sensing system measures liquids.

In another embodiment, the test strip and sensing system measures biological fluids.

In another embodiment, the test strip and sensing system measures breath condensates.

In another embodiment, the system is calibrated to each of the gases in the expected gas stream individually and in relation to one another. The signals of each gas are linearized and the concentration or concentrations can be determined at a given point in time.

In another embodiment, a gas that passes slowly through the chromatographic layer is the gas of interest. For example, in FIG. 34, Gas 3 is the gas of interest and the signal of Gas 1 and Gas 2 is subtracted or re-baselined at each point in time until a given percentage of Gas 3 has passed through the chromatographic layer. In some embodiments, the information used to re-baseline at each point in time is determined empirically on gas mixtures having known concentrations of known gases.

In another embodiment, increasing or decreasing the temperature of the environment on or near the test strip is utilized to change the properties of gas separation.

In another embodiment, the test strip itself is heated or cooled.

In another embodiment, the concentration of a gas is determined before other gases arrive at the sensor (i.e. pass through the chromatographic layer).

Measuring any gas in the gas mixture, regardless of when it passes through the chromatographic layer, is possible without deviating from the spirit of the invention.

FIGS. 36, 37, 38, 39 demonstrate time separation of the chromatographic layer at various thicknesses. The figures show the concentration of individual gases, expressed as a percentage diffused through the chromatographic layer, plotted versus time. In these figures, the gas or gases arrive above the chromatographic layer at time 0.

Figure 40:
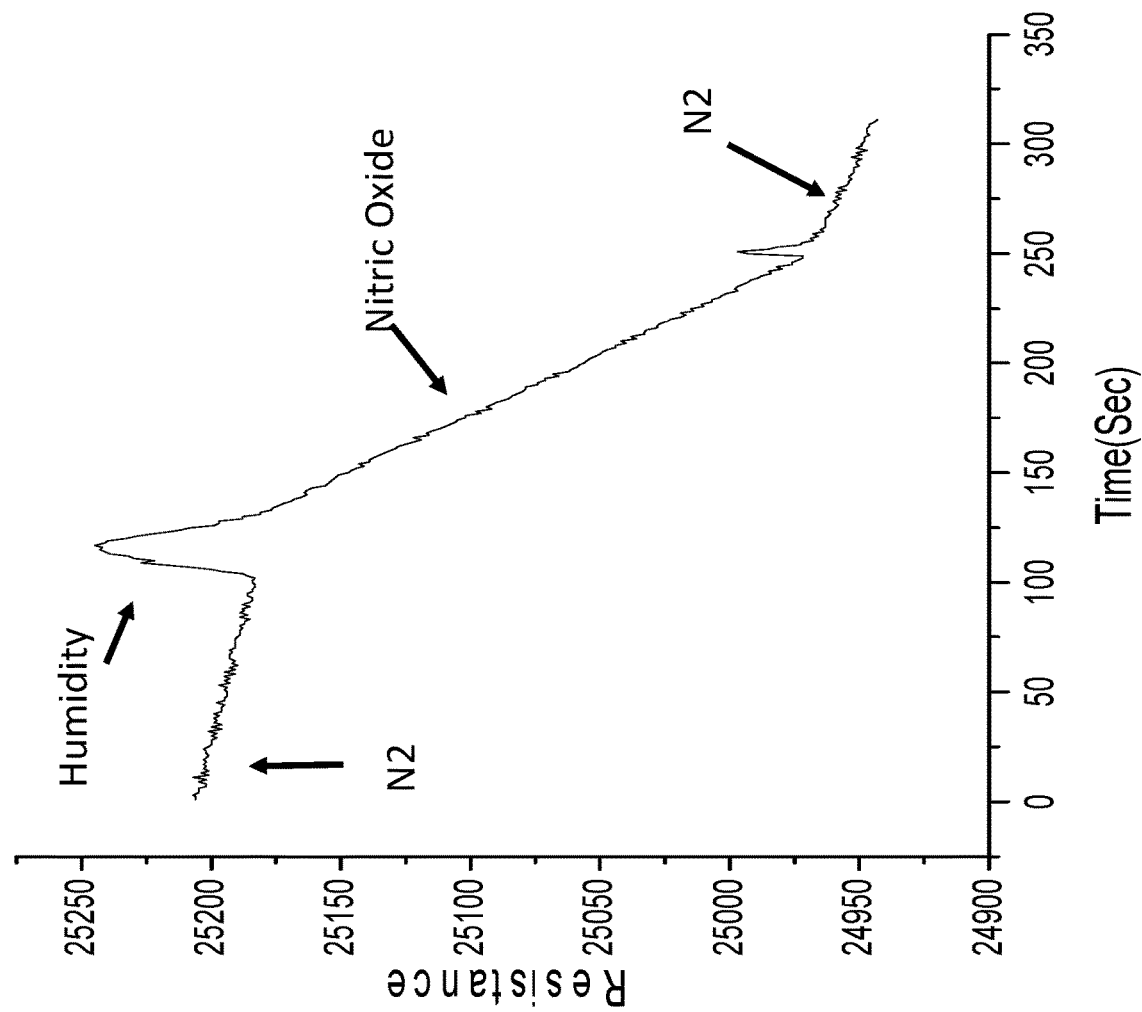
FIG. 40 demonstrates a multi gas signal from the test strip.

FIG. 40 represents the signal output of one embodiment of a test strip with chromatographic layer. The sensor is placed in a stream of nitrogen then exposed to a mixed gas stream consisting of humidity and nitric oxide. Humidity is the first gas to pass through the chromatographic layer and causes an increase in resistance of the sensor. Nitric oxide then follows and causes a sharp decrease in resistance until nitrogen is re-introduced. In this example N2 could also be ambient air and nitric oxide may be oxidized to nitrogen dioxide.

Figure 41:
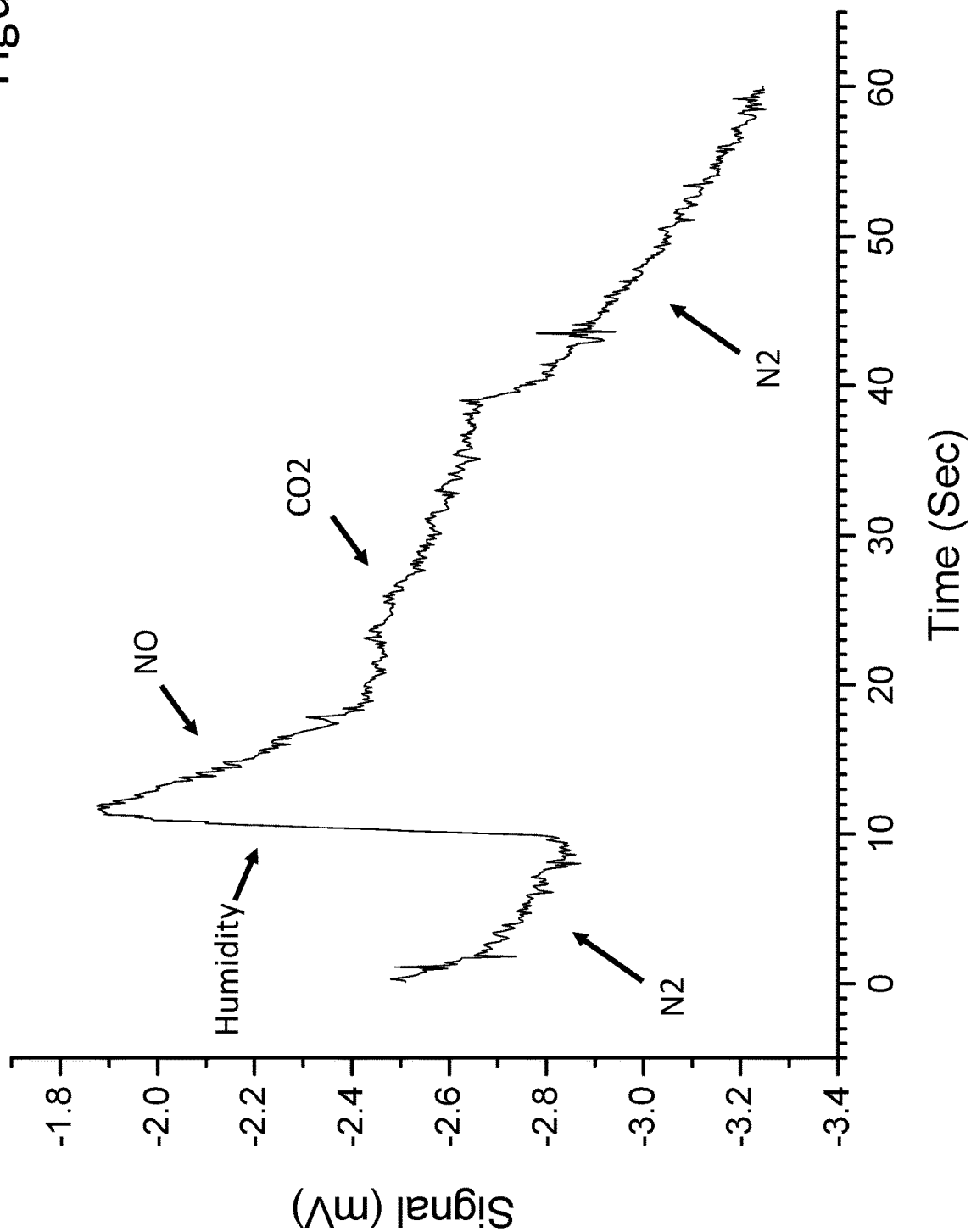
FIG. 41 demonstrates a multi gas signal from the test strip.

FIG. 41 demonstrates another embodiment of the signal output of the test strip with chromatographic layer. The sensor is placed in a stream of nitrogen then exposed to a mixed gas stream consisting of humidity, nitric oxide and carbon dioxide. Humidity is the first gas to pass through the chromatographic layer and causes an increase in resistance of the sensor. Nitric oxide then follows and causes a sharp decrease in resistance. Carbon dioxide is the third gas to pass through the layer causing a change in slope until nitrogen is re-introduced.

Figure 42:
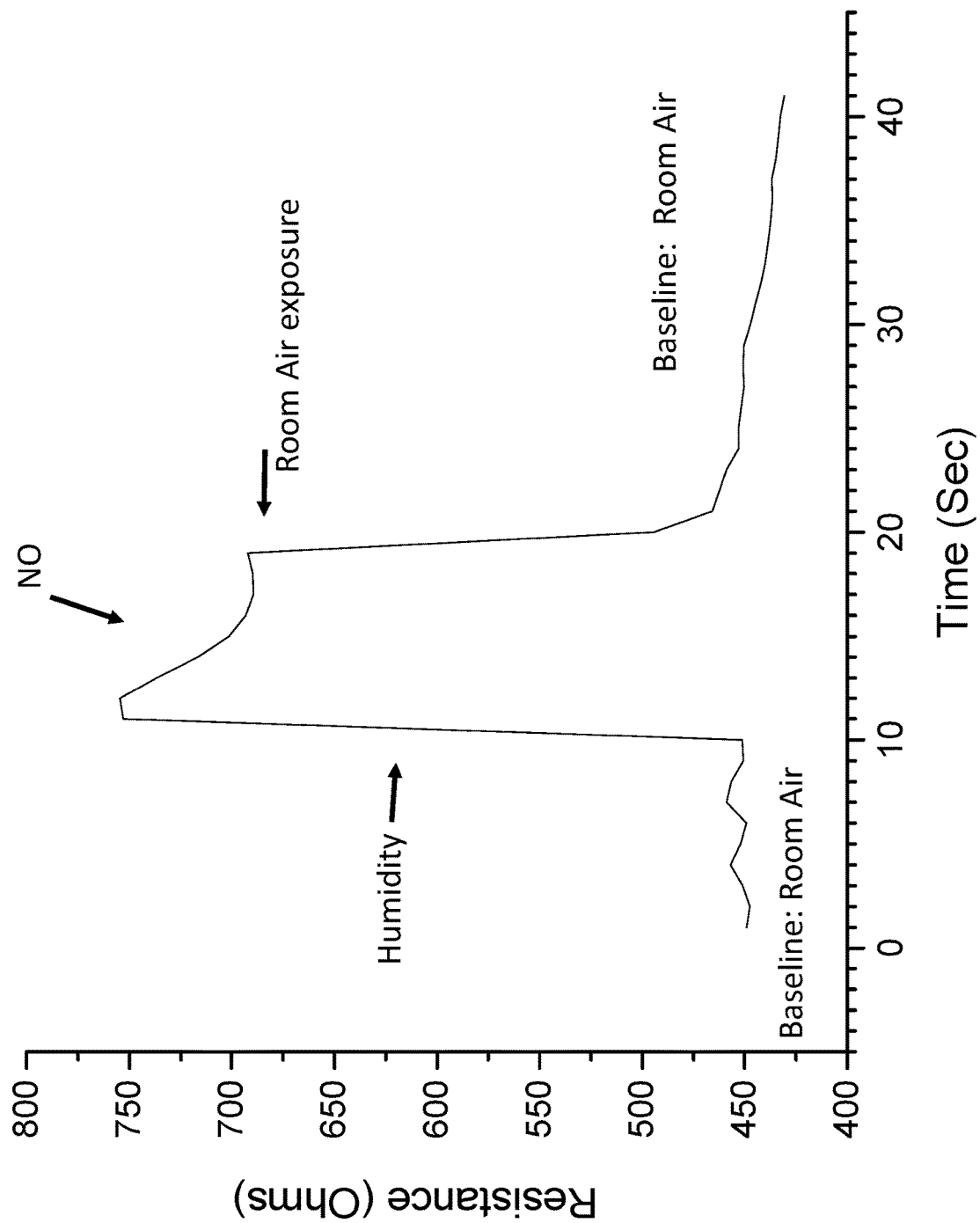
FIGS. 42, 43, and 44 demonstrates a multi gas signal from the test strip in response to human breath.

FIG. 42 is an example of the response of one embodiment of the test strip with chromatographic layer to a human breath. The sensor and chromatographic layer are configured to be sensitive and specific to nitrogen monoxide. Humidity is the primary known interferent in human breath based on the specific sensing chemistry and test strip configuration. The sensor is baselined in room air. The breath stream is introduced and humidity is the first gas to pass through the chromatographic layer causing a sharp initial increase in resistance. The chromatographic layer is designed to exclude the other known gases in exhaled breath. Nitric oxide is the second gas to hit the sensor causing a decrease in resistance. The sensor is then re-exposed to room air. Examples of signal characteristics that are of interest include but are not limited to the initial slope of gas exposure, slope during gas exposure, initial slope of the return signal, slope at the end of gas exposure, changes in slope at various times, absolute changes in sensor properties (physical, electronic optical etc.), overshoot or undershoot from baseline before and after gas exposure, overshoot or undershoot from a calibration curve and regression lines at points in time when gases pass through the chromatographic layer.

Figure 43:
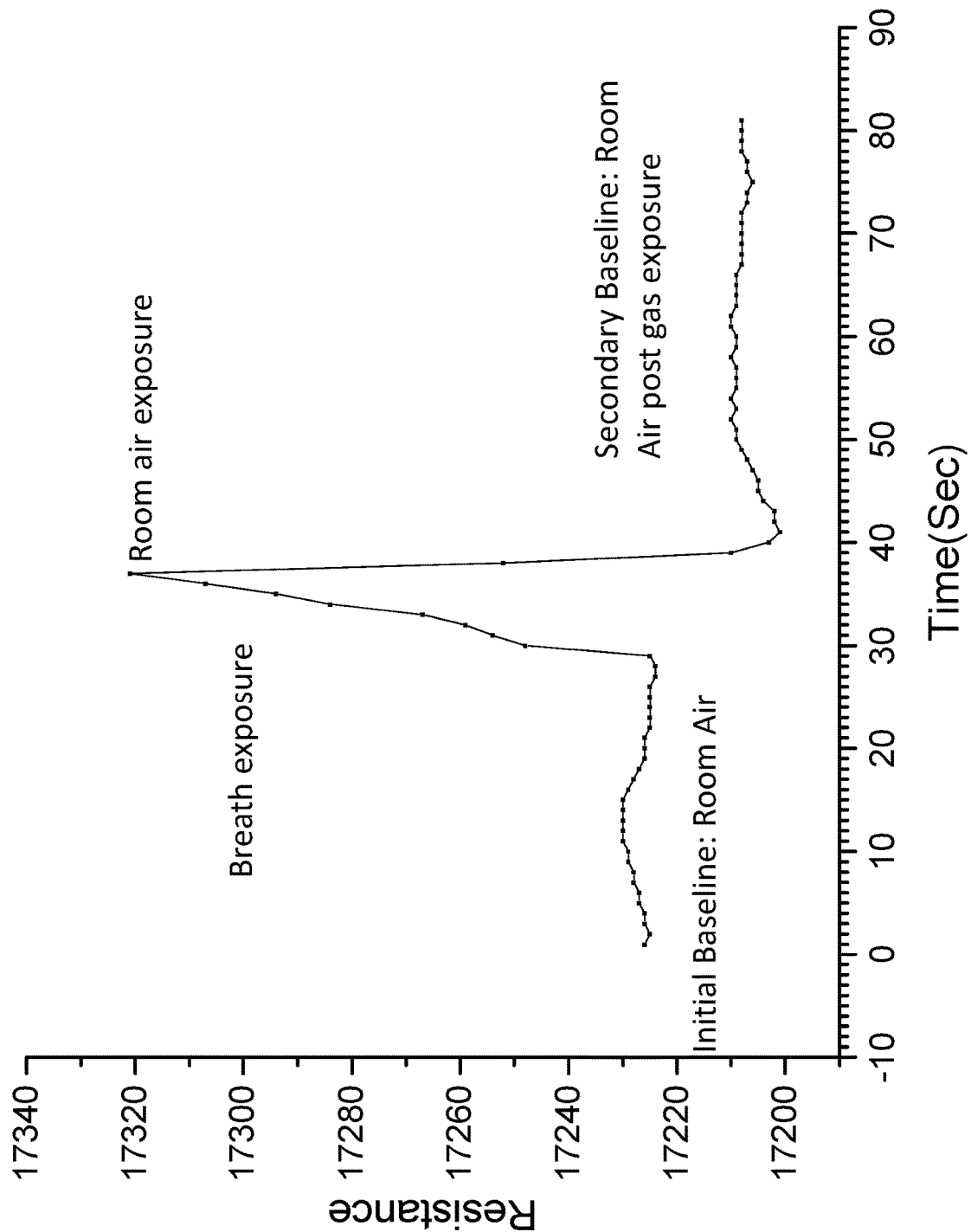

FIG. 43 is an example of the response of one embodiment of the test strip with chromatographic layer to a human breath. The sensor is configured to be sensitive to nitric oxide. The chromatographic layer is designed to exclude all interfering substances except humidity which adsorbs and desorbs predictably from the sensor. The sensor is baselined in room air. The breath stream is introduced and both humidity and nitric oxide pass through the chromatographic layer causing a sharp initial increase in resistance due to the humidity component. The sensor is then re-exposed to room air and the secondary baseline is compared to the initial baseline to determine the quantity of gas that has interacted with the sensor. Other examples of signal characteristics that are of interest include but are not limited to the initial slope of gas exposure, slope during gas exposure, initial slope of the return signal, slope at the end of gas exposure, changes in slope at various times, absolute changes in sensor properties (physical, electronic optical etc.), overshoot or undershoot from baseline before and after gas exposure, overshoot or undershoot from a calibration curve and regression lines at points in time when gases pass through the chromatographic layer.

Figure 44:
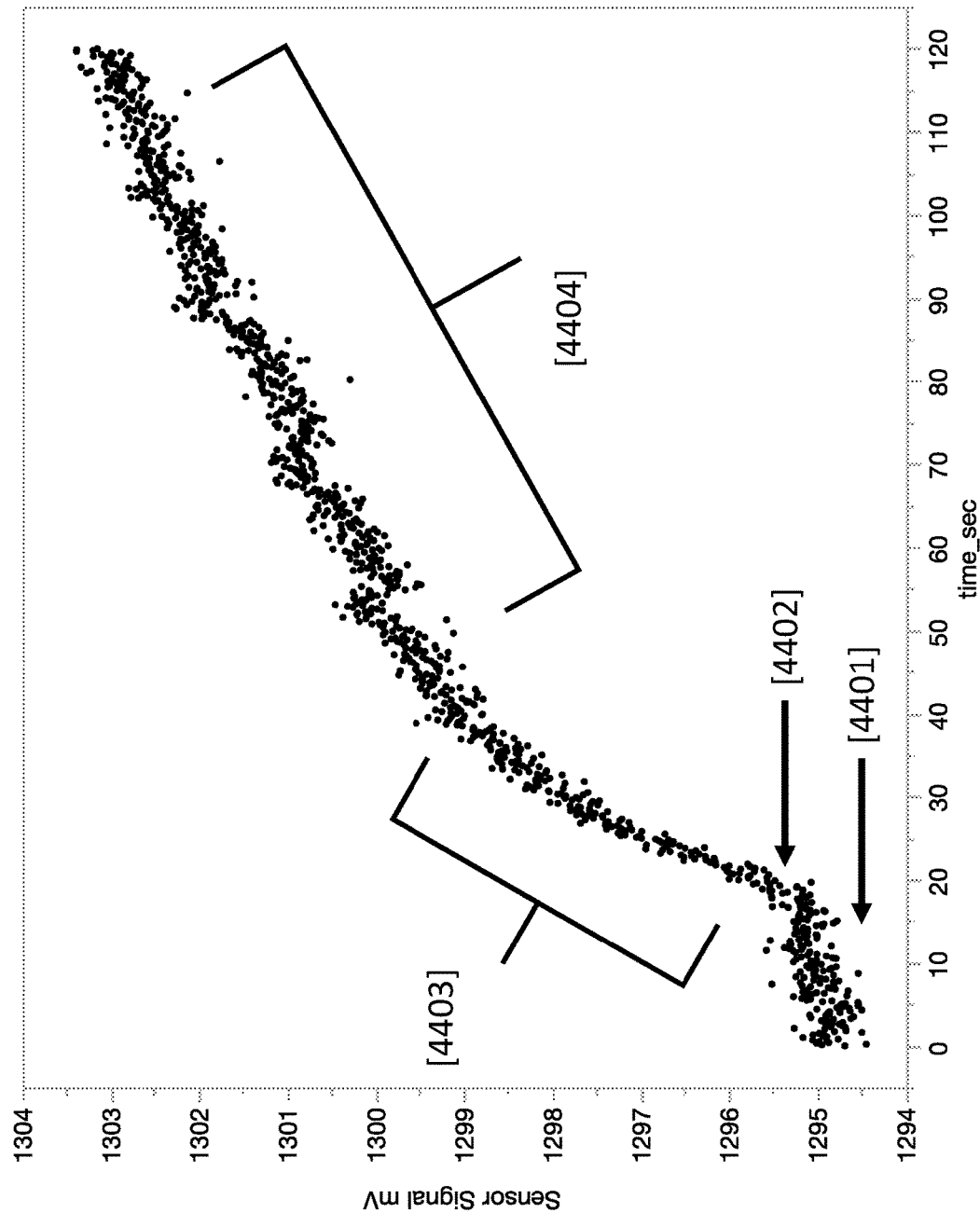

FIG. 44 is another example of the response of one embodiment of the test strip with chromatographic layer to a human breath. The sensing chemistry, sensor and chromatographic layer is configured to be sensitive to nitrogen dioxide and the conversion chamber in the device is designed to oxidize nitrogen monoxide into nitrogen dioxide. Humidity is the primary known interferent in human breath based on the specific sensing chemistry and test strip configuration. The sensor is baselined in room air [4401]. The breath stream is introduced and humidity [4403] is the first gas to pass through the chromatographic layer causing an initial increase in resistance. The chromatographic layer is designed to exclude the other known gases in exhaled breath. Nitrogen dioxide is the second gas to hit the sensor [4404] causing a change in slope versus humidity [4403]. In other embodiments, a layer in the test strip oxidize nitrogen monoxide [4404] to nitrogen dioxide. In other embodiments, the sensor is sensitive to nitrogen monoxide. Other examples of signal characteristics that are of interest include but are not limited to the initial slope of gas exposure, slope during gas exposure, initial slope of the return signal, slope at the end of gas exposure, changes in slope at various times, absolute changes in sensor properties (physical, electronic optical etc.), overshoot or undershoot from baseline before and after gas exposure, overshoot or undershoot from a calibration curve and regression lines at points in time when gases pass through the chromatographic layer.

In another embodiment, the test strip and reader may be configured to measure a gas concentration in breath or flatulence that is the result of the interaction between a substance (e.g. fructose, lactose, sucrose, isotopes, etc.) and a human or animal body. Substances may be inserted, ingested, digested, inhaled, injected or transmitted through the dermis (i.e. transdermal patch). Examples include but are not limited to Hydrogen Breath Test (which may also include methane and/or carbon monoxide and/or carbon dioxide measurement) or Urea Breath Test. Other examples may include substances that interact with cancers, tumors, blood, viruses, bacteria, prions, parasites etc. to produce a gas that is measured. In these embodiments, a gas delivery device is optional.

Test Strip—Sensing Chemistry Deposition, Drying Formation and Batch Calibration

Non-limiting examples of deposition methods are listed in FIG. 16. In a preferred embodiment, the appropriate method of deposition and drying is selected so that the sensing chemistry forms a homogeneous electric pathway between the two electrodes. The pathway may in some embodiments be a concentrated assembly comprised of the at least sensing material, and possible any non-volatile additives to the sensing chemistry solution. The geometry of the pathway is unimportant, provided the homogeneity of the deposition is sufficiently uniform among the test strips to result in a sensor performance that meets the required guidelines for precision and reproducibility. In practice, films fail to achieve enough uniformity of sensing material causing variability in baseline resistance and sensor response, requiring each sensor to be individually calibrated. An ideal geometry is the formation of a homogeneous line or coffee-ring. Lines and coffee rings concentrate the sensing material in a small area, and can be made reproducibly enabling the batch calibration of the test strip sensors. For example, in some embodiments, in the case of a ring, the portion of the ring that crosses the electrode gap should have >80% of the material between the electrodes is concentrated within <20% of the electrode gap area that is bounded by the ring. Similarly, a line should have the disposed material concentrated over an area across the gap that is, for example, less than 0.5 mm wide, and crosses the entirety of the gap between electrodes. In either case, additional material may be disposed on the electrode surface (i.e. outside of the electrode gap) in any way desired, as this material does not play a role in sensing analyte. The electrode pairs can have any geometry, e.g. the can be parallel or an interdigitated array.

In one embodiment of the invention, a processor utilizes calibration information to convert the analog signal (e.g. millivolts, resistance, current etc.) into an analyte concentration. In one embodiment, the analog signal is sent to a mobile computing device wherein the software on the mobile or other computing device contains the calibration information to convert the analog signal into an analyte concentration. The processor may receive the calibration information from internal memory, an external chip, SIM card, USB drive, a paired mobile computing device or via a mobile or wireless network. In one embodiment, the test strip may contain electrodes in a specific configuration or of a specific resistance indicating to the device the calibration of the test strip. In another embodiment, a bar code is used to determine the calibration of the test strip. The bar code may be located in any number of places without deviating from the spirit of the invention. Examples include but are not limited to the test strip or packaging. In another embodiment, a RFID tag contains the calibration information. The RFID tag may be located in any number of places without deviating from the spirit of the invention. Examples include but are not limited to the test strip or packaging. In another embodiment, a chip or external memory source is inserted into the device to provide the necessary calibration information. In another embodiment, the calibration or a code representing a calibration is manually entered into the device.

Figure 19:
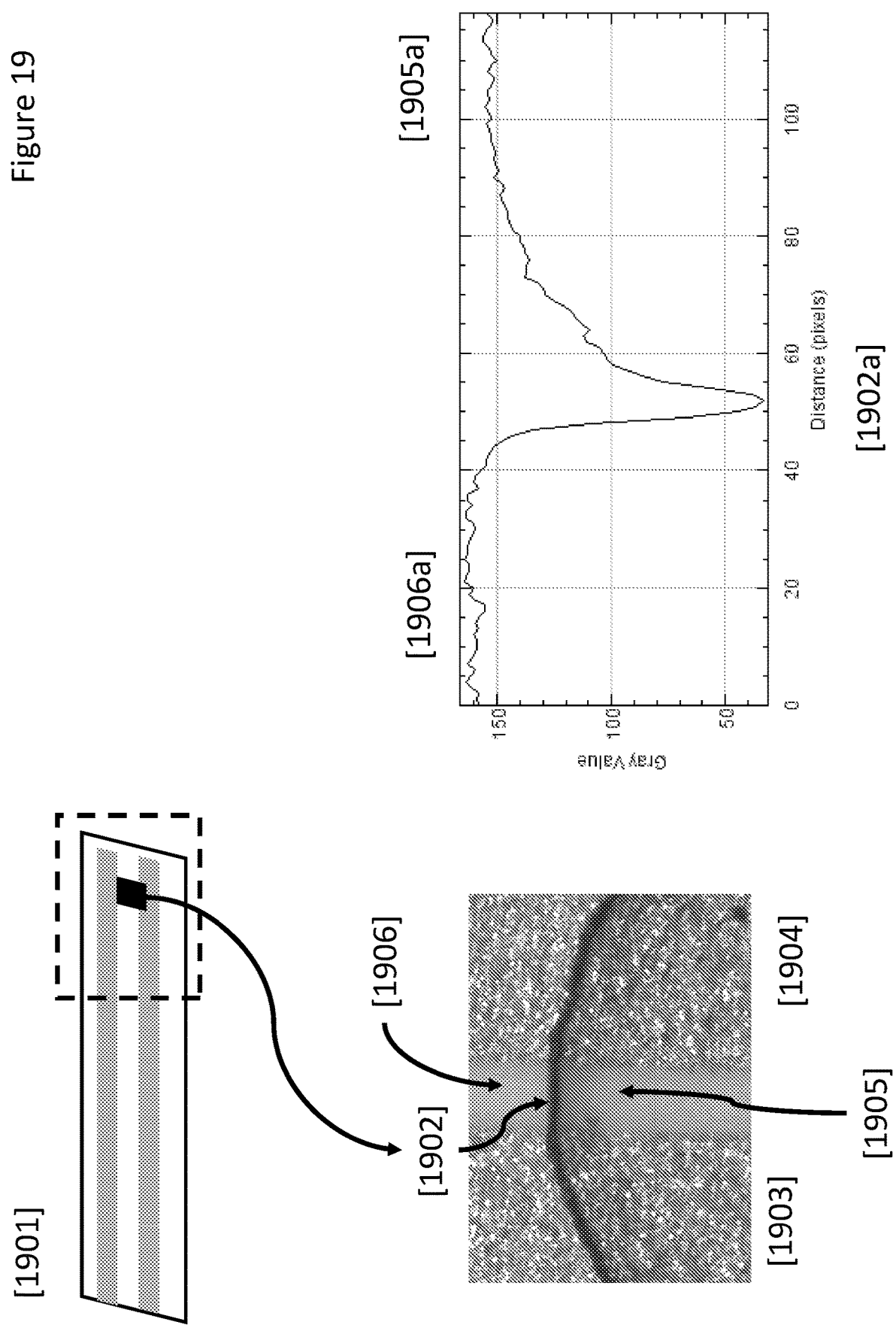
FIG. 19 shows an example of the sensing chemistry configured in a line and in electrical communication with an electrode pair.

FIG. 19 demonstrates an embodiment of a test strip [1901] and a line of sensing chemistry [1902] in electrical communication with an electrode pair [1903] and [1904] shown under magnification. A line is different from a film in that has clearly defined edges bridging the electrode pair. For example, the pixel intensity shown as a grey value [1902a] corresponds with the line of sensing chemistry [1902]. The intensity of [1902a] is distinguishable from the base substrate [1905] with corresponding intensity [1905a] and [1906] with corresponding intensity [1906a]. The lines provide a highly uniform conductive pathway to carry the sensing current across the electrodes and through the sensor material.

Figure 20A:
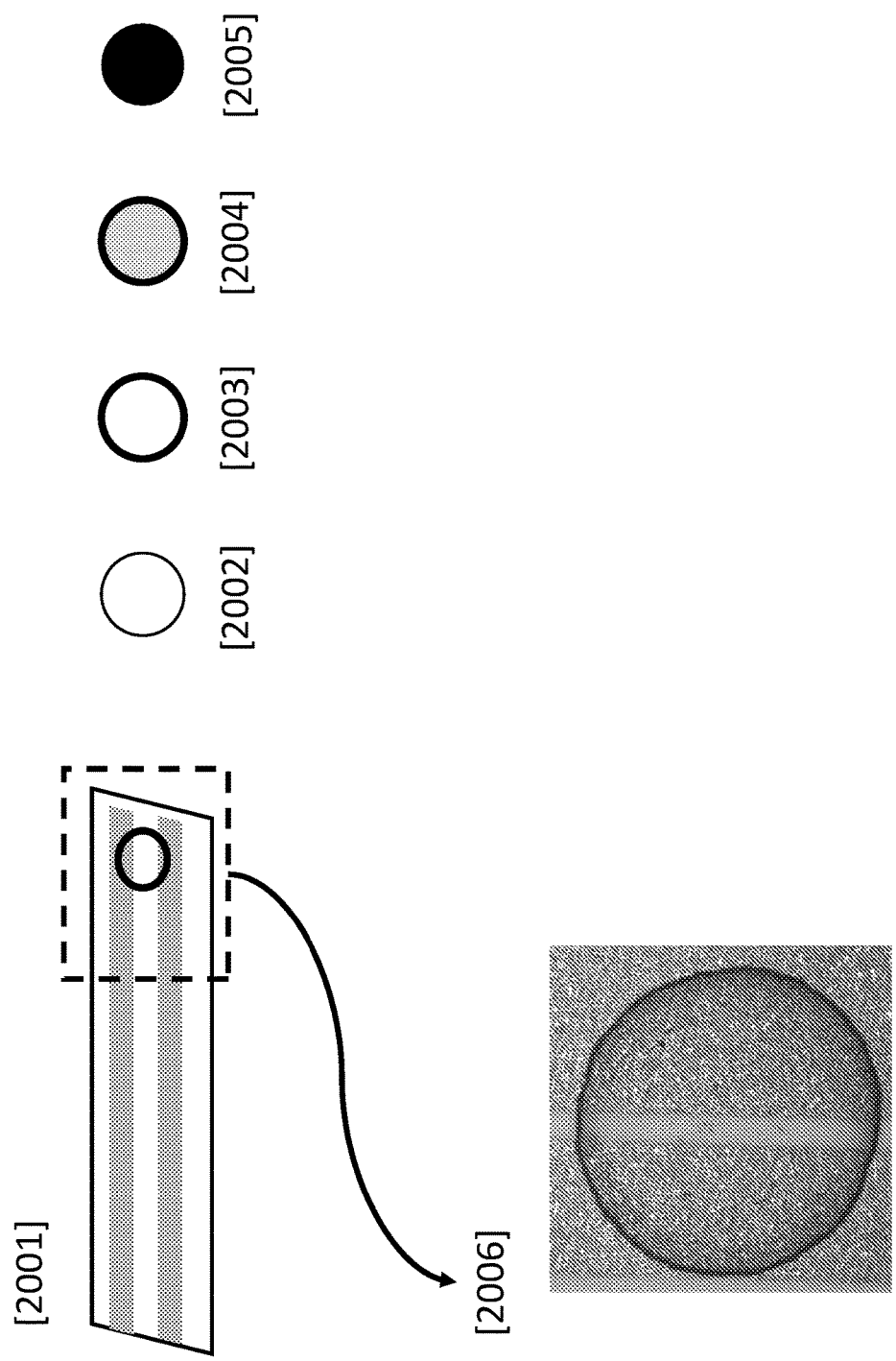
FIGS. 20A-20B define a coffee ring configuration of the sensing chemistry.

FIG. 20A demonstrates another embodiment of test strip [2001] and a sensing chemistry configured in a coffee ring [2006]. A coffee ring has a well-defined, and distinguishable edge [2002], [2003], [2004] versus a film [2005] wherein the edge is not distinguishable from the center. There is a continuum of edge features between an ideal coffee-ring and an ideal film. As the center thickness increases relative to the edge thickness, the coffee-ring approaches a film. Better performance is achieved through the formation of rings that approach an ideal coffee-ring that has all of the sensing material in an infinitely narrow edge, with no material deposited in the center of the spot. The height profile of a line or ring edge shows a rapidly formed peak with no plateau or local minimum at the peak.

Figure 20B:
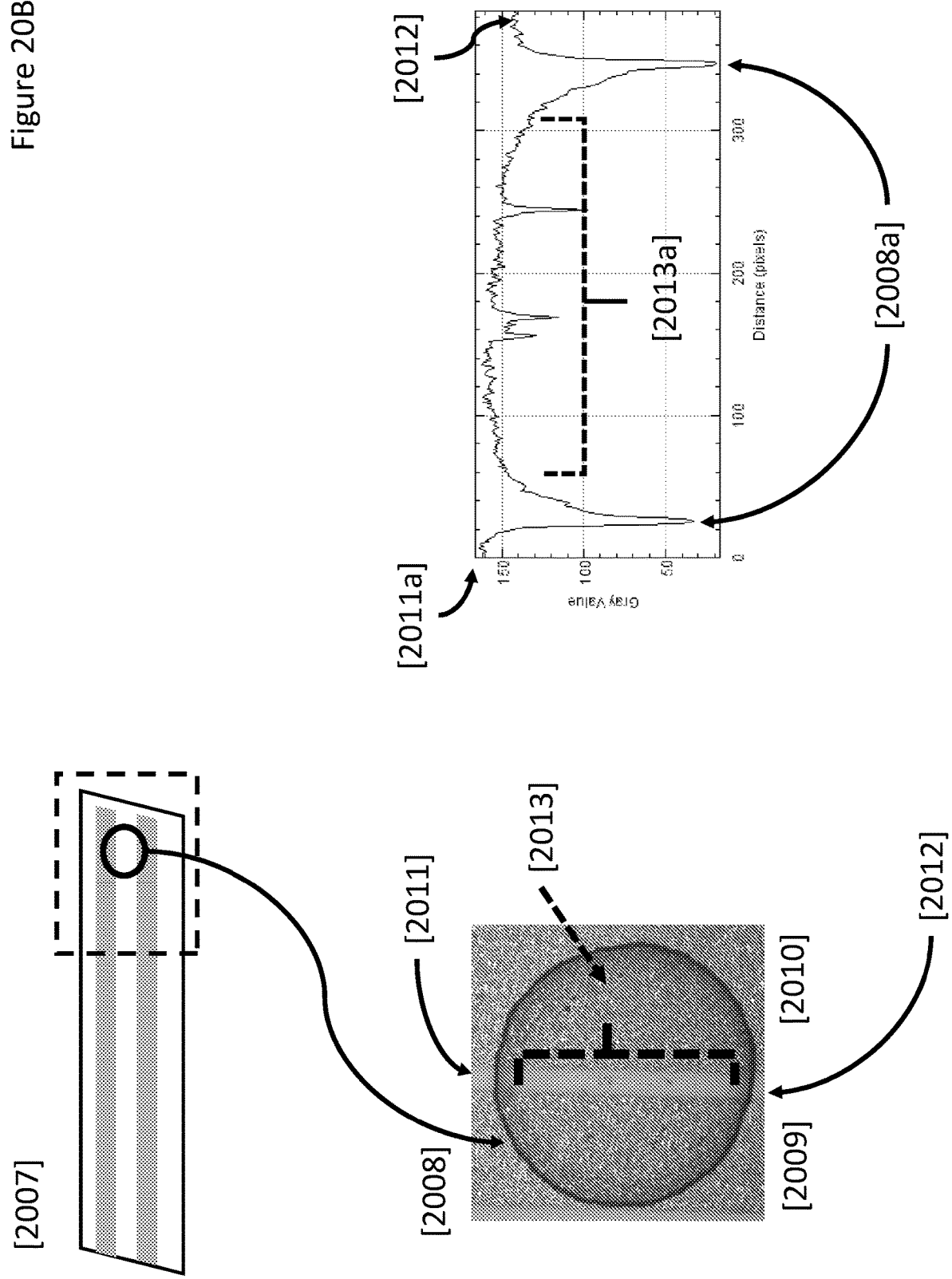

FIG. 20B demonstrates an embodiment of a test strip [2007] and a sensing chemistry configured as a coffee ring [2008]. The sensing chemistry [2008] is in electrical communication with an electrode pair [2009] and [2010]. A coffee ring is different from a film in that it has clearly defined edges bridging the electrode pair. For example, the pixel intensity shown as a grey value [2008a] corresponds with the coffee ring of the sensing chemistry [2008] where it bridges the electrode pair [2009] and [2010]. The intensity of [2008], shown in [2008a], is distinguishable from the base substrate [2011], [2012] and [2013] with corresponding intensities [2011a], [2012a] and [2013a] respectively. In other embodiments, a film may be suitable configuration for the sensing chemistry. A film has a near uniform intensity across the portion that bridges the electrode pair. An example where a film is preferred to a line or coffee ring may include a qualitative or semi quantitative measurement to determine the presence or absence of an analyte.

Figure 21B:
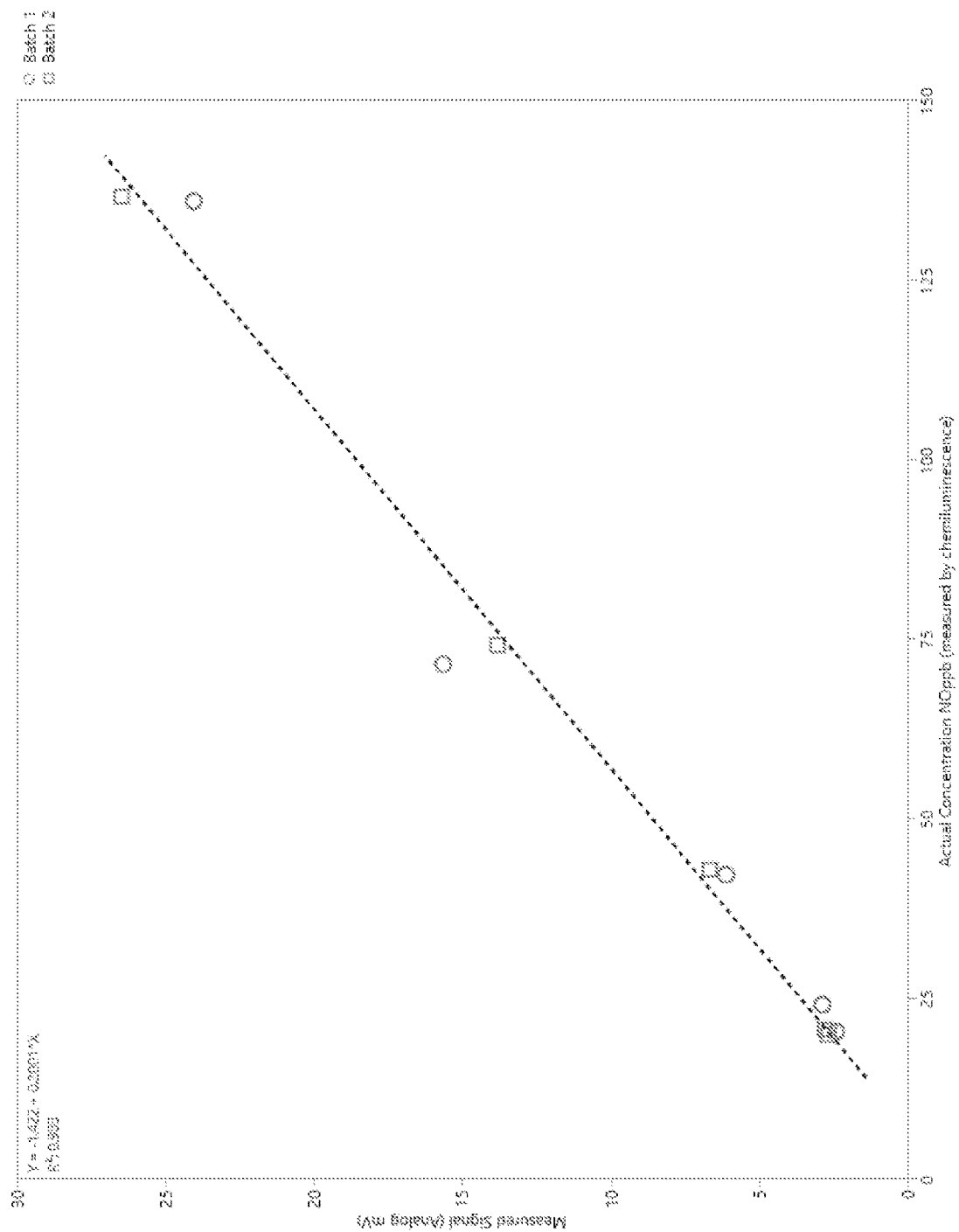
FIG. 21B demonstrates the uniformity and linearity of the analog test strip signal of two batches of sensors within the same manufacturing lot.

FIG. 21A demonstrates the initial baseline signal, measured in millivolts, of two batches of sensors manufactured in the same lot. In this example, the manufacturing lot contains a plurality of sensors/test strips wherein the raw materials, sensing chemistry, and sensing chemistry geometry is sufficiently homogeneous so that the calibration information from a subset of the plurality of test strips (e.g. batch within a lot) applies to the plurality of test strips. In this example [2101], the x-axis represents the 10 individual sensors from a manufacturing lot that has been sub divided into Batch 1 and Batch 2 and the y-axis is the corresponding baseline analog signal in mV. The corresponding descriptive statistics [2103] demonstrate a coefficient of variation (CV) of 8.87% across the baseline signal of the two batches. FIG. 21B is the corresponding analog output in millivolts of the 10 sensors in the manufacturing lot that have been divided into Batch 1 and Batch 2 plotted on the y-axis versus the actual concentration as measured by chemiluminescence plotted on the x-axis. This example shows that the analog signal of uncalibrated sensors of the same manufacturing lot have a strong correlation (r-squared>0.983) with the actual analyte concentration as measured by chemiluminescence. In this example the analyte of interest is nitric oxide or nitrogen dioxide. However, it is not the particular type or configuration of chemistry, but the high uniformity/homogeneity among the sensors that allows for the batch calibration.

Figure 22A:
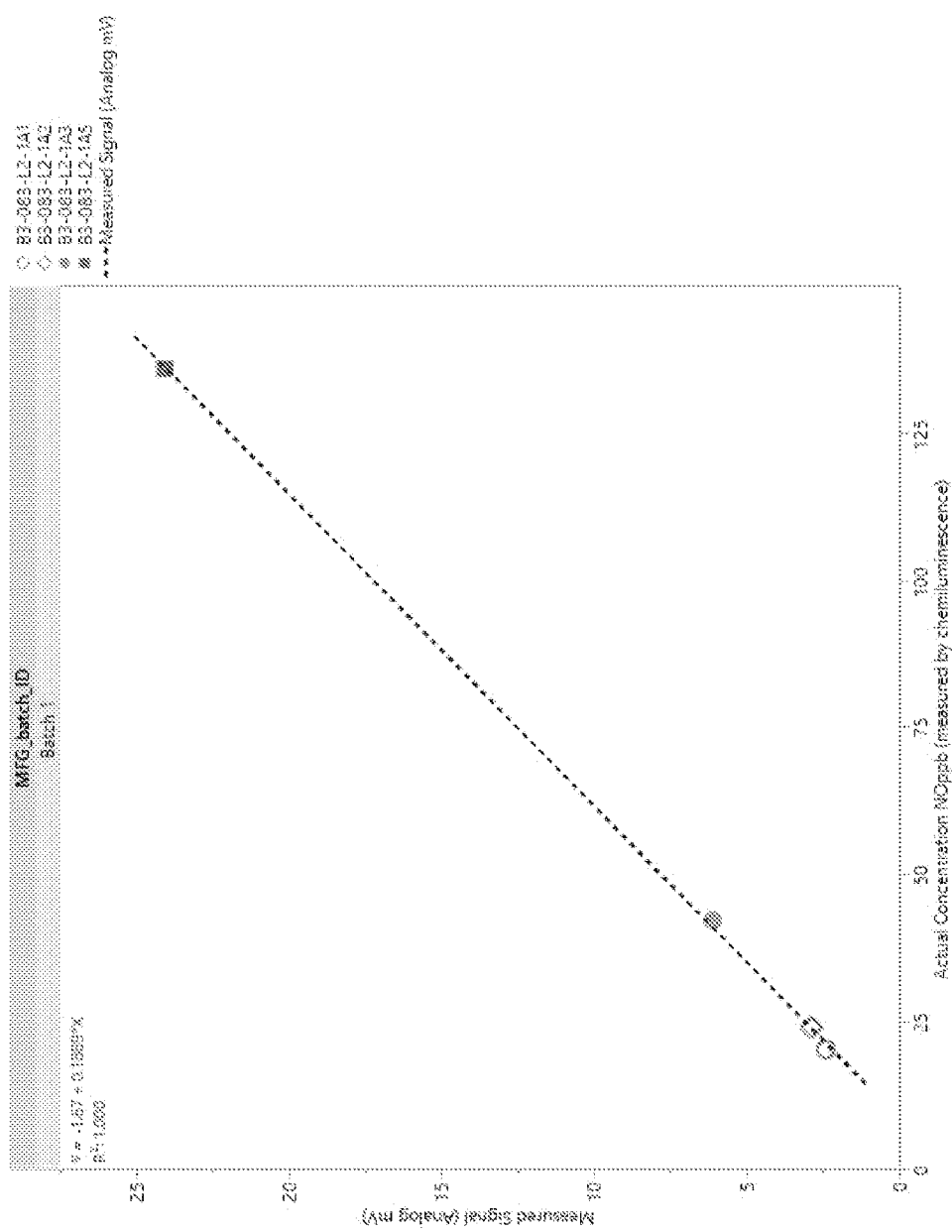
FIG. 22A demonstrates an example of a calibration curve derived from a batch of sensors within a manufacturing lot.
Figure 22B:
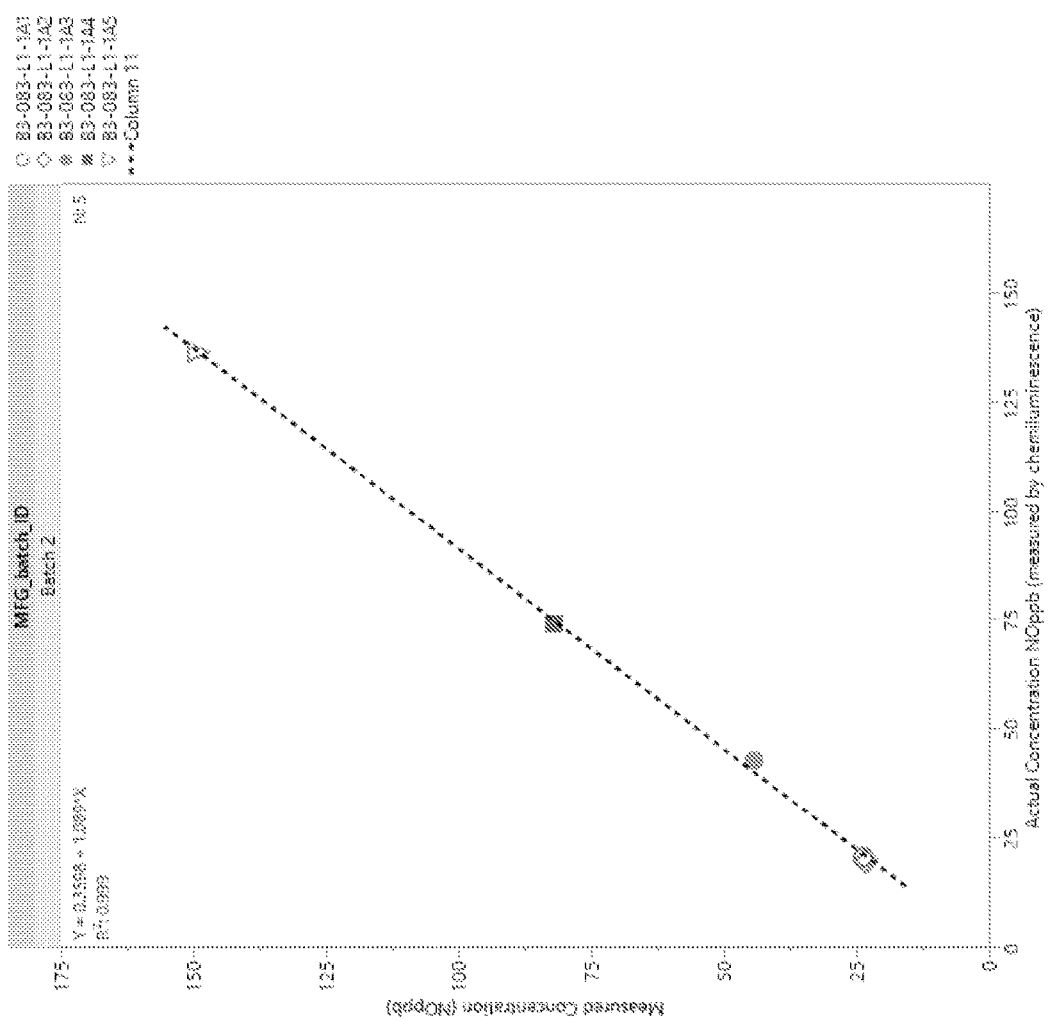
FIG. 22B demonstrates an example of the measured response of a batch of sensors wherein the analog signal is converted into a concentration using a calibration equation derived from a different batch of sensors within the same manufacturing lot.

Batch calibration involves selecting a predetermined number of sensors from a manufacturing lot and/or batch and creating a standard curve based on the sensors' response to known concentrations across a relevant range. The equation that defines the standard curve accurately converts the sensor analog signal to a concentration when the input concentration is unknown. The standard curve or calibration equation holds true for at least a group of the sensors in a manufacturing lot or batch. For example, the manufacturing lot in FIG. 21A is divided into two batches of 5 sensors (Batch 1 and Batch 2). Sensors are selected from Batch 1 to create a calibration curve for Batch 2. When Batch 2 is exposed to an unknown analyte concentration, the calibration equation from Batch 1 is used to convert the analog signal of Batch 2 into a measured analyte concentration. FIG. 22A demonstrates batch calibration using 4 of the 5 sensors from Batch 1 to build a 4 point standard curve. Any number of sensors may be used to build the standard curve without deviating from the spirit of the invention. The y-axis represents the measured analog signal in millivolts of four sensors in Batch 1 versus the actual concentration as measured by chemiluminescence plotted on the x-axis. Linear regression yields a fit of Y=−1.67+0.1889*X and a correlation coefficient of 1. The equation is rearranged because the actual concentration (x-axis) is unknown in a real-world setting. The corresponding calibration curve is Unknown Concentration=(AnalogSignal—Intercept)/Slope. Other non-linear calibration equations are possible without deviating from the spirit of the invention as are calibration equations that take into account environmental parameters such as temperature, pressure and/or humidity. FIG. 22B demonstrates the application of the calibration curve derived from Batch 1 (FIG. 22A) to the remaining 5 sensors in the manufacturing lot (previously sub-divided into Batch 2 in FIG. 21A and FIG. 21B). In this example, the Batch 2 sensors have not been individually calibrated and are exposed to an unknown concentration of the analyte. The calibration curve derived from Batch 1 is used to convert the analog signal into a measured concentration for the Batch 2 sensors. In this example, the measured concentration is plotted on the y-axis versus the actual concentration, as measured by chemiluminescence, plotted on the x-axis. The resulting regression equation is Y=0.3598+1.098*X with a correlation coefficient of 0.999.

In another embodiment, a manufacturing lot containing a plurality of sensors/test strips wherein the raw materials, sensing chemistry, and sensing chemistry geometry is sufficiently homogeneous so that the calibration information from a subset of the plurality of test strips (e.g. batch within a lot) applies to the plurality of test strips. In this example, 40 sensors are manufactured and divided into 4 sub-batches containing 10 sensors each. 5 of the sensors from each sub-batch are selected to create a calibration curve using the same method previously described.

|  | Batch 1 | Batch 2 | Batch 3 | Batch 4 |
| --- | --- | --- | --- | --- |
| Total sensors in Batch | 10 | 10 | 10 | 10 |
| Sensors Selected for Calibration | 5 | 5 | 5 | 5 |
| Regression Equations | Y = 1.908 + 0.2943* X | Y = 0.1156 + 0.3594* X | 0.1689 + 0.3311* X | −8.031 + 0.5673* X |
| r-squared | 0.997 | 0.977 | 0.99 | 0.974 |
| Calibration Equation: Concentration = (AnalogSignal − Intercept)/Slope | X = (Y − 1.908)/ 0.2943 | X = (Y − 0.1156)/ 0.3584 | X = (Y − 016689)/ 0.3311 | X = (Y − (−8.031))/ 0.5673 |

The calibration equation derived from the 5 selected sensors in each sub-batch is then applied to the remaining 5 sensors in the corresponding sub-batch. The remaining 5 sensors in each batch, which have not been individually calibrated, are exposed to an unknown analyte concentration. The analog signal is converted into a measured concentration using the corresponding calibration equation (e.g. Batch 1 sensors use X=(Y−−1.908)/0.2943)). The resulting regression analysis of measured concentration plotted versus actual concentration is described by the equation Y=0.7114+0.9859*X and has a correlation coefficient of 0.986 for the remaining 20 sensors in the original manufacturing lot. Other embodiments of the invention include correlation coefficients greater than 0.8, 0.85, 0.9, 0.95, 0.96, 0.97, 0.98, 0.99. For example, with regard to some embodiments system, the sensing chemistry pathway geometry of each of a plurality of the test strips is sufficiently homogenous so that calibration information from a first subset of calibrated test strips of the plurality of test strips applies to a second subset of uncalibrated test strips of the plurality of test strips with a correlation coefficient of at least 0.9, wherein the calibration information associates electrical signals of the test strips with measured concentrations of the analyte and the correlation coefficient measures an accuracy of measured concentrations of the analyte relative to actual concentrations of the analyte.

Figure 23:
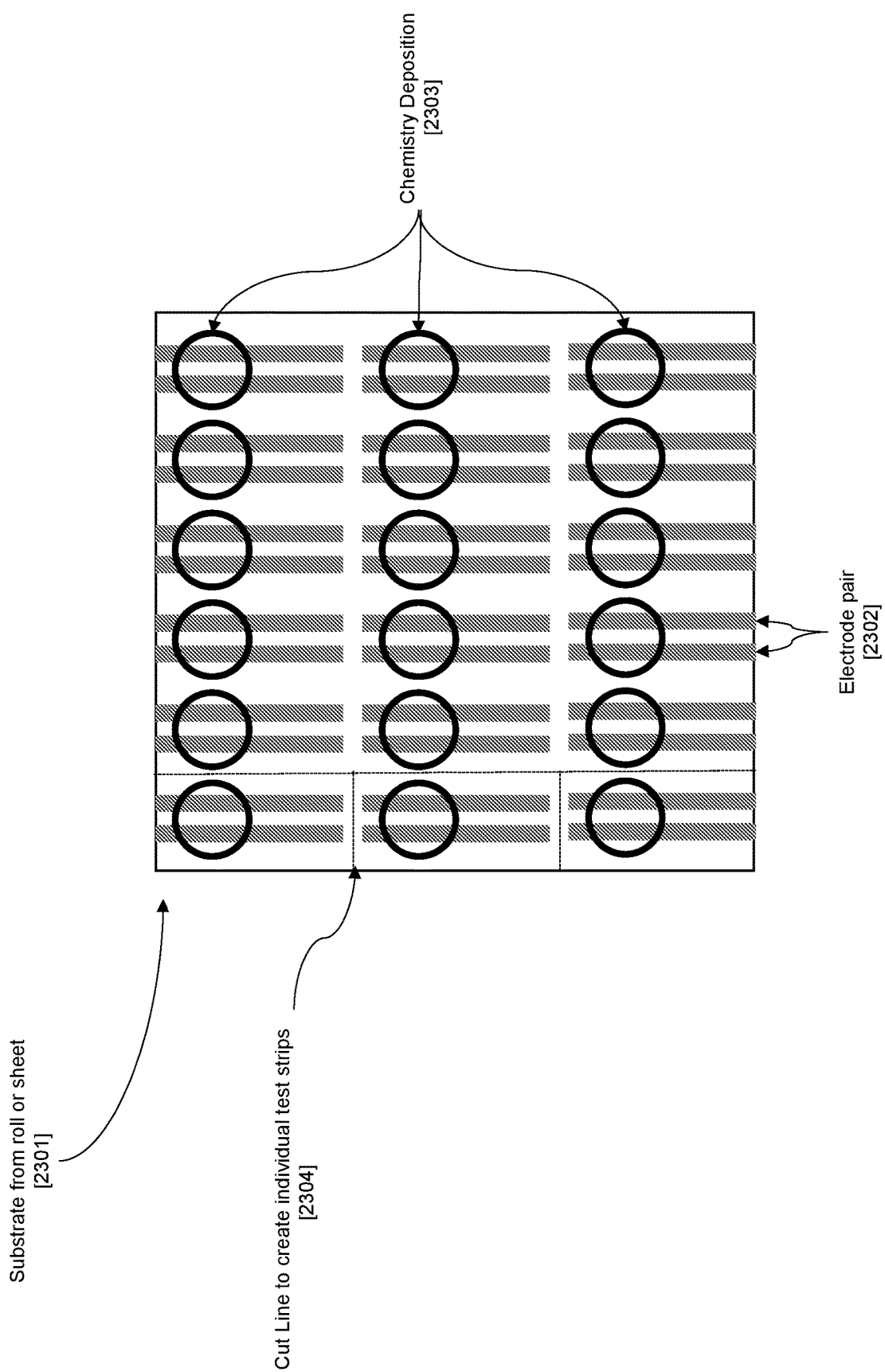
FIG. 23 depicts multiple test strips manufactured on a single substrate.

FIG. 23 shows a layout of the test strips for mass production. A continuous substrate from a roll or sheet [2301] is supplied for chemistry deposition. The substrate may already include electrodes [2302] or the electrodes may be created during the manufacturing process (i.e. screen printed or laser ablation). The chemistry [2303] is deposited on the substrate using any number of methods and coating techniques listed in FIG. 16. This is not intended to be an exhaustive list. Individual test strips [2304] are cut using methods known in the art (e.g. die cut, rotary cut, laser cut etc.). Two chemistries can also be deposited (not shown) on a substrate from a roll or sheet. Any number of rows are possible without deviating from the spirit of the invention. A sheet containing electrodes is fed into a machine designed to deposit the chemistry. The sheets with the chemistry are then dried by any number of methods. Examples include but are not limited to air drying, convection, heat, infra-red, ultraviolet etc. One of skill in the art would appreciate that the additional layers contain pressure or heat sensitive materials those layers may also be applied. The sheets may be cut into smaller strips [2304] by any number of methods known in the art (e.g. die cut).

Figure 24:
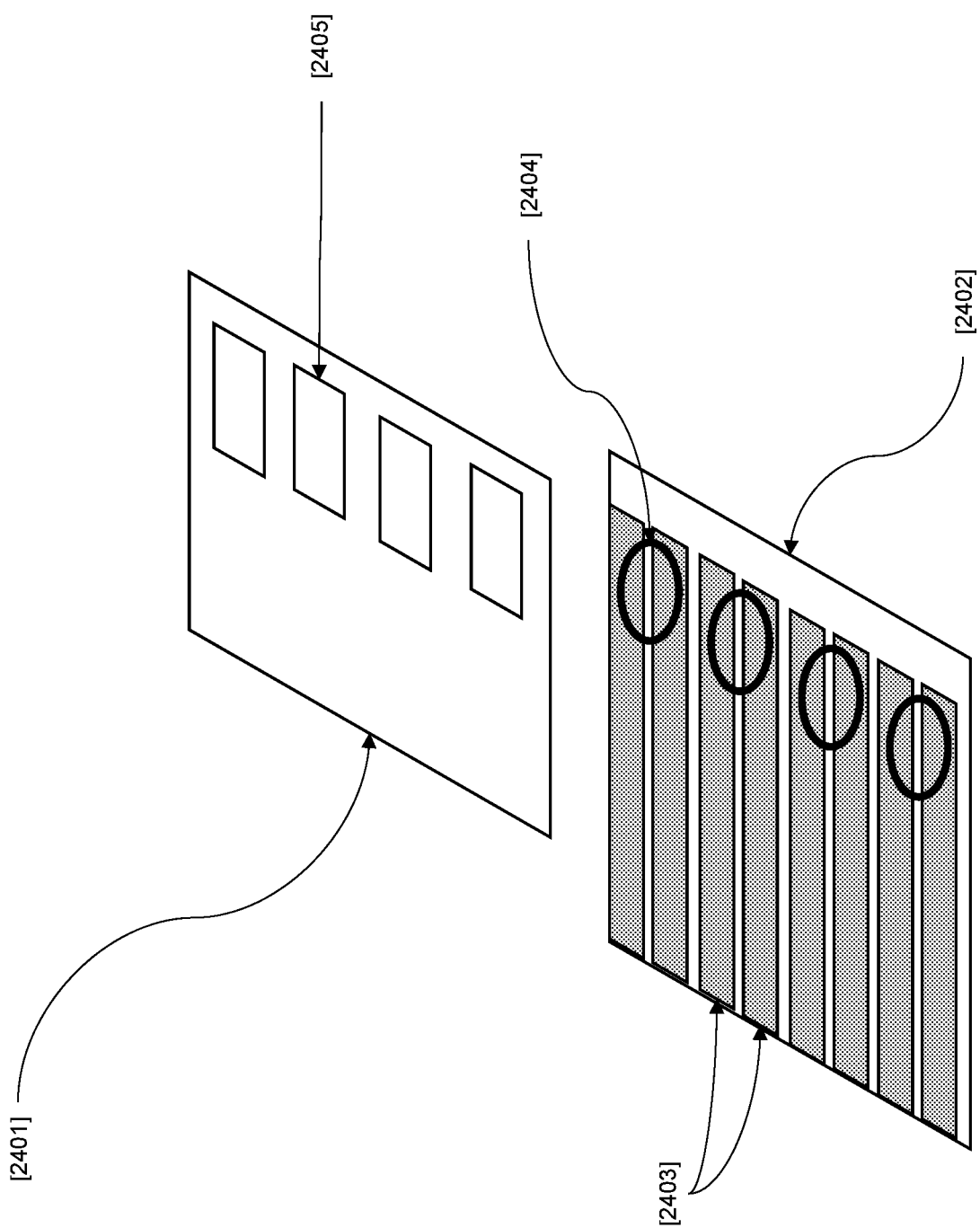
FIG. 24 depicts the addition of at least one layer to the substrate containing multiple sensors.

FIG. 24 shows a layer [2401] disposed above the sensing chemistry [2404], electrode pair [2403], and substrate [2402]. The layer has a window [2405] to enable the analyte of interest to reach the sensing chemistry. In some embodiments, the layer contains an adhesive. In a preferred embodiment, the layer contains a pressure sensitive adhesive.

In some embodiments, a layer that covers the sensing chemistry is substantially permeable to the analyte of interest. In some embodiments one of the layers is a blocking layer that covers the reference sensing chemistry and has a window which exposes the active sensing chemistry. In some embodiments, the blocking layer may include an adhesive. One of skill in the art would understand that any of a number of adhesives would be adequate, including but not limited to a heat sensitive adhesive or a pressure sensitive adhesive.

In some embodiments one layer may be a membrane layer that is selectively permeable to at least one analyte. One of skill in the art would understand that a membrane layer could comprise a number of different materials, including but not limited to porous polymers, non-porous polymers, composite materials, fibrous materials, woven textiles, non-woven textiles, polymers, adhesives, films, gels, PTFE, and silicone. In some embodiments, a silicone transfer layer may be used to attach the membrane layer to at least one other layer.

The examples incorporated herein primarily relate to gas detection however, the concepts, chemistries, and sensor designs described may also apply to detecting other fluids, analytes etc. without deviating from the spirit of the invention. The concepts, chemistries, and sensor designs described in this invention may also apply to detecting other gases, fluids, analytes etc. without deviating from the spirit of the invention. This following list provides examples of such applications. The list is not intended to be exhaustive. Industries (non-exhaustive list): Industrial, Automotive, Environmental, Military, Agricultural, Veterinary, and Medical. Within the Medical Industry specific examples (non-exhaustive list) include: 1) Health diagnostics related to the following areas (non-exhaustive list), Clinical chemistry & immunoassays, Breath analysis, Hematology & hemostasis, Urinanalysis, Molecular diagnostics, Tissue diagnostics, Point-of-care diagnostics, Exhaled Breath and/or Condensate, Virology, Analysis of Proteins and/or Antibodies, DNA/RNA, Oncology, Cardiology & metabolism, Infectious diseases, Inflammatory & autoimmune, Women's health, Critical care, and Toxicology; 2) Techniques (non-exhaustive list) including, Polymerase chain reaction (PCR & qPCR), Nucleic Acid Amplification, ELISA, and Fluorescence; and 3) Specific Diseases (non-exhaustive list) including, STDs, Breath tests, Digestive Disorders, Urinary LTE4, MRSA, Influenza, Viral detection, and Bacterial detection.

The above techniques, devices, and systems have been described with reference to detecting an analyte in exhaled breath of a patient. However, the techniques devices, and systems are also useful in any application in which it is desirable to detect the presence and/or amount of particular compounds in a gaseous stream, such as the industrial, automotive, environmental, military, fire and safety, agricultural, and veterinary fields.

Examples of industrial applications include but are not limited to industries such as oil and gas, manufacturing process, power generation, chemicals, basic materials, mining, commercial building etc. One embodiment of the device is used to detect dangerous gases in coal mine and is worn by miners. In another embodiment, the test strip is configured to measure gases for quality control purposes in manufacturing processes that require high purity gases.

Examples of automotive applications include but are not limited to monitoring air quality in the cabin of the automobile and/or monitoring the exhaust stream from the engine.

Examples of environmental applications include home safety, air pollution and air quality. In one embodiment, the test strip and reader is placed in multiple locations in an urban area, and the data is transmitted to a central location to monitor air quality.

Examples in the agricultural industry include but are not limited to agricultural production and the food packaging and processing industry. In one embodiment, the test strip and Reader is packaged with food to monitor spoilage. In another embodiment, the test strip is part of a RFID tag which is packaged with the food to monitor spoilage and read remotely. In another embodiment, the test strip and Reader is configured to measure methane or other gas concentrations in waste of livestock.

In one embodiment in the military and fire and safety industry, the test strip is combined with a robot/drone or other means, such as a ball that can be thrown. The test strip is then sent into an area without the need for a human presence to detect gases of interest.

In another embodiment for medical use, physicians are able to use the invention to monitor the effectiveness of their prescribed therapy and search for the most effective therapies based on individual patient characteristics. The system provides this information by tracking trends in gathered data (i.e. symptoms, biomarkers etc.) and correlating that information to prescribed therapies. The system may compare the effectiveness of therapies across the collection of patients or a single patient. The system would allow a physician to enter the characteristics of an individual patient and implementations of the invention would find like patients and display therapies that were both successful and unsuccessful. This allows the physician to input characteristics about a given patient and access successful treatment protocols from the population in the collection to reduce the need for trial and error.

Physicians may also use the invention to identify root causes of patients' symptoms. In this embodiment, the system may compare trends in symptom and biological data, correlate it to the prescribed therapy, check against environmental data and/or prescription usage.

Other embodiments use the gathered information to compare drug effectiveness, monitor adherence to therapy, create risk reports (i.e. for underwriting purposes) or establish payment based on outcomes.

Other embodiments use the gathered information to determine the optimal dose of a drug or drugs based on patient response to treatment as determined by biomarker values or a combination of information gathered by the invention. Examples of biomarkers include but is not limited to serum periostin, exhaled nitric oxide, DPP4, blood eosinophils, blood neutrophils, sputum eosinophils, IgE, or other biomarkers indicative of the presence or absence of eosinophilic, neutrophilic, paucigranulocytic, mixed granulocytic, Th2 or Th1 type inflammation.

Other embodiments use a biomarker or a combination of biomarkers to predict drug response. Biomarker measurements may be taken at a single point in time or across multiple points. Examples of biomarkers have been previously described although it is not intended to be an exhaustive list. Examples of drug response may be defined as improvement in lung function, reduction in exacerbations, reduction in the need for steroids or rescue medications. Drugs may include those therapies designed to treat chronic respiratory disease.

Other embodiments use the gathered information to determine patient compliance or adherence to therapy. Compliance may be determined by taking one or multiple measurements of one or several biomarkers over time and comparing those measurements to the patient's baseline or known biomarker thresholds. Measurements below baseline indicate compliance to therapy. Measurements above the baseline may indicated non-compliance to therapy. Examples of biomarkers have been previously described. This is not intended to be an exhaustive list.

Other embodiments of the invention use the gathered information to diagnose or identify steroid refractory and/or steroid insensitive asthma. In one embodiment, steroid refractory or insensitive asthma may be determined by a patient continuing to show symptoms of asthma despite a high dose of steroid and confirmation of compliance by a biomarker or group of biomarkers. This embodiment may also include documenting the use of a biomarker or group of biomarkers to predict response and/or monitor adherence to steroids as the dose increases throughout the course of treatment. This data may be combined with other information gathered by the invention.

Other embodiments of the invention may be used to diagnose or identify a specific asthma phenotype.

Other embodiments of the invention may be used to diagnose or identify the presence or absence of eosinophilic airway inflammation.

Other embodiments of the invention may be used to determine the likelihood of response to a biological, oral or inhaled therapy. Examples of biological therapies include but is not limited to those targeting Th2 high or Th2 Low inflammation. Specific examples include but is not limited to IL-13, IL-4, IL-5, IgE, TLR9, TSLP etc. Examples of oral and inhaled therapies include CrTH2, leukotriene modifies, corticosteroids, theophylline, muscarinic antagonists, tiotropium, or combination therapies containing multiple active ingredients (e.g. inhaled corticosteroid/long acting beta2-agonist or inhaled corticosteroid/long acting beta2-agonist/long acting muscarinic antagonists etc.). Therapeutics may be short or long acting.

Other embodiments of the invention may use the collected information to determine the level of disease control in one patient or a patient population.

Other embodiments of the invention may be used to identify treatment failure on inhaled corticosteroids.

In another embodiment of the invention, the information gathered may be used to determine effectiveness of therapy or failure of therapy. Effectiveness may be determined by a drugs ability to keep one or several biomarkers at or below a baseline reading. Ineffectiveness or failure of therapy may be determined by a biomarker measurement that is above a baseline reading for a particular patient.

In one embodiment of the invention, the information gathered may be used to determine proper inhaler technique. In this embodiment, a biomarker or biomarkers may be used confirm deposition of the drug to the lung or pharmacodynamic effect.

In one embodiment, exhaled nitric oxide is used as a biomarker to predict response and monitor adherence and efficacy to inhaled corticosteroids. This information may be combined with other data gathered by the invention.

Other embodiments use the data to generate data for pharmaceutical and med tech research and development, identify patients for clinical trials and communicate with patients and physicians for marketing purposes.

Patients may use implementations of the invention to view the information about the status and progression of their condition over time and input information about themselves and find effective therapies based on the population in the database.

Under another embodiment of the invention, a trained medical professional may work in combination with the system monitoring software to identify trends and proactively intervene before patients have health problems or consume expensive medical resources such as emergency room visits.

FIG. 25 is an example of the type of information that is collected from the patient.

Figure 26:
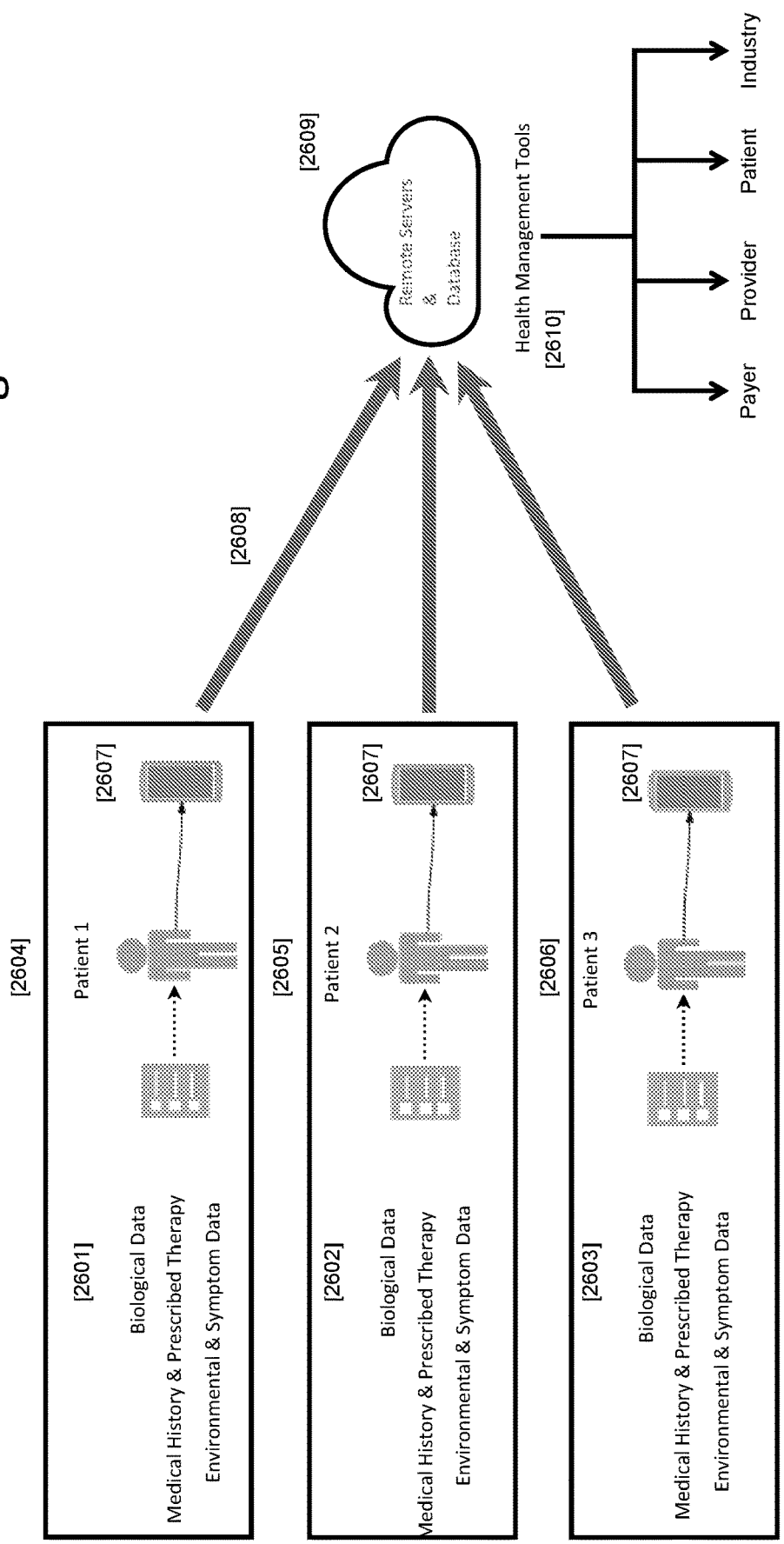
FIG. 26 illustrates an example of combining like data from multiple patients, sending the data to the cloud for analysis and generating meaningful information for multiple parties such as: payers, providers, patients, and industry i.e. pharmaceutical and medical device companies.

FIG. 26 illustrates an illustrative implementation of the invention gathering data [2601, 2602, 2603] from individual patients [2604, 2605, 2606] in a mobile application [2607] and sending the data [2608] to a remote database [2609] where it may be analyzed and queried by payers, providers, patients and industry [2610].

Figure 27:
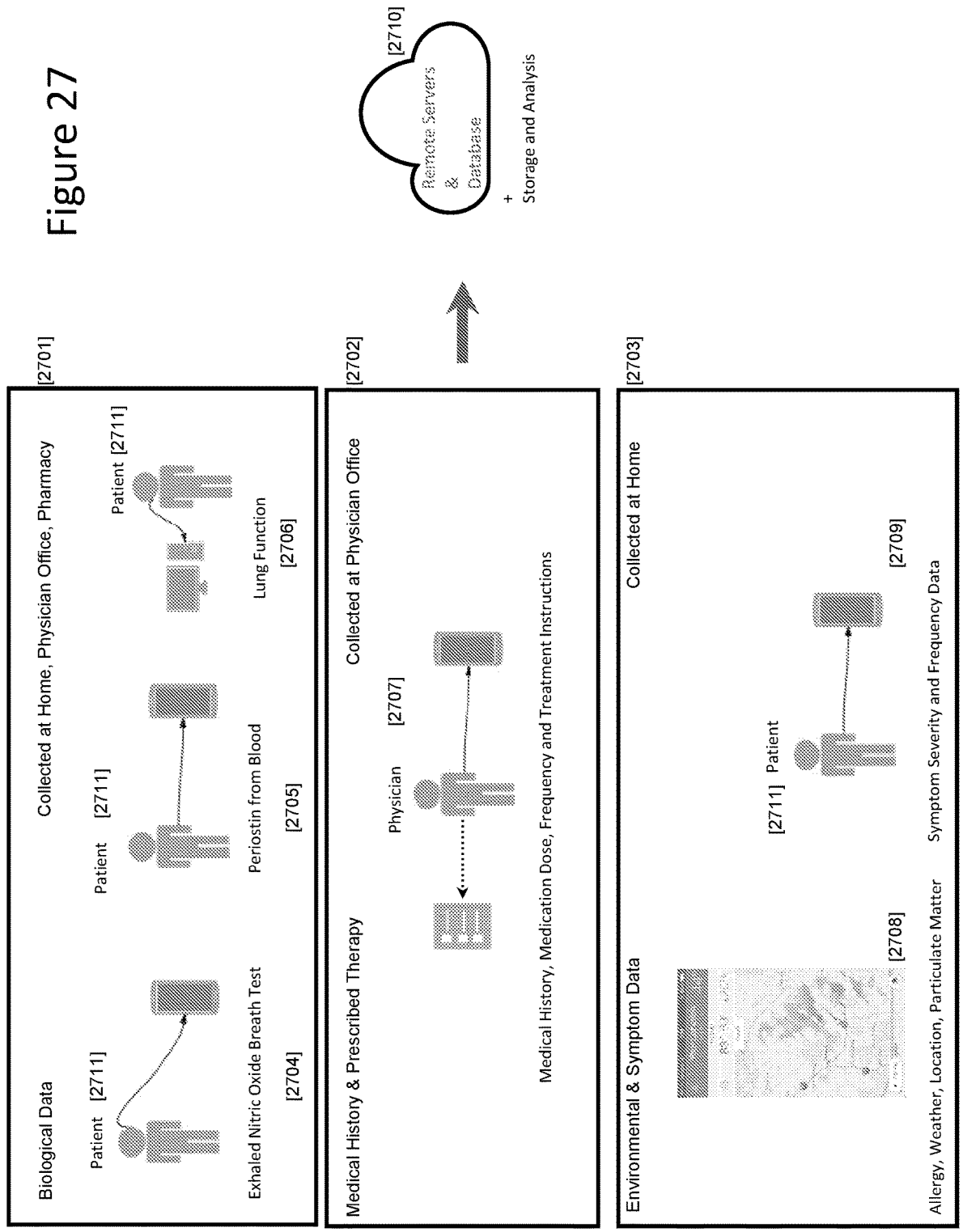
FIG. 27 depicts certain embodiments of a mobile application that collects data in various forms and at various locations from a single patient. The data is sent to the cloud for storage and analysis.

FIG. 27 illustrates examples of different types of data gathered for each patient either by manual or automatic collection. Biological data [2701] is gathered from a single patient [2711] at home, in the physician office or in the pharmacy. Biomarkers, such as exhaled nitric oxide measurement from a breath test [2704] and periostin from blood [2705] and lung function i.e. spirometry [2706], may be collected from a device attached to a computing device (i.e. phone, computer, tablet etc.) or the test result may be input manually. Other suitable blood biomarkers include blood eosinophils. Collecting additional biomarkers is possible without deviating from the spirit of the invention. Data collected regarding medical history and prescribed therapy [2702] may be collected at home and/or the physician office and is overseen by the physician [2707]. This data may be input manually or pulled automatically from a medical record. Environmental and symptom data [2703] is collected automatically and manually. Environmental data [2708] may include weather, air pollution, and/or allergen index. Location data may be provided by sensors inside of smart phones and overlaid onto environmental data. Particulate matter may be synced by a device with an embedded sensor located in the patient's home. Symptom data [2709] is gathered by querying the patient in between visits about the frequency and severity of their symptoms and about the degree to which the condition is impairing their daily life. All of this information is sent to remote servers for storage and analysis [2710].

Figure 28:
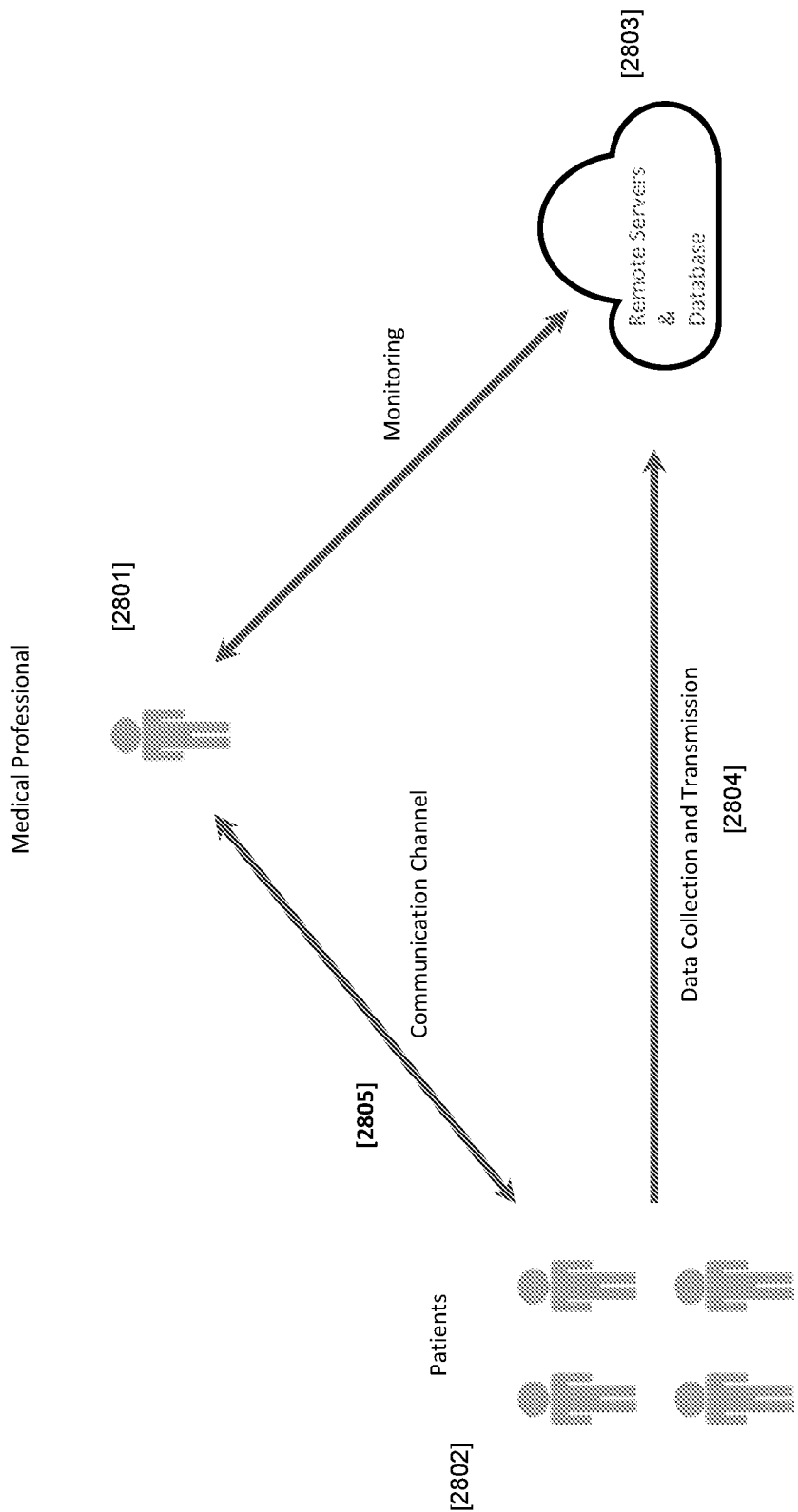
FIG. 28 depicts certain embodiments of a medical professional monitoring the data collected from patients.

FIG. 28 illustrates a monitoring system for chronic respiratory diseases. Data is collected and transmitted [2804] from patients [2802] in various methods as described in the invention. The information is stored remotely [2803] and monitored by a health professional [2801] as a service. The health professional is able to communicate [2805] to the patients for a variety of reasons related to their health status.

Figure 29:
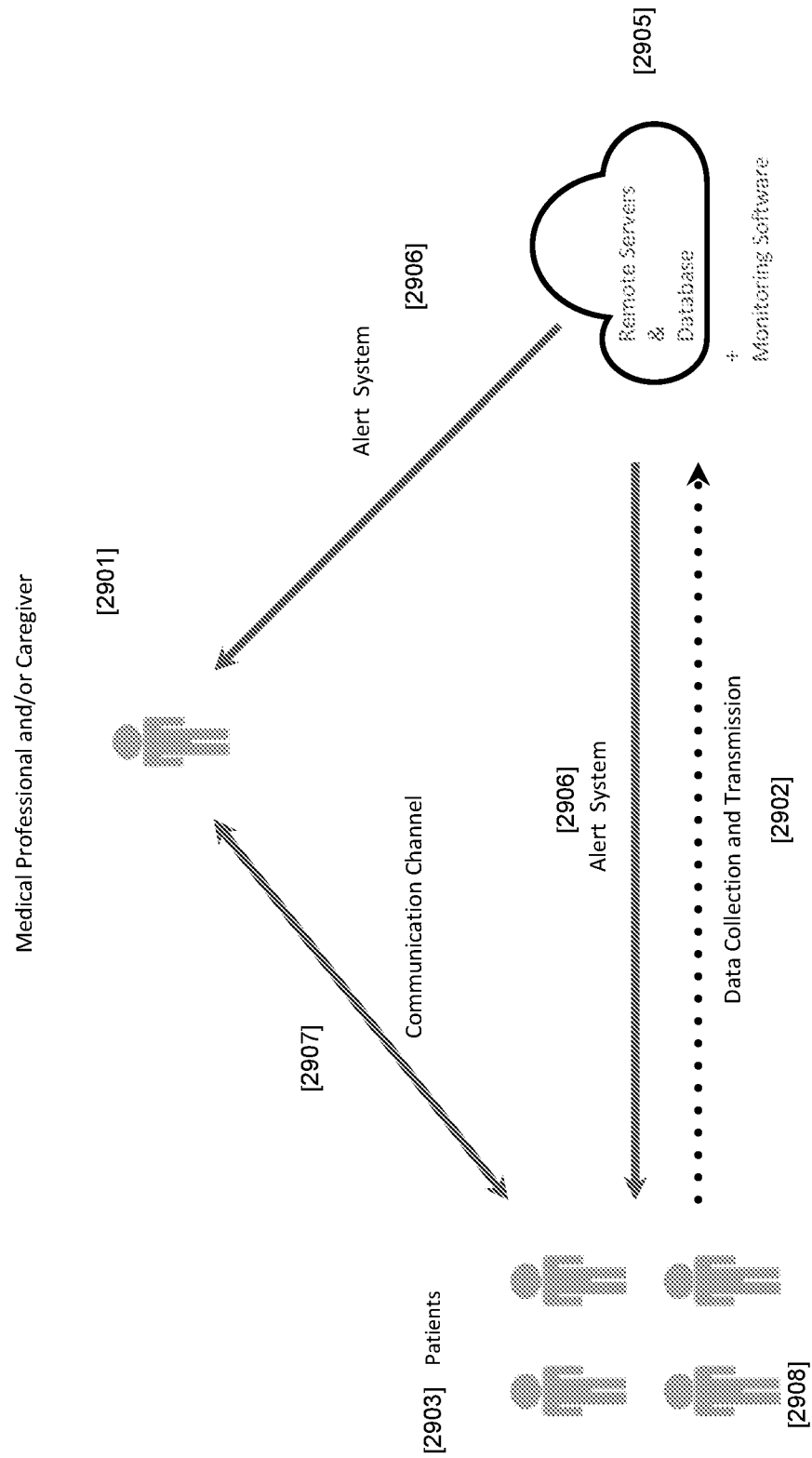
FIG. 29 depicts certain embodiments of a software monitoring system to proactively alert patients, medical professionals and/or caregivers of trend changes in health status.

FIG. 29 illustrates a software based monitoring system for chronic respiratory diseases. Data collected and transmitted from patients [2902], [2903] in various methods as described in the invention. The data is stored and monitored remotely [2905] and an alert system is triggered [2906] when the patients' information trends or passes beyond a predetermined threshold. For example, when a patient's nitric oxide levels rises between 10-20% versus a previous measurement or passes 25 or 50 ppb. The thresholds may be based on predetermined clinical guidelines and/or the characteristics of a patient (e.g. age, height, weight etc.). Ambient pollution levels may also trigger an alert. When an alert is triggered, the medical professional and/or caregiver [2901] and the individual patient [2908] may be alerted. The health professional and/or caregiver is able to communicate [2907] to the patients for a variety of reasons related to their health status.

Aspects of the techniques and systems related to measuring the concentration of an analyte in a fluid sample and/or performing a calibration on the devices as disclosed herein may be implemented as a computer program product for use with a computer system or computerized electronic device, using, e.g., a processor/microprocessor. Such implementations may include a series of computer instructions, or logic, fixed either on a tangible/non-transitory medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein.

The invention claimed is:

1. A method for determining the concentration of an analyte in a fluid sample, said method comprising:
   providing a system for determining the concentration of at least one analyte in a fluid sample, the system comprising:
      a base substrate;
      a first electrode pair disposed over the substrate;
      a conversion chamber adapted for producing an altered analyte by oxidizing or reducing the at least one analyte in the fluid sample; and
      an active sensing chemistry in electrical communication with the first electrode pair;
      wherein the active sensing chemistry is responsive to the altered analyte and wherein the active sensing chemistry forms an irreversible chemical bond with the altered analyte
   measuring at least one of a voltage across the first electrode pair, a resistance across the first electrode pair, and a current flow across the first electrode pair.

2. The method of claim 1, wherein the base substrate, first electrode pair, and active sensing chemistry are on a test strip.

3. The method of claim 1, wherein the fluid sample is recirculated between the conversion chamber and the test strip chamber.

4. A system for determining the concentration of at least one analyte in a fluid sample, the system comprising:
   a base substrate;
   a first electrode pair disposed over the substrate; and
   a conversion chamber adapted for producing an altered analyte by oxidizing or reducing the at least one analyte in the fluid sample; and
   an active sensing chemistry in electrical communication with the first electrode pair, wherein the active sensing chemistry is responsive to the altered analyte, and wherein the active sensing chemistry forms an irreversible chemical bond with the altered analyte.

5. The system of claim 4 further comprising a second electrode pair disposed over the substrate and a second sensing chemistry in electrical communication with the second electrode pair.

6. The system of claim 5 wherein one or more of the active sensing chemistry or the second sensing chemistry contain one or more of carbonyl groups, nanostructures, functional organic dyes, heterocyclic macrocycles, metal oxides, or transition metals.

7. The system of claim 5 wherein the active sensing chemistry or the second sensing chemistry is at least one of a line shape bridging the electrode pair and a coffee ring shape bridging the electrode pair.

8. The system of claim 4 wherein the altered analyte saturates the sensing chemistry after at least a single exposure to the altered analyte.

9. The system of claim 4 wherein the chemical bond is selected from the group consisting of coordination bonds, covalent bonds, hydrogen bonds, ionic bonds, and polar bonds.

10. The system of claim 4 wherein the system is adapted to sense one or more of nitric oxide, nitrogen dioxide, nitrogen monoxide, hydrogen, methane, acetone, sulfur dioxide, carbon monoxide, or ozone.

11. The system of claim 4 further comprising at least one sensor to determine one or more of humidity, temperature, or pressure.

12. The system of claim 4 further comprising a dehumidifier adapted to adjust humidity in the sample.

13. The system of claim 12 wherein the dehumidifier comprises at least one of a nafion tube and a desiccant.

14. The system of claim 13 wherein the desiccant comprises at least one of a silica gel and an oxidizer.

15. The system of claim 4 further comprising a filter adapted to remove a gas from the sample determined to interfere with the sensor.

16. The system of claim 15 wherein the filter comprises a nafion tube.

17. The system of claim 4 wherein the conversion chamber is removable.

18. The system of claim 4 wherein the conversion chamber comprises at least one of potassium permanganate and sodium permanganate.

19. The system of claim 18 wherein the potassium permanganate is suspended on at least one of a substrate and a silica gel.

20. The system of claim 18 wherein the sodium permanganate is suspended on at least one of a substrate and a silica gel.

21. The system of claim 4 wherein the conversion chamber comprises one or more of a UV source, an infrared source, a radio frequency source, or a corona discharge source.

22. The system of claim 4 wherein the conversion chamber is adapted to oxidize nitrogen monoxide to nitrogen dioxide.

23. The system of claim 4 wherein the active sensing chemistry is configured to be responsive to nitrogen dioxide.

24. The system of claim 4, wherein the base substrate, first electrode pair, and active sensing chemistry are on a test strip.

25. A system for determining the concentration of at least one analyte in a fluid sample, the system comprising:
   a base substrate;
   a first electrode pair disposed over the substrate; and
   an active sensing chemistry in electrical communication with the first electrode pair;

wherein the active sensing chemistry is responsive to the analyte, wherein the active sensing chemistry forms an irreversible chemical bond with the analyte, and wherein the active sensing chemistry is a coffee ring shape bridging the electrode pair.

26. A method for determining the concentration of an analyte in a fluid sample, said method comprising:
providing a system for determining the concentration of at least one analyte in a fluid sample, the system comprising:
a base substrate,
a first electrode pair disposed over the substrate, and
an active sensing chemistry in electrical communication with the first electrode pair,
wherein the active sensing chemistry is responsive to the analyte, wherein the active sensing chemistry forms an irreversible chemical bond with the analyte, wherein the active sensing chemistry is a coffee ring shape bridging the electrode pair; and
measuring at least one of a voltage across the first electrode pair, a resistance across the first electrode pair, and a current flow across the first electrode pair.

* * * * *